United States Patent
Kobayashi et al.

(10) Patent No.: US 6,172,264 B1
(45) Date of Patent: Jan. 9, 2001

(54) TRIPHENYLAMINE DERIVATIVE, CHARGE-TRANSPORTING MATERIAL COMPRISING THE SAME, AND ELECTROPHOTOGRAPHIC PHOTORECEPTOR

(75) Inventors: Tohru Kobayashi; Yoshimasa Matsushima; Hiroshi Sugiyama; Toshimitsu Hagiwara, all of Kanagawa (JP)

(73) Assignee: Takasago International Corporation, Tokyo (JP)

( * ) Notice: Under 35 U.S.C. 154(b), the term of this patent shall be extended for 0 days.

(21) Appl. No.: 09/253,028

(22) Filed: Feb. 19, 1999

Related U.S. Application Data

(62) Division of application No. 08/894,878, filed on Sep. 2, 1997, now Pat. No. 5,910,610.

(30) Foreign Application Priority Data

Mar. 1, 1995 (JP) .................................... 7-065270

(51) Int. Cl.[7] .................................... C07C 211/54
(52) U.S. Cl. .................... 564/433; 564/315; 564/434
(58) Field of Search .................... 564/433, 315, 564/443

(56) References Cited

U.S. PATENT DOCUMENTS

| | | |
|---|---|---|
| 4,769,302 | 9/1988 | Ueda . |
| 5,246,808 | 9/1993 | Hanatani et al. . |
| 5,573,878 * | 11/1996 | Hagiwara ................ 430/59 |
| 5,712,360 * | 1/1998 | Kobayashi ............... 528/38 |
| 5,814,244 * | 9/1998 | Kreuder ................ 252/301.16 |
| 5,824,443 * | 10/1998 | Kushibiki ................ 430/59 |

FOREIGN PATENT DOCUMENTS

| | | |
|---|---|---|
| 0-650956 A1 | 3/1995 | (EP) . |
| 2-226159 | 9/1990 | (JP) . |
| 6-332206 | 12/1994 | (JP) . |

OTHER PUBLICATIONS

CA:116:193331 of HU 56534, Nov. 1989.*
March "Advanced Organic Chemistry" textbook, published by McGraw Hill pp. 417–418, 1968.*

* cited by examiner

*Primary Examiner*—Jean F Vollano
(74) *Attorney, Agent, or Firm*—Sughrue, Mion, Zinn, Macpeak & Seas, PLLC

(57) ABSTRACT

A triphenylamine derivative, represented by the following general formula (1):

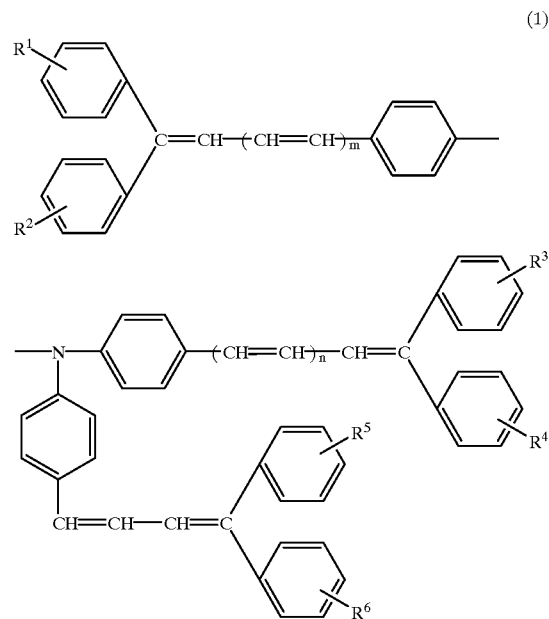

wherein $R^1$, $R^2$, $R^3$, $R^4$, $R^5$ and $R^6$ each represents a hydrogen atom, a lower alkyl group, an alkoxy group, a halogen atom or an aryl group which may have a substituent group; and m and n each represents 0 or 1.

8 Claims, No Drawings

TRIPHENYLAMINE DERIVATIVE, CHARGE-TRANSPORTING MATERIAL COMPRISING THE SAME, AND ELECTROPHOTOGRAPHIC PHOTORECEPTOR

This is a divisional of application Ser. No. 08/894,878 filed Sep. 2, 1997, now U.S. Pat. No. 5,910,610, the disclosure of which is incorporated herein by reference.

TECHNICAL FIELD

The present invention relates to a novel triphenylamine derivative represented by the following general formula (1):

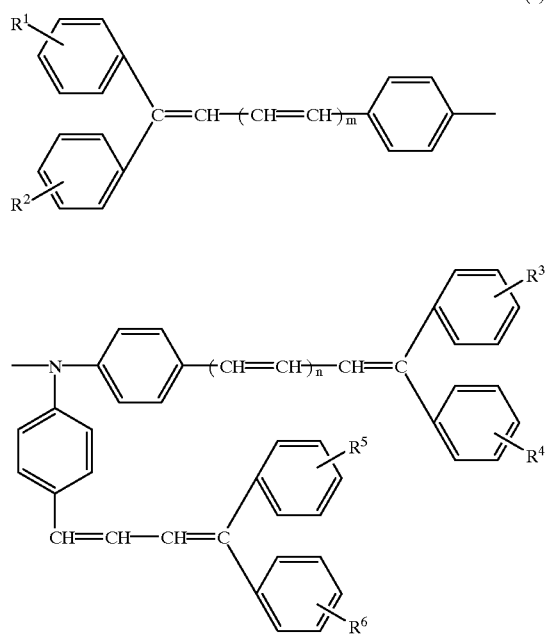

(1)

wherein $R^1$, $R^2$, $R^3$, $R^4$, $R^5$, and $R^6$ may be the same or different and each represents a hydrogen atom, a lower alkyl group, an alkoxy group, a phenoxy group, a halogen atom, or an aryl group which may have a substituent group, and m and n each represents 0 or 1. This invention further relates to a charge-transporting material comprising the novel triphenylamine derivative and to an electrophotographic photoreceptor containing the charge-transporting material.

The present invention also relates to a process for the preparation of a triphenylamine derivative represented by the following general formula (6):

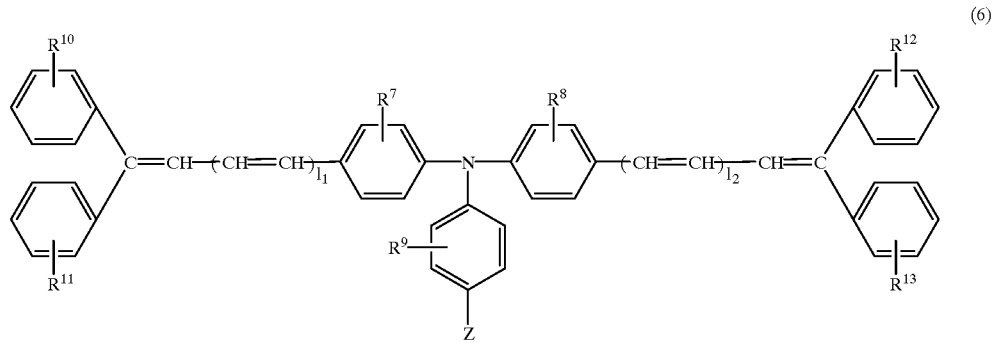

(6)

wherein $R^7$ to $R^{13}$ may be the same or different and each represents a hydrogen atom, a lower alkyl group, an alkoxy group, a phenoxy group, a halogen atom or an aryl group which may have a substituent group; $l_1$ and $l_2$ each represents 0 or 1; and Z represents a hydrogen atom, a lower alkyl group, an alkoxy group, a phenoxy group, a halogen atom, an aryl group which may have a substituent group or a group represented by any one of the following general formulae (7a), (7b) and (7c):

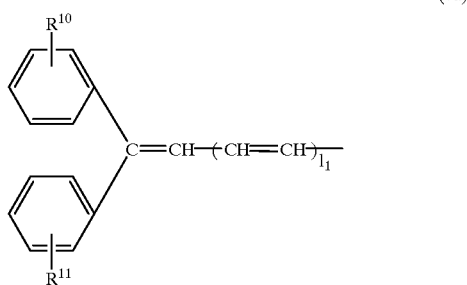

(7a)

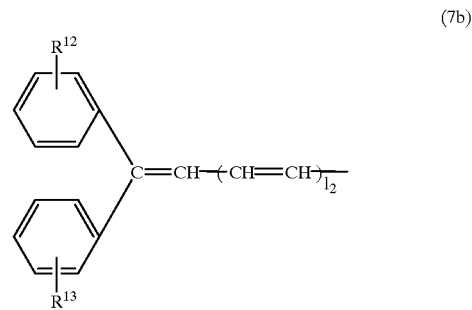

(7b)

-continued (7c)

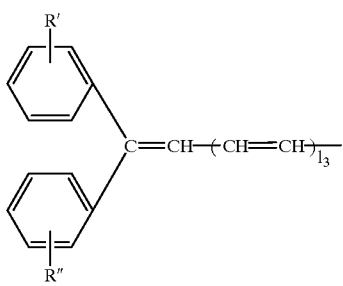

wherein $R^{10}$ to $R^{13}$, $l_1$ and $l_2$ are as defined in the foregoing general formula (6); R' and R" may be the same or different and each represents a hydrogen atom, a lower alkyl group, an alkoxy group, a phenoxy group, a halogen atom or an aryl group which may have a substituent group; and $l_3$ represents 0 or 1, said triphenylamine derivative including the foregoing novel triphenylamine derivative represented by the general formula (1).

The present invention further relates to a process for the preparation of a poly-formyl-substituted triphenylamine derivative represented by the following general formula (4) useful as an intermediate for the preparation of the foregoing triphenylamine derivative represented by the general formula (1) and/or (6):

(4)

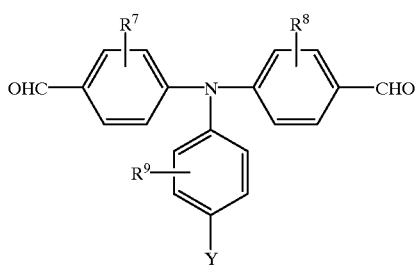

wherein $R^7$, $R^8$ and $R^9$ may be the same or different and each represents a hydrogen atom, a lower alkyl group, an alkoxy group, a phenoxy group, an aryl group which may have a substituent group or a halogen atom; and Y represents a formyl group, a hydrogen atom, a lower alkyl group, an alkoxy group, a phenoxy group, a halogen atom or an aryl group which may have a substituent group.

BACKGROUND ART

Inorganic photoconductive materials recently in use include amorphous silicon, amorphous selenium, cadmium sulfide, zinc oxide, and the like. However, some of these materials are expensive because of difficulties in production thereof, while others are toxic and disadvantageous from the standpoint of environmental protection.

On the other hand, as organic photoconductors, ones of the type comprising, in particular, a charge-generating material and a charge-transporting material which respectively perform their functions are proposed extensively (e.g., U.S. Pat. No. 3,791,826). In this type, there is the possibility that a high-sensitivity electrophotographic photoreceptor might be obtained by using a substance which efficiently generates carriers (The term "carriers" means "charges"; the same applies hereinafter) as the charge-generating material in combination with a substance having high charge-transporting ability as the charge-transporting material.

Of these materials, the charge-transporting material is required to efficiently receive the carriers generated in the charge-generating material upon light irradiation in an electric field and permit them to rapidly move through the photosensitive layer to extinguish the surface charges promptly. The speed at which carriers move per unit electric field is called carrier mobility. A high carrier mobility means that carriers rapidly move in the charge-transporting layer. Any charge-transporting material has its intrinsic carrier mobility and, hence, it is necessary that for attaining a high carrier mobility, a material having a high carrier mobility be employed. However, the attainable carrier mobilities have not yet reached a sufficient level.

Further, in the case of applying a charge-transporting material after dissolving it in an organic solvent along with a binder polymer, it is necessary to form a thin homogeneous organic coating film free from crystallization and pinhole formation. This is because when a high electric field is applied to the thin film obtained, the part having microcrystals or pinholes undergoes dielectric breakdown or causes noise.

In addition to the satisfactory properties of the charge-generating material and of the charge-transporting material, it is also important that carriers should be efficiently injected from the charge-generating material into the charge-transporting material, i.e., from the charge-generating layer into the charge-transporting layer. This injection of charges depends on the properties of the interface between the charge-generating material (or charge-generating layer) and the charge-transporting material (or charge-transporting layer) and varies with combinations of various materials. Since a charge-transporting material should meet various requirements as described above, charge-transporting materials having a variety of properties are being developed.

Among conventional charge-transporting materials, the styryl compound represented by formula (A):

(A)

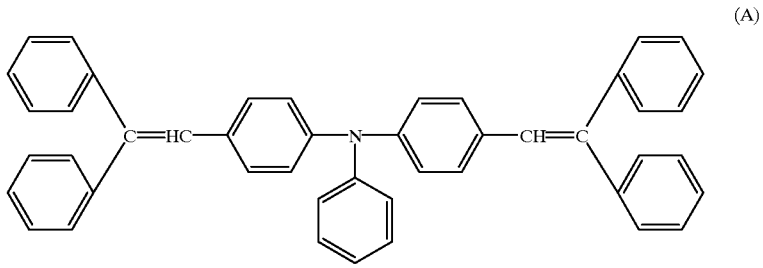

is, for example, proposed in JP-A-60-174749. (The term "JP-A" as used herein means an "unexamined published Japanese patent application.")

Moreover, a styryl compound represented by formula (B):

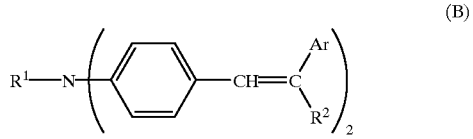

(B)

(wherein R¹ represents an optionally substituted alkyl group or an aryl group which may have a substituent group, R² represents a hydrogen atom, an optionally substituted alkyl group, or an aryl group which may have a substituent group, and Ar represents an aryl group which may have a substituent group)
is proposed in JP-A-60-175052.

Furthermore, compounds similar to the compound (B) described above are proposed in, for example, JP-A-62-120346, JP-A-1-217357, JP-A-4-57056, and JP-A-4-292663.

On the other hand, a styryl compound represented by formula (C):

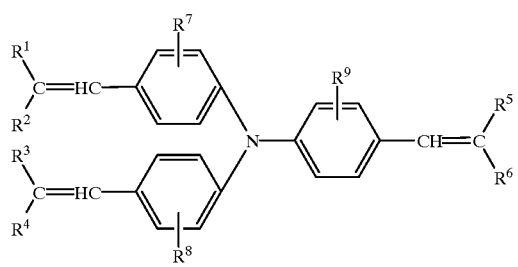

(C)

(wherein $R^1$, $R^3$, and $R^5$ each represents a hydrogen atom, an alkyl group, an aryl group which may have a substituent group, an optionally substituted aralkyl group, or an optionally substituted heterocyclic group; $R^2$, $R^4$, and $R^6$ each represents an aryl group which may have a substituent group, an optionally substituted aralkyl group, or an optionally substituted heterocyclic group; $R^1$ and $R^2$, $R^3$ and $R^4$, and $R^5$ and $R^6$ may be bonded to each other to form a ring; and $R^7$, $R^8$, and $R^9$ each represents a hydrogen atom, an alkyl group, an alkoxy group, an aralkyl group, or an aryl group) is proposed in JP-B-6-93124. (The term "JP-B" as used herein means an "examined Japanese patent publication.")

Compounds similar to the compound (C) described above are proposed in JP-A-63-163361 and JP-A-6-332206. In JP-A-4-292663 is proposed a hydrazone compound represented by formula (D):

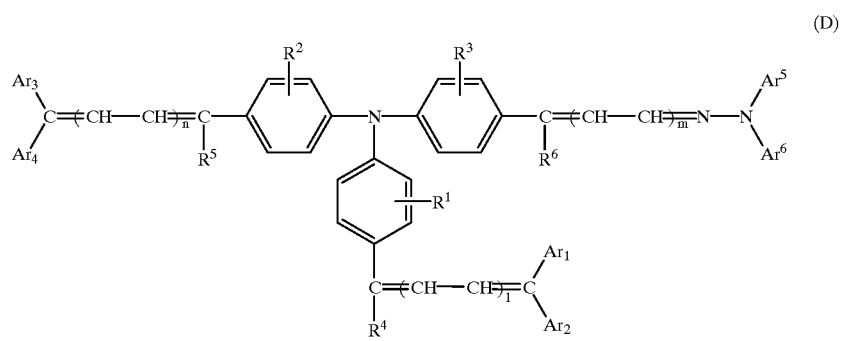

(D)

(wherein $R^1$, $R^2$, $R^3$, $R^4$, $R^5$, and $R^6$ may be the same or different and each represents a hydrogen atom, an optionally substituted alkyl group, an optionally substituted alkoxy group, an optionally substituted aralkyl group, or an aryl group which may have a substituent group; $Ar^1$, $Ar^2$, $Ar^3$, $Ar^4$, $Ar^5$, and $Ar^6$ may be the same or different and each represents a hydrogen atom, an optionally substituted alkyl group, an aryl group which may have a substituent group, an optionally substituted aralkyl group, or an optionally substituted heterocyclic group; and l, m, and n each represents 0 or 1; provided that $Ar^1$, $Ar^2$, $Ar^3$, $Ar^4$, $Ar^5$, and $Ar^6$ should not be a hydrogen atom at the same time).

The demand for charge-transporting materials is growing more and more, with which there is a desire for a newer material which is capable of satisfying various requirements.

In JP-A-4-57056, for example, there is a description to the effect that the compound (E) specified below partly separated out as crystals during the preparation of a photoreceptor because of the poor solubility of the compound.

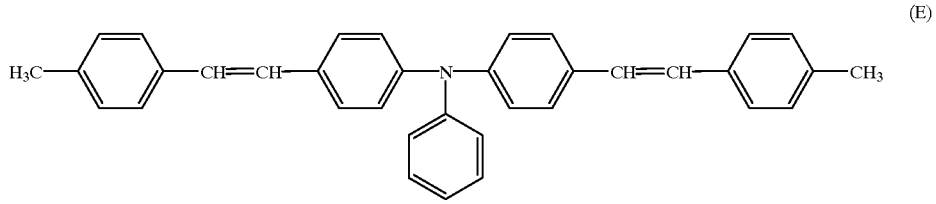

(E)

Furthermore, in JP-A-6-332206, there is a description to the effect that a charge-transporting layer comprising the compound (F) specified below and a binder polymer develops cracks.

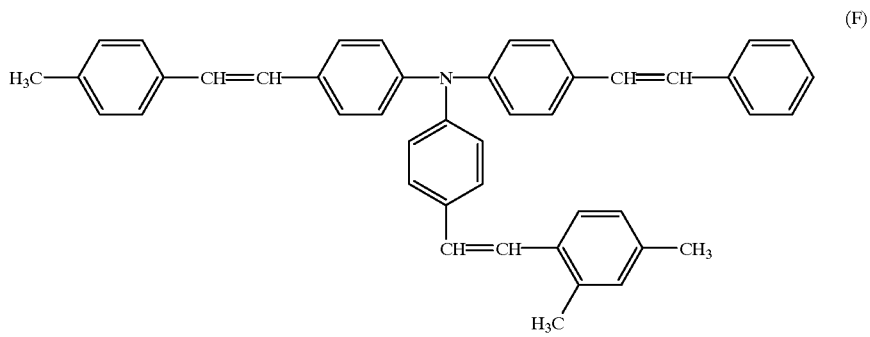

(F)

Further, JP-A-2-226159 discloses a compound represented by the following general formula G:

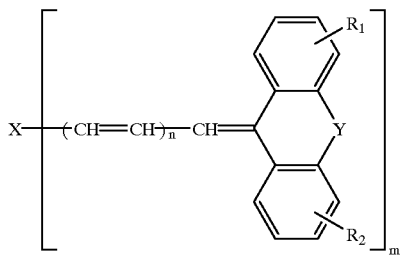

(G)

wherein X represents an aryl, arylene, heterocyclic, diarylamino or triarylamino group which may have a substituent group; Y represents a group selected from the group consisting of:

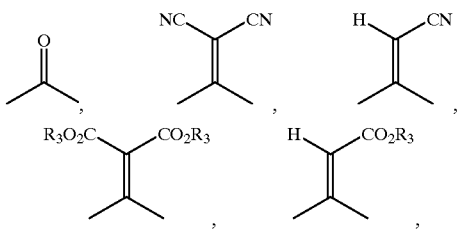

—$CH_2$—, —$CH_2CH_2$—, —CH=CH—, or a single bond; n represents an integer of 0 or 1; m represents an integer of from 1 to 3; $R_1$ and $R_2$ may be the same or different and each represents an alkyl, aryl, aralkyl, cyano or nitro group which may have a substituent group or a halogen atom; and $R_3$ represents an alkyl, aryl or aralkyl group which may have a substituent group. However, this is a complex compound having two phenyl groups which are connected to each other via Y to form another ring.

The preparation of the foregoing various triphenylamine derivatives to be used as known charge-transporting materials can be accomplished by a process which comprises reacting the corresponding compound having a triphenylamine skeleton with a Vilsmeier reagent prepared from a halogenating reagent such as phosphorus oxychloride and a formylating agent such as N,N-dimethylformamide to obtain an iminium intermediate, and then hydrolyzing the iminium intermediate with an alkaline aqueous solution to prepare a formyl-substituted triphenylamine derivative which is then reacted with a predetermined phosphorous acid ester, as described in "Jikken Kagaku Koza", vol. 14, page 688 (published by Maruzen).

However, if the foregoing process causes the reaction of triphenylamine with one equivalent of a Vilsmeier reagent, the resulting monoiminium salt has an extremely deteriorated nucleophilicity that makes itself difficult to react with another Vilsmeier reagent, making it impossible to efficiently produce the desired diiminium salt. Accordingly, the foregoing process can easily accomplish the synthesis of a monoaldehyde of triphenylamine but can hardly accomplish the synthesis of a diformylation product of triphenylamine. Even if the foregoing reaction is effected in the presence of a large amount of a Vilsmeier reagent or over an extended period of time, the resulting yield is very low. For example, JP-A-7-173112 discloses that the yield of 4,4'-diformyltriphenylamine is 39.5% and the yield of 4-methyl-4,4'-diformyltriphenylamine is only 11.8%.

Bouanane et al. reported that ordinary Vilsmeier reaction of triphenylamine produces 4,4'-diformyltriphenylamine in a yield of 75% (C. R. Hebd. Seances Acad. Sci., Ser. C, Vol. 279, No. 5, pp. 187–190). However, according to the inventors' experiment, 4,4'-diformyltriphenylamine cannot be obtained in such a high yield. Further, this reaction process is very disadvantageous for the reaction of the intermediate with a further Vilsmeier reagent that produces a triiminium salt, making it very difficult to synthesize a triformylation product of triphenylamine.

As mentioned above, no processes for efficient synthesis of 4,4'-diformultriphenylamine derivative and 4,4',4"-triformyltriphenylamine derivative have been known.

Accordingly, an object of the present invention is to provide a novel charge-transporting material which gives a stable film attaining a high carrier mobility and which, when used in an electrophotographic photoreceptor, is also excellent in various properties.

It is another object of the present invention to provide an electrophotographic photoreceptor comprising a novel material having the foregoing properties as a charge-transporting material.

It is a further object of the present invention to provide a process for the efficient preparation of a novel charge-transporting material having the foregoing properties. It is a still further object of the present invention to provide an improved process for the preparation of an intermediate substance useful for the preparation of the novel charge-transporting material.

DISCLOSURE OF THE INVENTION

As a result of intensive studies made by the present inventors on a wide range of compounds under these circumstances, they have found that the problems described above can be overcome with a triphenylamine derivative in which one of the phenyl groups of triphenylamine has a diphenylbutadienyl-framework substituent and the other two phenyl groups each has a diphenylbutadienyl- or diphenylvinyl-framework substituent, and which is represented by the following general formula (1):

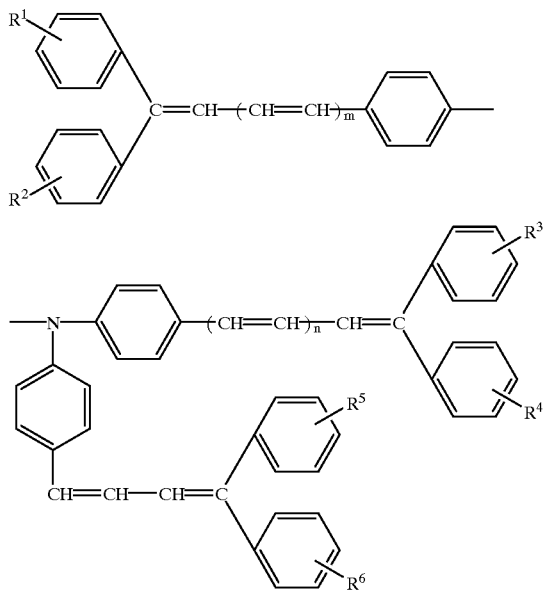

wherein $R^1$, $R^2$, $R^3$, $R^4$, $R^5$, and $R^6$ may be the same or different and each represents a hydrogen atom, a lower alkyl group, an alkoxy group, a phenoxy group, a halogen atom, or an aryl group which may have a substituent group, and m and n each represents 0 or 1. The present invention has been completed based on this finding.

That is, the present inventors have found that the triphenylamine derivative (1) has good solubility in binder polymers, suffers neither crystallization nor pinhole formation, and is capable of attaining a high carrier mobility, and that a photoreceptor employing this compound is high in sensitivity and low in residual potential.

The present invention relates to a novel triphenylamine derivative, represented by the following general formula (1):

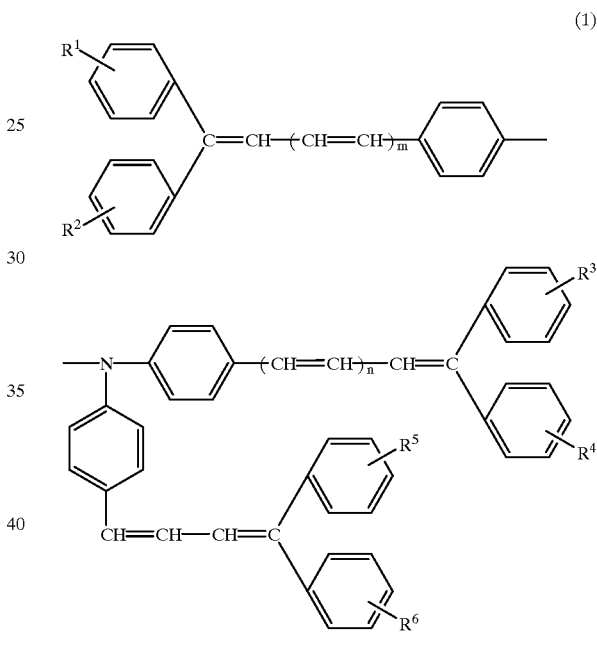

wherein $R^1$, $R^2$, $R^3$, $R^4$, $R^5$ and $R^6$ may be the same or different and each represent a hydrogen atom, a lower alkyl group, an alkoxy group, a phenoxy group, a halogen atom or an aryl group which may have a substituent group; and m and n each represents 0 or 1.

The present invention also relates to a charge-transporting material, comprising a mixture of a novel triphenylamine derivative represented by the foregoing general formula (1) and a triphenylamine derivative represented by the following general formula (2):

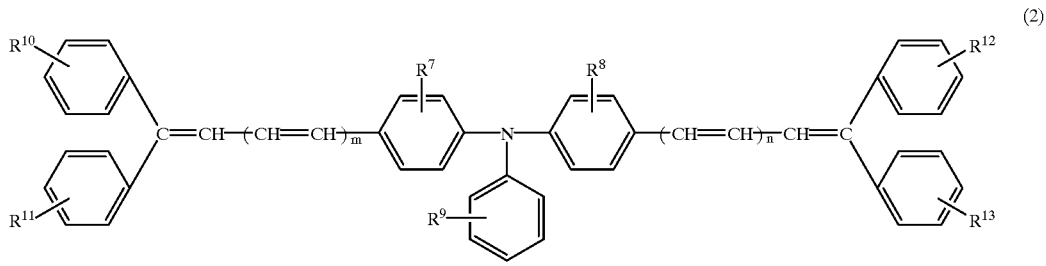

(2)

wherein $R^7$, $R^8$, $R^9$, $R^{10}$, $R^{11}$, $R^{12}$ and $R^{13}$ may be the same or different and each represents a hydrogen atom, a lower alkyl group, an alkoxy group, a phenoxy group, a halogen atom or an aryl group which may have a substituent group; and m and n each represents 0 or 1.

The present invention also relates to a process for the preparation of a triphenylamine derivative represented by the following general formula (6):

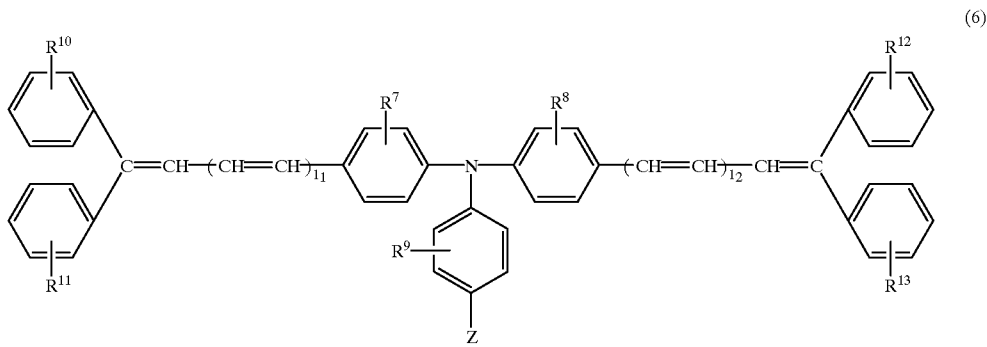

(6)

wherein $R^7$, $R^8$, $R^9$, $R^{10}$, $R^{11}$, $R^{12}$ and $R^{13}$ may be the same or different and each represents a hydrogen atom, a lower alkyl group, an alkoxy group, a phenoxy group, a halogen atom or an aryl group which may have a substituent group; $l_1$ and $l_2$ each represents 0 or 1; and Z represents a hydrogen atom, a lower alkyl group, an alkoxy group, a phenoxy group, a halogen atom, an aryl group which may have a substituent group or a group represented by any one of the following general formulae (7a), (7b) and (7c):

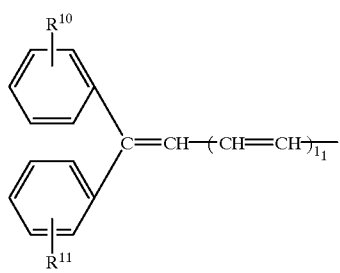

(7a)

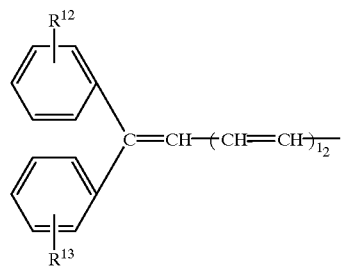

(7b)

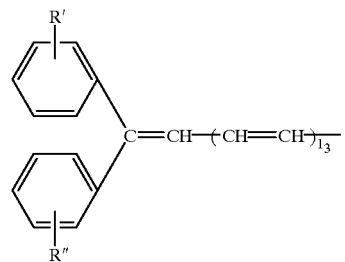

(7c)

wherein $R^{10}$ to $R^{13}$ and $l_1$ and $l_2$ are as defined above; R' and R" have the same meaning as $R^7$ to $R^{13}$; $l_3$ represents 0 or 1, which comprises reacting a triphenylamine derivative represented by the following general formula (3):

(3)

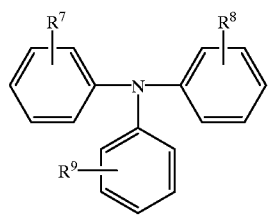

wherein $R^7$, $R^8$ and $R^9$ are as defined above with a Vilsmeier reagent prepared from a halogenating reagent and an N-substituted formamide in the presence of an acid selected from the group consisting of Lewis acid and protonic acid, subjecting the reaction product to hydrolysis with an alkaline aqueous solution to obtain a poly-formyl-substituted triphenylamine derivative represented by the following general formula (4):

(4)

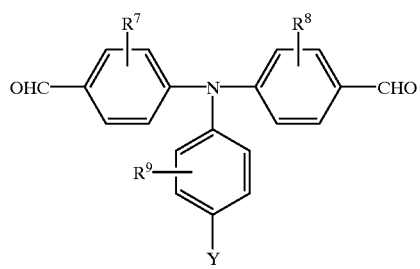

wherein $R^7$, $R^8$ and $R^9$ are as defined above and Y represents a formyl group, a hydrogen atom, a lower alkyl group, an alkoxy group, a phenoxy group, a halogen atom or an aryl group which may have a substituent group, and then reacting said poly-formyl-substituted triphenylamine derivative of the general formula (4) with a phosphorous acid ester compound represented by any one of the following general formulae (5a), (5b) and (5c):

(5a)

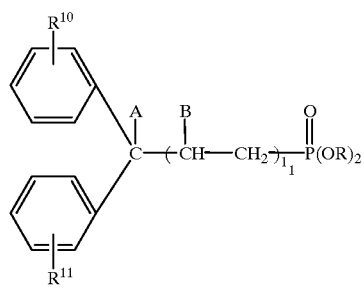

(5b)

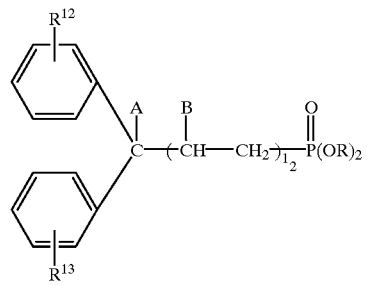

(5c)

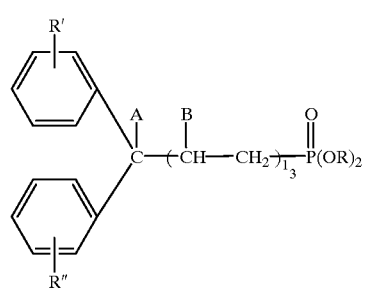

wherein $R^{10}$, $R^{11}$, $R^{12}$, $R^{13}$, R, R', R", $l_1$, $l_2$ and $l_3$ are as defined above, with the proviso that if $l_1$, $l_2$ or $l_3$ is 0, A represents a hydrogen atom, and if $l_1$, $l_2$ or $l_3$ is 1, A and B is connected to each other to form a single bond.

The present invention further relates to a process for the preparation of a triphenylamine derivative represented by the foregoing general formula (6) wherein the poly-formyl-substituted triphenylamine derivative represented by the foregoing general formula (4) is a mixture of diformyl-substituted triphenylamine derivative wherein the substituent Y is a hydrogen atom and tri-formyl-substituted triphenylamine derivative wherein the substituent Y is a formyl group and the triphenylamine derivative represented by the foregoing general formula (6) is a mixture of triphenylamine derivative wherein the substituent Z is a hydrogen atom and triphenylamine derivative wherein the substituent Z is a group represented by the foregoing general formula (7).

The present invention further relates to a process for the preparation of a poly-formyl-substituted triphenylamine derivative represented by the following general formula (4):

(4)

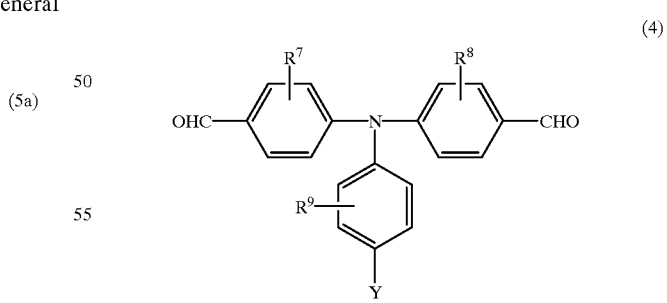

wherein $R^7$, $R^8$ and $R^9$ are as defined above; and Y represents a formyl group, a hydrogen atom, a lower alkyl group, an alkoxy group, a phenoxy group, a halogen atom or an aryl group which may have a substituent group, which comprises allowing a triphenylamine derivative represented by the following general formula (3):

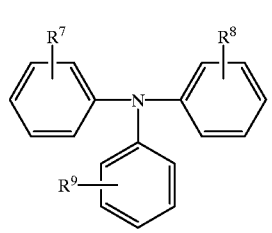

(3)

wherein $R^7$, $R^8$ and $R^9$ may be the same or different and each represents a hydrogen atom, a lower alkyl group, an alkoxy group, a phenoxy group, an aryl group which may have a substituent group or a halogen atom to react with a Vilsmeier reagent prepared from a halogenating reagent and an N-substituted formamide in the presence of an acid selected from the group consisting of Lewis acid and protonic acid, and then subjecting the reaction product to hydrolysis with an alkaline aqueous solution.

The present invention further relates to the foregoing process for the preparation of a poly-formyl-substituted triphenylamine derivative represented by the foregoing general formula (4) wherein the Lewis acid and protonic acid to be used in the reaction of the triphenylamine derivative represented by the foregoing general formula (3) with a Vilsmeier reagent are selected from the group consisting of zinc chloride, zinc bromide, boron trifluoride, aluminum chloride, titanium tetrachloride and tin chloride and from the group consisting of hydrogen chloride and hydrogen bromide, respectively.

The present invention further relates to the foregoing process for the preparation of a poly-formyl-substituted triphenylamine derivative represented by the foregoing general formula (4) wherein said Vilsmeier reagent is prepared from at least one halogenating reagent selected from the group consisting of phosphorus oxychloride, phosgene and thionyl chloride and at least one N-substituted formamide selected from the group consisting of N,N-dimethylformamide and N-methylformamide.

The present invention further relates to the foregoing process for the preparation of a poly-formyl-substituted triphenylamine derivative represented by the foregoing general formula (4) wherein the reaction of a triphenylamine derivative represented by the foregoing general formula (3) with a Vilsmeier reagent is effected in at least one reaction solvent selected from the group consisting of toluene, xylene, chlorobenzene and dichlorobenzene.

BEST MODE TO PRACTICE THE INVENTION

In the compound (1) of the present invention, $R^1$, $R^2$, $R^3$, $R^4$, $R^5$, and $R^6$ may be the same or different and each represents a hydrogen atom, a lower alkyl group, an alkoxy group, a phenoxy group, a halogen atom, or an aryl group which may have a substituent group. Examples of the lower alkyl group include alkyl groups having 1 to 4 carbon atoms, e.g., methyl, ethyl, n-propyl, isopropyl, n-butyl, and isobutyl, with methyl or ethyl being especially preferred.

Examples of the alkoxy group include alkoxy groups having 1 to 4 carbon atoms, e.g., methoxy, ethoxy, propoxy, and butoxy.

Examples of the halogen atom include fluorine, chlorine, bromine, and iodine.

Examples of the aryl group which may have a substituent group include phenyl, lower-alkyl-substituted phenyl groups, e.g., p-tolyl and 2,4-dimethylphenyl, lower-alkoxy-substituted phenyl groups, e.g., p-methoxyphenyl, and halogen-substituted phenyl groups, e.g., p-chlorophenyl.

Preferred examples of the compound (1) of this invention include the compounds shown in Tables 1, 2, and 3 below, but the compound (1) is not limited thereto.

TABLE 1

| Exemplified Compound | m | n | $R^1$ | $R^2$ | $R^3$ | $R^4$ | $R^5$ | $R^6$ |
|---|---|---|---|---|---|---|---|---|
| 1 | 1 | 1 | H | H | H | H | H | H |
| 2 | 1 | 1 | 4-Me | 4-Me | 4-Me | 4-Me | 4-Me | 4-Me |
| 3 | 1 | 1 | 4-Me | 4-Me | H | H | 4-Me | 4-Me |
| 4 | 1 | 1 | 4-Me | H | 4-Me | H | 4-Me | H |
| 5 | 1 | 1 | H | H | 4-Me | 4-Me | H | H |
| 6 | 1 | 1 | 3-Me | 3-Me | 3-Me | 3-Me | 3-Me | 3-Me |
| 7 | 1 | 1 | H | H | H | H | 4-Cl | 4-Cl |
| 8 | 1 | 1 | 4-MeO | H | 4-MeO | H | 4-MeO | H |
| 9 | 1 | 1 | H | H | H | H | 4-MeO | 4-MeO |
| 10 | 1 | 1 | 4-MeO | 4-MeO | 4-MeO | 4-MeO | 4-MeO | 4-MeO |
| 11 | 1 | 1 | 4-MeO | H | 4-MeO | H | 4-MeO | 4-MeO |
| 12 | 1 | 1 | 4-Me | H | 4-Me | H | 4-Me | 4-F |
| 13 | 1 | 1 | 3-Me | H | 3-Me | H | 3-Me | H |
| 14 | 1 | 1 | 4-Cl | H | 4-Cl | H | 4-Cl | H |
| 15 | 1 | 1 | 4-Cl | 4-Cl | 4-Cl | 4-Cl | 4-Cl | 4-Cl |
| 16 | 1 | 1 | 3-Me | 3-Me | 3-Me | 3-Me | 3-Me | 3-Me |
| 17 | 1 | 1 | 4-Me | 4-MeO | 4-Me | 4-MeO | 4-Me | 4-MeO |
| 18 | 1 | 1 | 3-Me | 4-MeO | 3-Me | 4-MeO | 3-Me | 4-MeO |
| 19 | 1 | 1 | 3-Me | 4-Cl | 3-Me | 4-Cl | 3-Me | 4-Cl |
| 20 | 1 | 1 | 4-Me | 4-Cl | 4-Me | 4-Cl | 4-Me | 4-Cl |

TABLE 2

| Exemplified Compound | m | n | R¹ | R² | R³ | R⁴ | R⁵ | R⁶ |
|---|---|---|---|---|---|---|---|---|
| 21 | 1 | 0 | H | H | H | H | H | H |
| 22 | 1 | 0 | 4-Me | 4-Me | 4-Me | 4-Me | 4-Me | 4-Me |
| 23 | 1 | 0 | 4-Me | 4-Me | H | H | 4-Me | 4-Me |
| 24 | 1 | 0 | H | H | 4-Me | 4-Me | H | H |
| 25 | 1 | 0 | H | H | 3-Me | 3-Me | H | H |
| 26 | 1 | 0 | H | H | 4-Cl | 4-Cl | H | H |
| 27 | 1 | 0 | 4-Me | H | H | H | 4-Me | H |
| 28 | 1 | 0 | 4-MeO | H | H | H | 4-MeO | H |
| 29 | 1 | 0 | H | H | 4-MeO | 4-MeO | H | H |
| 30 | 1 | 0 | 4-MeO | 4-MeO | 4-MeO | 4-MeO | 4-MeO | 4-MeO |
| 31 | 1 | 0 | 4-MeO | H | 4-MeO | H | 4-MeO | 4-MeO |
| 32 | 1 | 0 | 4-Me | H | 4-Me | H | 4-Me | 4-F |
| 33 | 1 | 0 | 3-Me | H | 3-Me | H | 3-Me | H |
| 34 | 1 | 0 | 4-Cl | H | 4-Cl | H | 4-Cl | H |
| 35 | 1 | 0 | 4-Cl | 4-Cl | 4-Cl | 4-Cl | 4-Cl | 4-Cl |
| 36 | 1 | 0 | 3-Me | 3-Me | 3-Me | 3-Me | 3-Me | 3-Me |
| 37 | 1 | 0 | 4-Me | 4-MeO | 4-Me | 4-MeO | 4-Me | 4-MeO |
| 38 | 1 | 0 | 3-Me | 4-MeO | 3-Me | 4-MeO | 3-Me | 4-MeO |
| 39 | 1 | 0 | 3-Me | 4-Cl | 3-Me | 4-Cl | 3-Me | 4-Cl |
| 40 | 1 | 0 | 4-Me | 4-Cl | 4-Me | 4-Cl | 4-Me | 4-Cl |

TABLE 3

| Exemplified Compound | m | n | R¹ | R² | R³ | R⁴ | R⁵ | R⁶ |
|---|---|---|---|---|---|---|---|---|
| 41 | 0 | 0 | H | H | H | H | H | H |
| 42 | 0 | 0 | 4-Me | 4-Me | 4-Me | 4-Me | 4-Me | 4-Me |
| 43 | 0 | 0 | 4-Me | 4-Me | 4-Me | 4-Me | H | H |
| 44 | 0 | 0 | 4-Me | H | 4-Me | H | H | H |
| 45 | 0 | 0 | H | H | H | H | 4-Me | 4-Me |
| 46 | 0 | 0 | 3-Me | 3-Me | 3-Me | 3-Me | H | H |
| 47 | 0 | 0 | H | H | H | H | 4-Cl | 4-Cl |
| 48 | 0 | 0 | 4-MeO | H | 4-MeO | H | H | H |
| 49 | 0 | 0 | H | H | H | H | 4-MeO | 4-MeO |
| 50 | 0 | 0 | 4-MeO | 4-MeO | 4-MeO | 4-MeO | 4-MeO | 4-MeO |
| 51 | 0 | 0 | 4-MeO | H | 4-MeO | H | 4-MeO | 4-MeO |
| 52 | 0 | 0 | 4-Me | H | 4-Me | H | 4-Me | 4-F |
| 53 | 0 | 0 | 3-Me | H | 3-Me | H | 3-Me | H |
| 54 | 0 | 0 | 4-Cl | H | 4-Cl | H | 4-Cl | H |
| 55 | 0 | 0 | 4-Cl | 4-Cl | 4-Cl | 4-Cl | 4-Cl | 4-Cl |
| 56 | 0 | 0 | 3-Me | 3-Me | 3-Me | 3-Me | 3-Me | 3-Me |
| 57 | 0 | 0 | 4-Me | 4-MeO | 4-Me | 4-MeO | 4-Me | 4-MeO |
| 58 | 0 | 0 | 3-Me | 4-MeO | 3-Me | 4-MeO | 3-Me | 4-MeO |
| 59 | 0 | 0 | 3-Me | 4-Cl | 3-Me | 4-Cl | 3-Me | 4-Cl |
| 60 | 0 | 0 | 4-Me | 4-Cl | 4-Me | 4-Cl | 4-Me | 4-Cl |

The abbreviations and symbols given in the tables have the following meanings.

4-Me: methyl substituent at the 4-position of phenyl
3-Me: methyl substituent at the 3-position of phenyl
4-Cl: chlorine atom substituent at the 4-position of phenyl
4-MeO: methoxy substituent at the 4-position of phenyl
4-F: fluorine atom substituent at the 4-position of phenyl The same also applies to the abbreviations and symbols used in the following compounds of this specification.

In the case where the compound of the present invention is represented by general formula (1) wherein m=n=1 and $(R^1, R^2)=(R^3, R^4)=(R^5, R^6)$, that is, $R^1$ and $R^2$ are the same as $R^3$ and $R^4$ and as $R^5$ and $R^6$, this triphenylamine derivative (1a) can be synthesized according to reaction scheme 1.

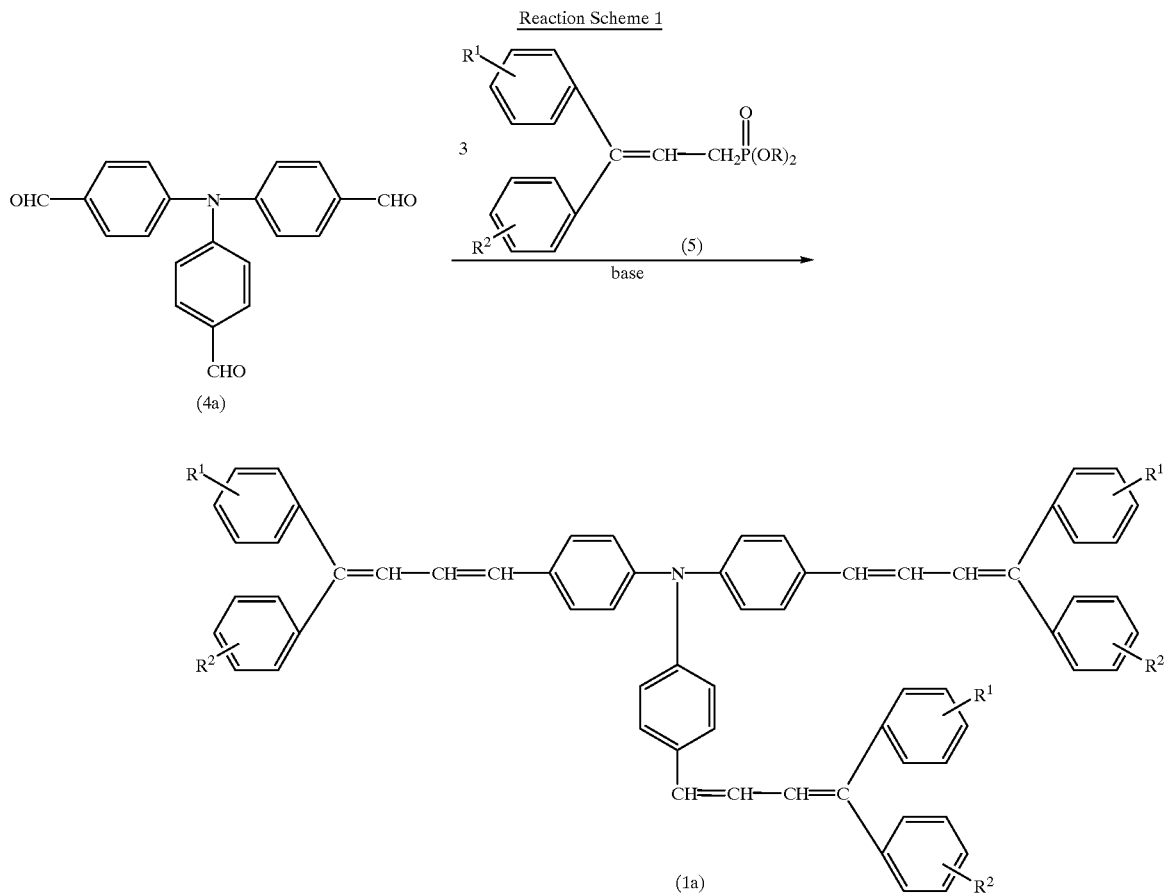

Reaction Scheme 1

(In the scheme, $R^1$, $R^2$ and R have the same meaning as defined above.)

It is especially desirable that R be methyl or ethyl.

That is, the desired compound can be easily produced by reacting 4,4',4"-triformyltriphenylamine (4a) with a 3,3-diarylallylphosphorous acid dialkyl ester (5) in an amount of at least 3 mol per mol of the compound (4a) in the presence of a base at a temperature between room temperature and around 80° C. Examples of the base include sodium hydroxide, sodium amide, and metal alkoxides, e.g., sodium methoxide, sodium tert-butoxide, and potassium tert-butoxide. As a solvent, use may be made of a lower alcohol, e.g., methanol or ethanol, an ether, e.g., 1,2-dimethoxyethane, diethyl ether, tetrahydrofuran, or dioxane, a hydrocarbon, e.g., toluene or xylene, an aprotic polar solvent, e.g., dimethyl sulfoxide, N,N-dimethylformamide, N,N-dimethylacetamide, or N-methylpyrrolidone, or a mixture thereof.

The preparation of the poly-formyl-substituted triphenylamine derivative represented by the foregoing general formula (4) to be used in the preparation of the novel triphenylamine derivative represented by the foregoing general formula (1) (foregoing reaction scheme 1) or to be an intermediate for the preparation of the compound (2) can be accomplished by a process which comprises allowing a triphenylamine derivative represented by the foregoing general formula (3) to react with a Vilsmeier reagent in the presence of an acid selected from the group consisting of Lewis acid and protonic acid, and then subjecting the reaction product to hydrolysis with an alkaline aqueous solution, as mentioned above. This reaction process will be further described below with reference to the following synthesis scheme (using as a Vilsmeier reagent one prepared from N,N-dimethylformamide and phosphorus oxychloride) by way of example:

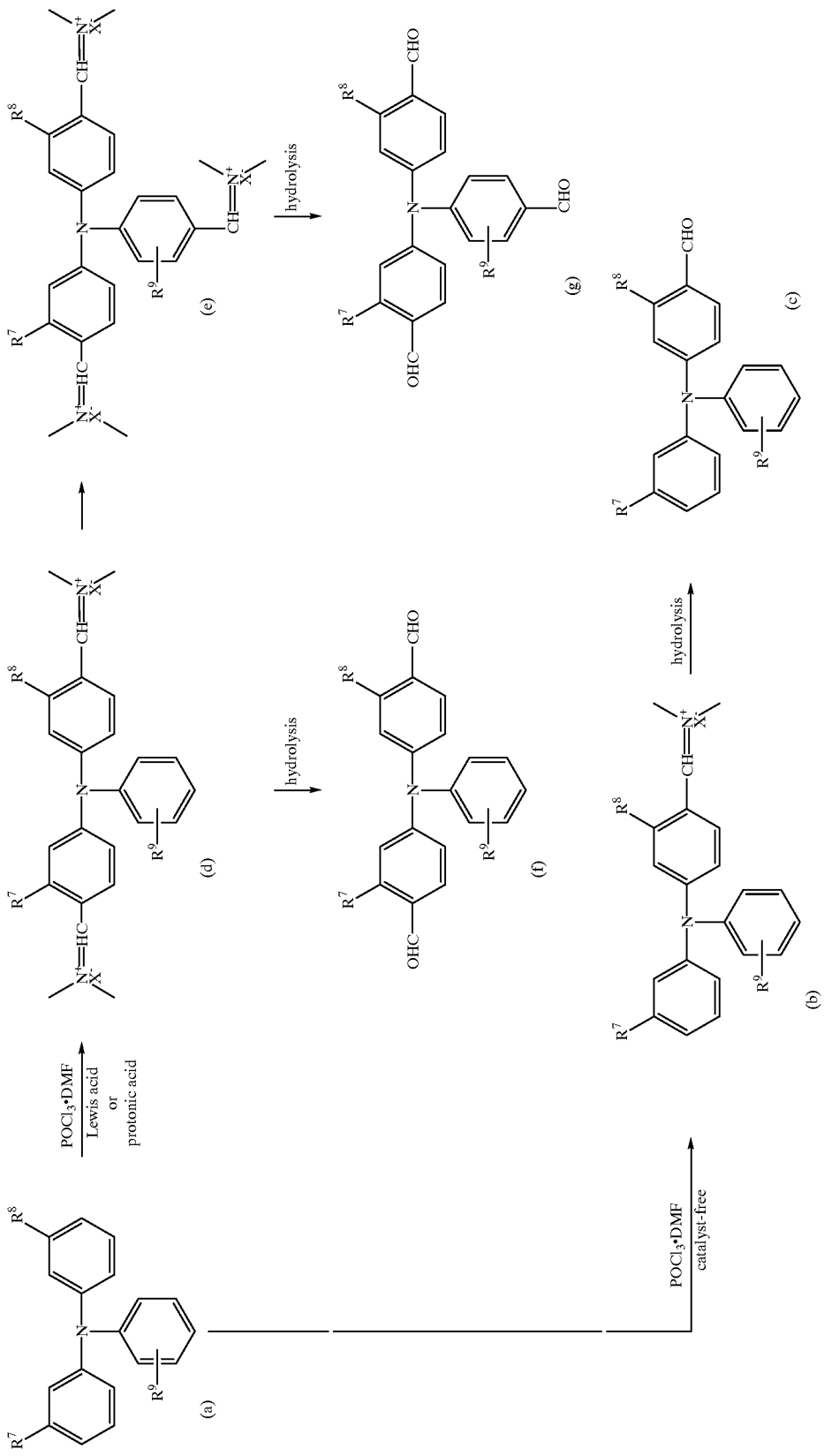

As can be seen in the foregoing reaction scheme, if the triphenylamine compound (a) is allowed to undergo Vilsmeier reaction in the absence of catalyst, the reaction almost terminates with a monoiminium salt (b). Accordingly, the majority of the resulting hydrolyzate is a mono-formyl-substituted compound (c). However, if the reaction is effected in the presence of a Lewis acid or protonic acid as a catalyst, it proceeds to produce a diiminium salt (d). Further, if an increased amount of the Vilsmeier reagent is used to elongate the reaction time, the reaction can lead to a triiminium salt (e). As a result, a di-formyl-substituted compound (f) and/or a tri-formyl-substituted compound (g) can be obtained singly or in admixture as a hydrolyzate.

The di-formyl-substituted compound (f) thus obtained is useful as an intermediate for the preparation of the compound included in the foregoing general formula (2) in the charge-transporting material of the present invention. Similarly, the tri-formyl-substituted compound (g) thus obtained is an intermediate for the preparation of the compound included in the foregoing general formula (1).

Therefore, both the tri-formyl-substituted compound (g) obtained according to the foregoing reaction and a mixture of the tri-formyl-substituted compound (g) and the di-formyl-substituted compound (f) are useful as an intermediate for the preparation of the compound to be incorporated in the charge-transporting material of the present invention.

Examples of the substituents $R^7$, $R^8$ and $R^9$ in the triphenylamine derivative (a) to be used as a raw material of the foregoing poly-formyl-substituted triphenylamine derivatives (f) and (g) include a hydrogen atom, a $C_{1-4}$ branched or straight-chain alkyl group, a lower alkoxy group such as methoxy group and ethoxy group, a phenoxy group, an aryl group which may have a substituent group such as phenyl group, o-tolyl group, m-tolyl group or p-tolyl group, and a halogen atom such as fluorine, chlorine, bromine and iodine. The substitution positions are meta-positions to amino group for $R^7$ and $R^8$ and ortho-, meta- and para-positions to amino group for $R^9$. In order to obtain the compounds (e) and (g), the substitution positions are preferably meta-positions to amino group.

Examples of N-substituted formamide to be a formylating agent include N,N-dimethylformamide, N-methylformanilide, N-formylmorpholine, and N,N-diisopropylformamide. Preferred among these N-substituted formamides are N,N-dimethylformamide and N-methylformanilide.

Examples of the halogenating reagent which reacts with such an N-substituted formamide to produce a Vilsmeier reagent include phosphorus oxychloride, phosgene, oxalyl chloride, thionyl chloride, triphenylphosphine-bromine complex, and hexachlorotriphosphur triene. Preferred among these halogenating reagents are phosphorus oxychloride, phosgene, and thionyl chloride.

As the solvent employable in the foregoing reaction there may be used one inactive to the reaction. Examples of such a solvent include hydrocarbon solvent such as toluene and xylene, chlorine solvent such as methylene chloride, 1,2-dichloroethane, chlorobenzene and dichlorobenzene, and ether solvent such as diethyl ether, diisopropyl ether and 1,4-dioxane. These solvents may be used in admixture.

The reaction can be carried out by a process which comprises weighing out 2 to 8 equivalents of N-substituted formamide in a solvent, adding 2 to 8 equivalents of a halogenating reagent dropwise to the solution to prepare a Vilsmeier reagent, adding 1 equivalent of a triphenylamine derivative to the Vilsmeier reagent, and then adding 1 or more equivalents of a Lewis acid or protonic acid. If it is desired to synthesize a di-formyl-substituted compound, the amount of N-substituted formylamide and halogenating reagent to be used each is preferably about 2 to 4 times that of triphenylamine. If it is desired to synthesize a tri-formyl-substituted compound, the amount of N-substituted formylamide and halogenating reagent to be used each is preferably about 5 to 7 times that of triphenylamine. The reaction suffices if the amount of the catalyst to be used is equal to or about twice that of triphenylamide. If the amount of the catalyst to be used falls below this range, the reaction proceeds insufficiently. On the contrary, if the amount of the catalyst to be used exceeds this range, it is economically disadvantageous. Alternatively, the reaction can be carried out by a process which comprises previously adding a catalyst, a triphenylamine derivative and an N-substituted formamide to a solvent, and then adding a halogenating reagent to the solution. The reaction may be effected at temperatures of from room temperature to 150° C., preferably from 50° C. to 90° C.

In order to synthesize the di-formyl-substituted compound, the reaction may be effected in the foregoing temperature range for 20 to 30 hours to obtain a diiminium salt of triphenylamine. In order to synthesize the tri-formyl-substituted compound, the reaction may further proceed for 40 to 60 hours in total to obtain a triiminium salt of triphenylamine. The iminium salt thus obtained can be then subjected to hydrolysis with an aqueous solution of an alkali such as sodium hydrogencarbonate, sodium carbonate, potassium carbonate, sodium hydroxide, potassium hydroxide and sodium acetate to lead to 4,4'-diformyltriphenylamine derivative or 4,4',4''-triformyltriphenylamine derivative.

The preparation process of the present invention enables the synthesis of 4,4'-diformyltriphenylamine derivative and 4,4',4''-triformyltriphenylamine derivative in a good yield. Since the foregoing reagents are relatively inexpensive, the preparation process of the present invention is industrially made possible.

Further, the 3,3-diarylallylphosphorous acid dialkyl ester (5) used for the above reaction scheme 1 can be obtained according to reaction scheme 3.

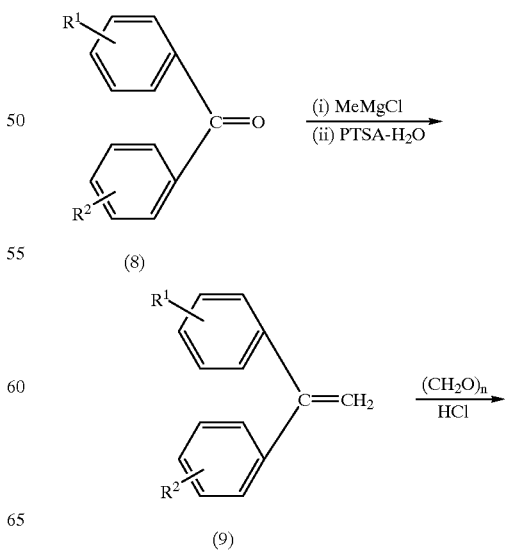

Reaction Scheme 3

Reaction Scheme 4

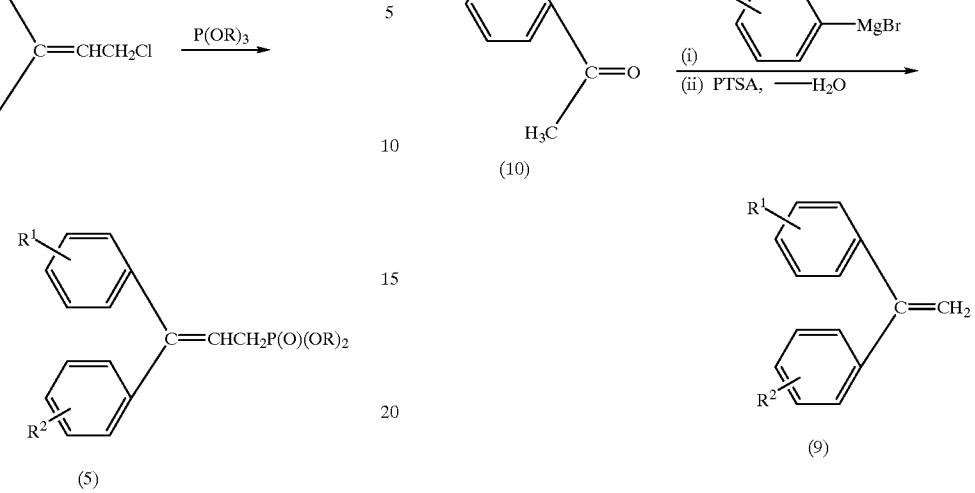

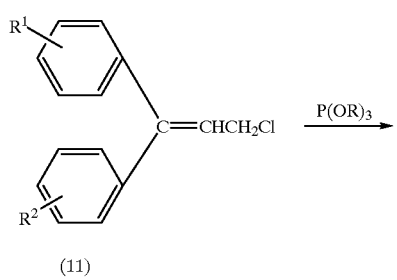

(5)

That is, a 1,1-diarylethylene (9) is first obtained by (i) reacting a benzophenone derivative (8) with methylmagnesium chloride (MeMgCl) and then (ii) dehydrating the resulting alcohol in the presence of an acid. Usable as the acid is one ordinarily used for dehydration reaction, such as, e.g., PTSA (p-toluenesulfonic acid).

The 1,1-diarylethylene (9) can be obtained also by conducting the same reactions (i) and (ii) described above, except that an acetophenone derivative (10) is used as a starting compound and a substituted phenylmagnesium bromide is used in place of methylmagnesium chloride according to reaction scheme 4.

Subsequently, the 1,1-diarylethylene (9) is reacted with paraformaldehyde $(CH_2O)_n$ and hydrogen chloride in acetic acid according to the method described in JP-A-49-75564 to obtain a 3,3-diarylallyl chloride (11). This 3,3-diarylallyl chloride (11) is reacted with a trialkyl phosphite $P(OR)_3$, whereby the 3,3-diarylallylphosphorous acid dialkyl ester (5) can be obtained.

Examples of the trialkyl phosphite include trimethyl phosphite, triethyl phosphite, tripropyl phosphite, and tributyl phosphite.

In the case where the compound of the present invention is represented by general formula (1) wherein m=n=1 and $(R^1, R^2)=(R^5, R^6)\neq(R^3, R^4)$, that is, $R^1$ and $R^2$ are the same as $R^5$ and $R^6$ but different from $R^3$ and $R^4$, this triphenylamine derivative (1b) can be synthesized according to reaction scheme 5.

Reaction Scheme 5

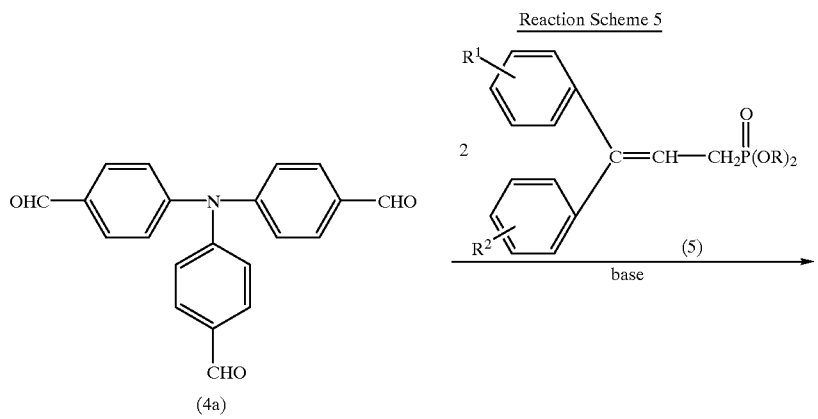

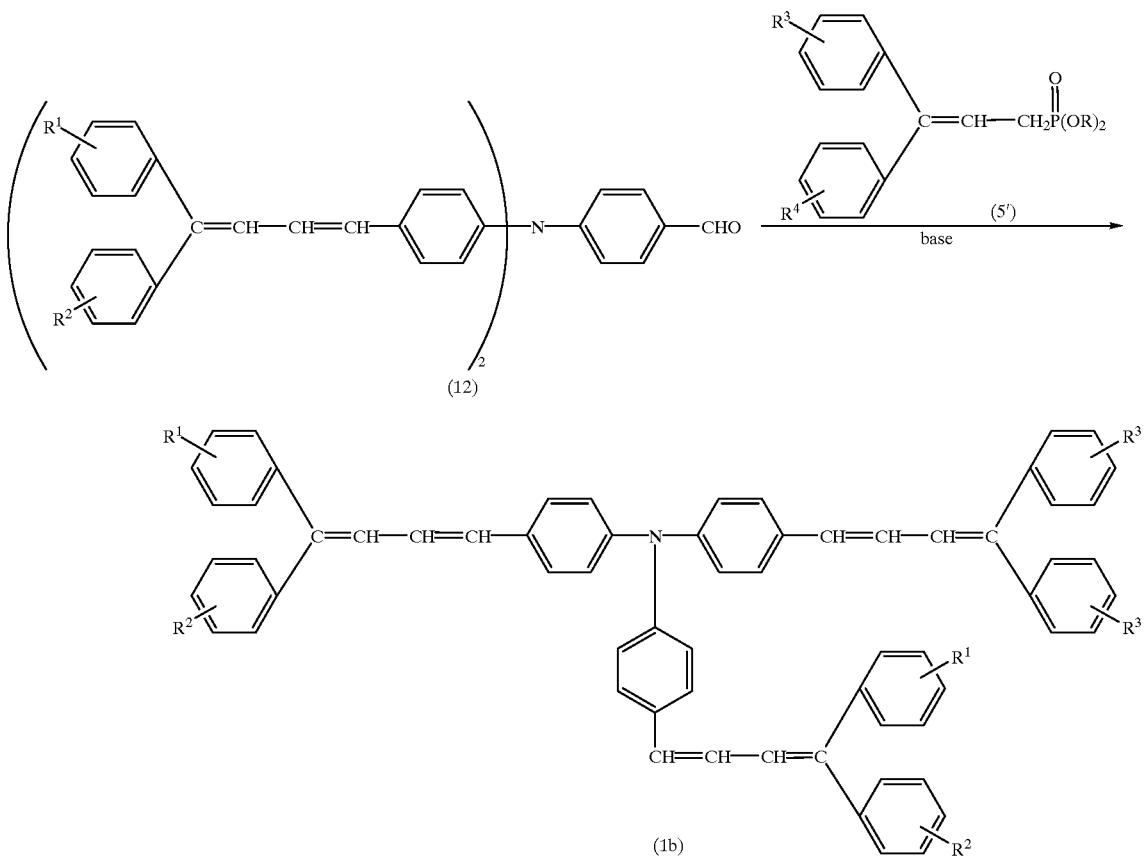

4,4',4"-Triformyltriphenylamine (4a) is reacted with a 3,3-diarylallylphosphorous acid trialkyl ester (5) in an amount of 2 mol per mol of the compound (4a) in the presence of a base to synthesize a 4,4'-bis(4''',4''''-diaryl-1''', 3'''-butadienyl)-4"-formyltriphenylamine (12). This compound (12) is reacted with a 3,3-diarylallylphosphorous acid dialkyl ester (5') different from the compound (5), whereby the desired compound (1b) of the present invention can be synthesized.

In the case where the compound of the present invention is represented by general formula (1) wherein m=1, n=0, and $(R^1, R^2)=(R^5, R^6)\neq(R^3, R^4)$, this triphenylamine derivative (1c) can be synthesized according to reaction scheme 6.

Reaction Scheme 6

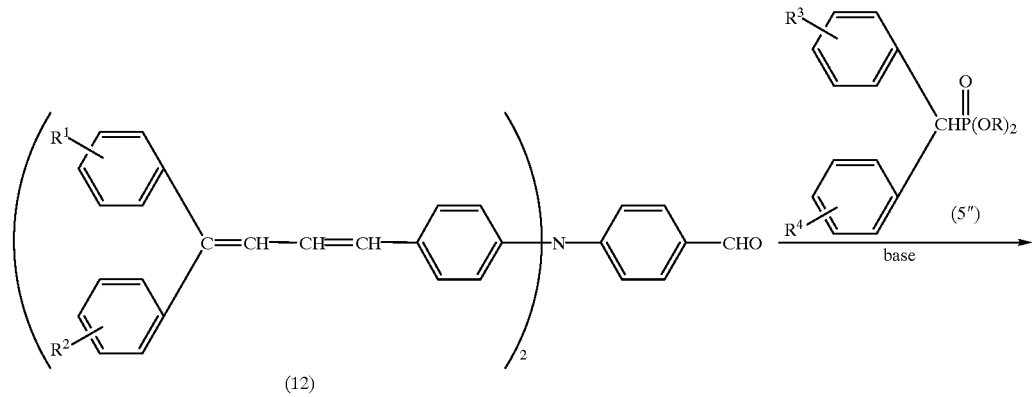

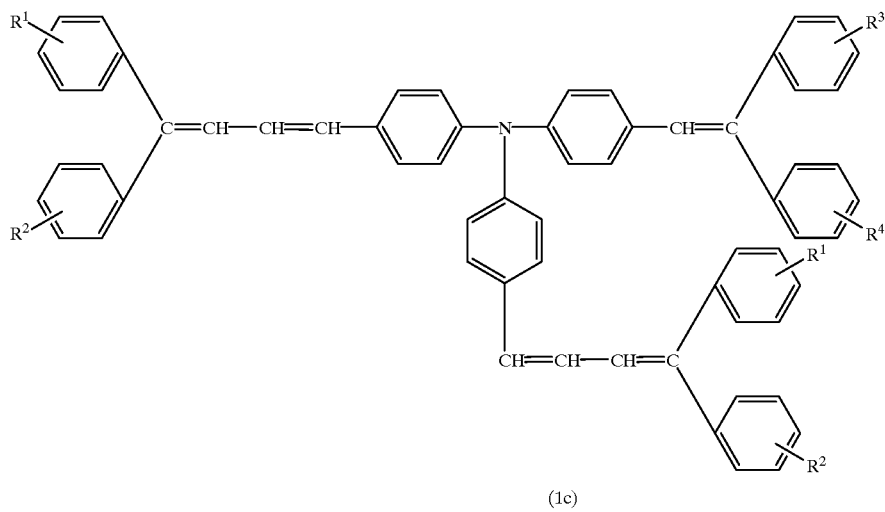

(1c)

That is, the 4,4'-bis(4'",4'"-diaryl-1'",3'"-butadienyl)-4"-formyltriphenylamine (12) shown in reaction scheme 5 given above is reacted with an equimolar amount of a diarylmethylphosphorous acid dialkyl ester (5"), whereby the desired compound (1c) of the present invention can be synthesized.

The diarylmethylphosphorous acid dialkyl ester (5") is obtained from the corresponding diarylmethyl chloride or bromide and the corresponding trialkyl phosphite by heating these compounds either directly or in a solvent such as, e.g., toluene or xylene.

In the case where the compound of the present invention is represented by general formula (1) wherein $m=n=0$ and $(R^1, R^2)=(R^3,R^4)\neq(R^5, R^6)$, this triphenylamine derivative (1d) can be synthesized according to reaction scheme 7.

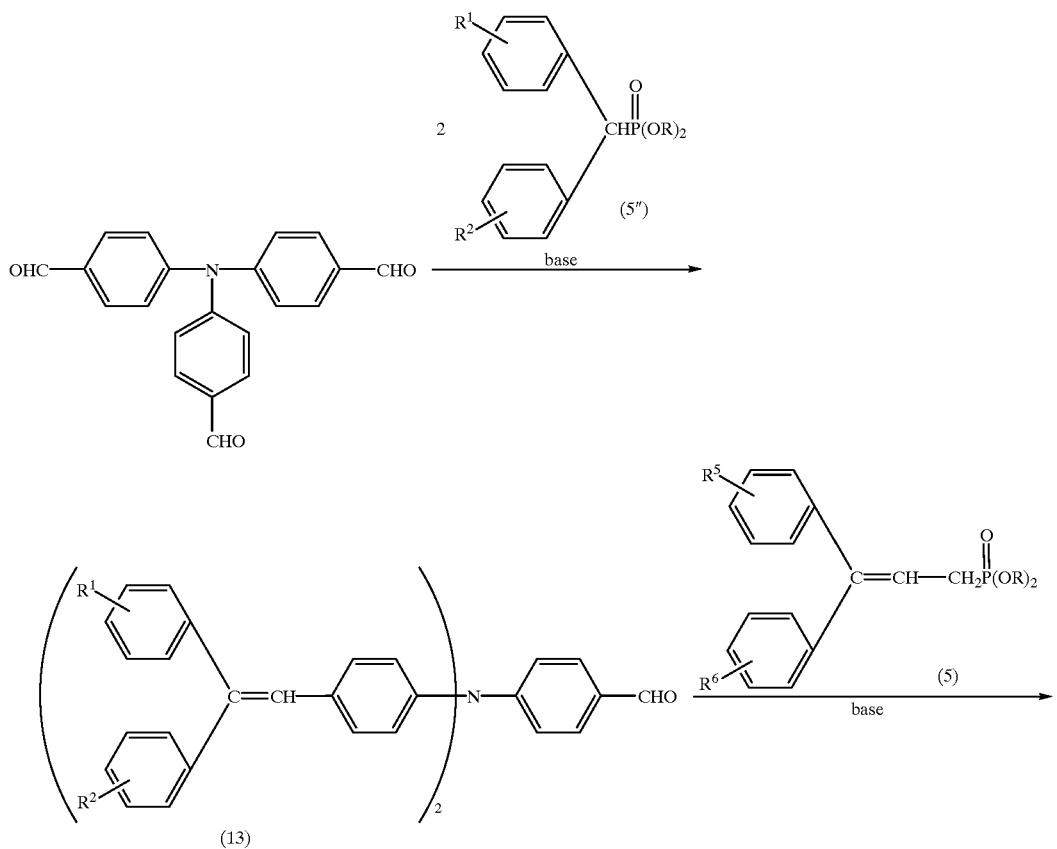

Reaction Scheme 7

-continued

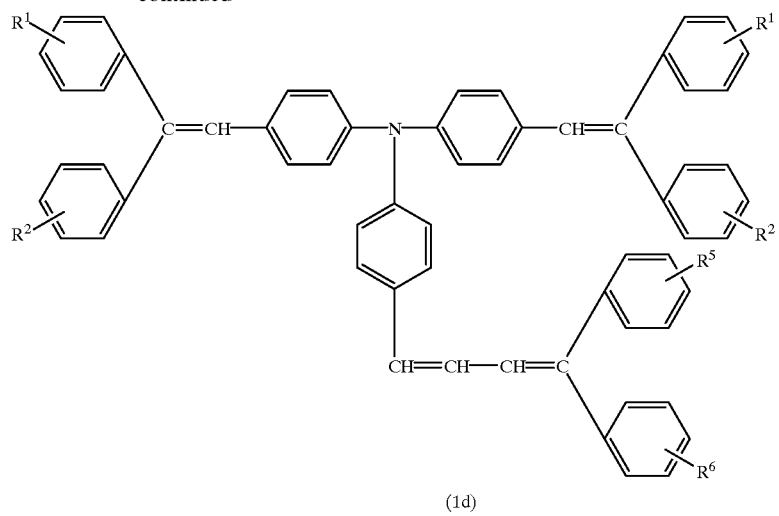

(1d)

4,4',4''-Triformyltriphenylamine (4a) is reacted with a diarylmethylphosphorous acid dialkyl ester (5'') in an amount of 2 mol per mol of the compound (4a) in the presence of a base to synthesize a 4,4'-bis(2''',2'''-diarylvinyl)-4''-formyltriphenylamine (13). This compound (13) is reacted with a 3,3-diarylallylphosphorous acid dialkyl ester (5), whereby the desired compound (1d) of the present invention can be synthesized.

Specific examples of the triphenylamine derivative represented by the following general formula (2):

include lower alkyl-substituted phenyl group such as phenyl, p-tolyl and 2,4-dimethylphenyl, lower alkoxy-substituted phenyl group such as p-methoxyphenyl, and halogen-substituted phenyl group such as p-chlorophenyl.

The triphenylamine derivative represented by the general formula (2) can be prepared by a reaction process similar to the foregoing reaction schemes 1 to 7 described as process for the preparation of the triphenylamine derivative represented by the foregoing general formula (1).

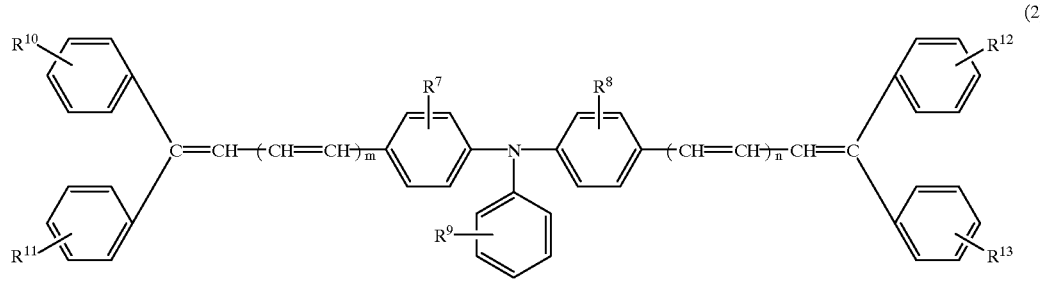

(2)

wherein $R^7$ to $R^{13}$ may be the same or different and each represents a hydrogen atom, a lower alkyl group, an alkoxy group, a phenoxy group, a halogen atom or an aryl group which may have a substituent group; and m and n each represents 0 or 1, to be mixed with the novel triphenylamine derivative represented by the foregoing general formula (1) as a charge-transporting material of the present invention are set forth in Tables 4 to 6 below, but the present invention should not be limited thereto.

Preferred examples of the lower alkyl group represented by $R^7$ to $R^{13}$ in the foregoing general formula (2) include $C_{1-4}$ alkyl groups such as methyl, ethyl, n-propyl, isopropyl, n-butyl, sec-butyl and isobutyl. Particularly preferred among these alkyl groups are methyl group and ethyl group. Examples of the alkoxy group represented by $R^7$ to $R^{13}$ include $C_{1-4}$ alkoxy groups such as methoxy, ethoxy, propoxy and butoxy. Examples of the halogen atom represented by $R^7$ to $R^{13}$ include fluorine atom, chlorine atom, bromine atom, and iodine atom. Examples of the alkyl group which may have a substituent group represented by $R^7$ to $R^{13}$

TABLE 4

(Formula (2))

| | m | n | $R^7$ | $R^8$ | $R^9$ | $R^{10}$ | $R^{11}$ | $R^{12}$ | $R^{13}$ |
|---|---|---|---|---|---|---|---|---|---|
| (2)-1 | 0 | 0 | H | H | H | H | H | H | H |
| (2)-2 | 0 | 0 | H | H | H | 4-Me | 4-Me | 4-Me | 4-Me |
| (2)-3 | 0 | 0 | H | 3-Me | H | H | H | 4-Me | 4-Me |
| (2)-4 | 0 | 0 | H | H | H | 4-Me | H | 4-Me | H |
| (2)-5 | 0 | 0 | H | H | H | 3-Me | H | 3-Me | H |
| (2)-6 | 0 | 0 | H | H | H | H | H | 4-Cl | 4-Cl |
| (2)-7 | 0 | 0 | H | H | 4-Me | H | H | H | H |
| (2)-8 | 0 | 0 | H | H | 4-Me | 4-Me | 4-Me | 4-Me | 4-Me |
| (2)-9 | 0 | 0 | 3-Me | 3-Me | 4-Me | 4-Me | H | 4-Me | 4-Me |
| (2)-10 | 0 | 0 | H | H | 4-Me | 4-Me | H | 4-Me | H |
| (2)-11 | 0 | 0 | H | H | 4-Me | 3-Me | H | 3-Me | H |
| (2)-12 | 0 | 0 | H | H | 4-Me | H | H | 4-Cl | 4-Cl |
| (2)-13 | 0 | 0 | H | H | 2-Me | H | H | H | H |
| (2)-14 | 0 | 0 | H | H | 2-Me | 4-Me | 4-Me | 4-Me | 4-Me |
| (2)-15 | 0 | 0 | H | H | 2-Me | H | H | 4-Me | 4-Me |

TABLE 4-continued (Formula (2))

| | m | n | R⁷ | R⁸ | R⁹ | R¹⁰ | R¹¹ | R¹² | R¹³ |
|---|---|---|---|---|---|---|---|---|---|
| (2)-16 | 0 | 0 | H | H | 2-Me | 4-Me | H | 4-Me | H |
| (2)-17 | 0 | 0 | H | 3-MeO | 2-Me | 3-Me | H | 3-Me | H |
| (2)-18 | 0 | 0 | H | H | 2-Me | H | H | 4-Cl | 4-Cl |
| (2)-19 | 0 | 0 | H | H | 4-MeO | H | H | H | H |
| (2)-20 | 0 | 0 | H | H | 4-MeO | 4-Me | 4-Me | 4-Me | 4-Me |
| (2)-21 | 0 | 0 | H | H | 4-MeO | H | H | 4-Me | 4-Me |
| (2)-22 | 0 | 0 | H | H | 4-MeO | 4-Me | H | 4-Me | H |
| (2)-23 | 0 | 0 | H | H | 4-MeO | 3-Me | H | 3-Me | H |
| (2)-24 | 0 | 0 | H | H | 4-MeO | H | H | 4-Cl | 4-Cl |
| (2)-25 | 0 | 0 | H | H | 4-Br | 4-Me | 4-Me | 4-Me | 4-Me |
| (2)-26 | 0 | 0 | H | H | 4-Br | 4-Me | H | 4-Me | H |
| (2)-27 | 0 | 0 | H | H | 4-Br | 4-F | 4-F | 4-F | 4-F |
| (2)-28 | 0 | 0 | H | H | 4-Br | H | H | H | H |

TABLE 5

| | m | n | R⁷ | R⁸ | R⁹ | R¹⁰ | R¹¹ | R¹² | R¹³ |
|---|---|---|---|---|---|---|---|---|---|
| (2)-29 | 1 | 0 | H | H | H | H | H | H | H |
| (2)-30 | 1 | 0 | H | H | H | 4-Me | 4-Me | 4-Me | 4-Me |
| (2)-31 | 1 | 0 | H | 3-Me | H | H | H | 4-Me | 4-Me |
| (2)-32 | 1 | 0 | H | H | H | 4-Me | H | 4-Me | H |
| (2)-33 | 1 | 0 | H | H | H | 4-Me | 4-Me | H | H |
| (2)-34 | 1 | 0 | H | H | H | H | H | 4-Cl | 4-Cl |
| (2)-35 | 1 | 0 | H | H | 4-Me | H | H | H | H |
| (2)-36 | 1 | 0 | H | H | 4-Me | 4-Me | 4-Me | 4-Me | 4-Me |
| (2)-37 | 1 | 0 | 3-Me | 3-Me | 4-Me | H | H | 4-Me | 4-Me |
| (2)-38 | 1 | 0 | H | H | 4-Me | 4-Me | H | 4-Me | H |
| (2)-39 | 1 | 0 | H | H | 4-Me | 3-Me | H | 3-Me | H |
| (2)-40 | 1 | 0 | H | H | 4-Me | H | H | 4-Cl | 4-Cl |
| (2)-41 | 1 | 0 | H | H | 2-Me | H | H | H | H |
| (2)-42 | 1 | 0 | H | H | 2-Me | 4-Me | 4-Me | 4-Me | 4-Me |
| (2)-43 | 1 | 0 | H | H | 2-Me | H | H | 4-Me | 4-Me |
| (2)-44 | 1 | 0 | H | H | 2-Me | 4-Me | H | 4-Me | H |
| (2)-45 | 1 | 0 | H | 3-MeO | 2-Me | 3-Me | H | 3-Me | H |
| (2)-46 | 1 | 0 | H | H | 2-Me | H | H | 4-Cl | 4-Cl |
| (2)-47 | 1 | 0 | H | H | 4-MeO | H | H | H | H |
| (2)-48 | 1 | 0 | H | H | 4-MeO | 4-Me | 4-Me | 4-Me | 4-Me |
| (2)-49 | 1 | 0 | H | H | 4-MeO | H | H | 4-Me | 4-Me |
| (2)-50 | 1 | 0 | H | H | 4-MeO | 4-Me | H | 4-Me | H |
| (2)-51 | 1 | 0 | H | H | 4-MeO | 3-Me | H | 3-Me | H |
| (2)-52 | 1 | 0 | H | H | 4-MeO | H | H | 4-Cl | 4-Cl |
| (2)-53 | 1 | 0 | H | H | 4-Br | 4-Me | 4-Me | 4-Me | 4-Me |
| (2)-54 | 1 | 0 | H | H | 4-Br | 4-Me | H | 4-Me | H |
| (2)-55 | 1 | 0 | H | H | 4-Br | 4-F | 4-F | 4-F | 4-F |
| (2)-56 | 1 | 0 | H | H | 4-Br | H | H | H | H |

TABLE 6

| | m | n | R⁷ | R⁸ | R⁹ | R¹⁰ | R¹¹ | R¹² | R¹³ |
|---|---|---|---|---|---|---|---|---|---|
| (2)-57 | 1 | 1 | H | H | H | H | H | H | H |
| (2)-58 | 1 | 1 | H | H | H | 4-Me | 4-Me | 4-Me | 4-Me |
| (2)-59 | 1 | 1 | H | 3-Me | H | H | H | 4-Me | 4-Me |
| (2)-60 | 1 | 1 | H | H | H | 4-Me | H | 4-Me | H |
| (2)-61 | 1 | 1 | H | H | H | 3-Me | H | 3-Me | H |
| (2)-62 | 1 | 1 | H | H | H | H | H | 4-Cl | 4-Cl |
| (2)-63 | 1 | 1 | H | H | 4-Me | H | H | H | H |
| (2)-64 | 1 | 1 | H | H | 4-Me | 4-Me | 4-Me | 4-Me | 4-Me |

TABLE 6-continued

| | m | n | R⁷ | R⁸ | R⁹ | R¹⁰ | R¹¹ | R¹² | R¹³ |
|---|---|---|---|---|---|---|---|---|---|
| (2)-65 | 1 | 1 | 3-Me | 3-Me | 4-Me | H | H | 4-Me | 4-Me |
| (2)-66 | 1 | 1 | H | H | 4-Me | 4-Me | H | 4-Me | H |
| (2)-67 | 1 | 1 | H | H | 4-Me | 3-Me | H | 3-Me | H |
| (2)-68 | 1 | 1 | H | H | 4-Me | H | H | 4-Cl | 4-Cl |
| (2)-69 | 1 | 1 | H | H | 2-Me | H | H | H | H |
| (2)-70 | 1 | 1 | H | H | 2-Me | 4-Me | 4-Me | 4-Me | 4-Me |
| (2)-71 | 1 | 1 | H | H | 2-Me | H | H | 4-Me | 4-Me |
| (2)-72 | 1 | 1 | H | H | 2-Me | 4-Me | H | 4-Me | H |
| (2)-73 | 1 | 1 | H | 3-MeO | 2-Me | 3-Me | H | 3-Me | H |
| (2)-74 | 1 | 1 | H | H | 2-Me | H | H | 4-Cl | 4-Cl |
| (2)-75 | 1 | 1 | H | H | 4-MeO | H | H | H | H |
| (2)-76 | 1 | 1 | H | H | 4-MeO | 4-Me | 4-Me | 4-Me | 4-Me |
| (2)-77 | 1 | 1 | H | H | 4-MeO | H | H | 4-Me | 4-Me |
| (2)-78 | 1 | 1 | H | H | 4-MeO | 4-Me | H | 4-Me | H |
| (2)-79 | 1 | 1 | H | H | 4-MeO | 3-Me | H | 3-Me | H |
| (2)-80 | 1 | 1 | H | H | 4-MeO | H | H | 4-Cl | 4-Cl |
| (2)-81 | 1 | 1 | H | H | 4-Br | 4-Me | 4-Me | 4-Me | 4-Me |
| (2)-82 | 1 | 1 | H | H | 4-Br | 4-Me | H | 4-Me | H |
| (2)-83 | 1 | 1 | H | H | 4-Br | 4-F | 4-F | 4-F | 4-F |
| (2)-84 | 1 | 1 | H | H | 4-Br | H | H | H | H |

The process for the preparation of a mixture of the triphenylamine derivative represented by the foregoing general formula (1) and the triphenylamine derivative represented by the general formula (2) which can be incorporated in the charge-transporting material of the present invention is not specifically limited. The two triphenylamine derivatives of the general formulae (1) and (2) which have been separately prepared according to the foregoing reaction schemes 1 to 7, etc. may be mixed.

If the poly-formyl-substituted triphenylamine derivative intermediate represented by the foregoing general formula (4) produced in the process for the preparation of the novel triphenylamine derivative represented by the general formula (1) is obtained in the form of a mixture of a di-formyl-substituted triphenylamine derivative represented by the general formula (4) wherein the substituent Y is a hydrogen atom and a tri-formyl-substituted triphenylamine derivative represented by the general formula (4) wherein the substituent Y is a formyl group, the intermediate mixture may be directly reacted with a phosphorous acid ester compound represented by the foregoing general formula (5) to prepare a mixture of two triphenylamine derivatives represented by the foregoing general formulae (1) and (2). Alternatively, other preparation processes which can prepare a mixture of the two triphenylamine derivatives can be employed.

If the compound represented by the general formula (1) and the compound represented by the general formula (2) are mixed to prepare a charge-transporting material of the present invention, combinations set forth in Tables 7 to 10 may be used, but the present invention should not be limited thereto.

TABLE 7

| No. of Formula (1) | No. of Formula (2) | No. of Formula (1) | No. of Formula (2) | No. of Formula (1) | No. of Formula (2) | No. of Formula (1) | No. of Formula (2) | No. of Formula (1) | No. of Formula (2) | No. of Formula (1) | No. of Formula (2) |
|---|---|---|---|---|---|---|---|---|---|---|---|
| 1 | (2)-1  | 2 | (2)-1  | 3 | (2)-1  | 4 | (2)-1  | 5 | (2)-1  | 8 | (2)-1  |
| 1 | (2)-2  | 2 | (2)-2  | 3 | (2)-2  | 4 | (2)-2  | 5 | (2)-2  | 8 | (2)-2  |
| 1 | (2)-7  | 2 | (2)-7  | 3 | (2)-7  | 4 | (2)-7  | 5 | (2)-7  | 8 | (2)-7  |
| 1 | (2)-8  | 2 | (2)-8  | 3 | (2)-8  | 4 | (2)-8  | 5 | (2)-8  | 8 | (2)-8  |
| 1 | (2)-13 | 2 | (2)-13 | 3 | (2)-13 | 4 | (2)-13 | 5 | (2)-13 | 8 | (2)-13 |
| 1 | (2)-14 | 2 | (2)-14 | 3 | (2)-14 | 4 | (2)-14 | 5 | (2)-14 | 8 | (2)-14 |
| 1 | (2)-19 | 2 | (2)-19 | 3 | (2)-19 | 4 | (2)-19 | 5 | (2)-19 | 8 | (2)-19 |
| 1 | (2)-20 | 2 | (2)-20 | 3 | (2)-20 | 4 | (2)-20 | 5 | (2)-20 | 8 | (2)-20 |
| 1 | (2)-25 | 2 | (2)-25 | 3 | (2)-25 | 4 | (2)-25 | 5 | (2)-25 | 8 | (2)-25 |
| 1 | (2)-28 | 2 | (2)-28 | 3 | (2)-28 | 4 | (2)-28 | 5 | (2)-28 | 8 | (2)-28 |
| 1 | (2)-29 | 2 | (2)-29 | 3 | (2)-29 | 4 | (2)-29 | 5 | (2)-29 | 8 | (2)-29 |
| 1 | (2)-30 | 2 | (2)-30 | 3 | (2)-30 | 4 | (2)-30 | 5 | (2)-30 | 8 | (2)-30 |
| 1 | (2)-35 | 2 | (2)-35 | 3 | (2)-35 | 4 | (2)-35 | 5 | (2)-35 | 8 | (2)-35 |
| 1 | (2)-36 | 2 | (2)-36 | 3 | (2)-36 | 4 | (2)-36 | 5 | (2)-36 | 8 | (2)-36 |

TABLE 8

| No. of Formula (1) | No. of Formula (2) | No. of Formula (1) | No. of Formula (2) | No. of Formula (1) | No. of Formula (2) | No. of Formula (1) | No. of Formula (2) | No. of Formula (1) | No. of Formula (2) | No. of Formula (1) | No. of Formula (2) |
|---|---|---|---|---|---|---|---|---|---|---|---|
| 1 | (2)-44 | 2 | (2)-44 | 3 | (2)-44 | 4 | (2)-44 | 5 | (2)-44 | 8 | (2)-44 |
| 1 | (2)-47 | 2 | (2)-47 | 3 | (2)-47 | 4 | (2)-47 | 5 | (2)-47 | 8 | (2)-47 |
| 1 | (2)-48 | 2 | (2)-48 | 3 | (2)-48 | 4 | (2)-48 | 5 | (2)-48 | 8 | (2)-48 |
| 1 | (2)-53 | 2 | (2)-53 | 3 | (2)-53 | 4 | (2)-53 | 6 | (2)-53 | 9 | (2)-53 |
| 1 | (2)-56 | 2 | (2)-56 | 3 | (2)-56 | 4 | (2)-56 | 6 | (2)-56 | 9 | (2)-56 |
| 1 | (2)-57 | 2 | (2)-57 | 3 | (2)-57 | 4 | (2)-57 | 6 | (2)-57 | 9 | (2)-57 |
| 1 | (2)-58 | 2 | (2)-58 | 3 | (2)-58 | 4 | (2)-58 | 6 | (2)-58 | 9 | (2)-58 |
| 1 | (2)-63 | 2 | (2)-63 | 3 | (2)-63 | 4 | (2)-63 | 6 | (2)-63 | 9 | (2)-63 |
| 1 | (2)-64 | 2 | (2)-64 | 3 | (2)-64 | 4 | (2)-64 | 6 | (2)-64 | 9 | (2)-64 |
| 1 | (2)-66 | 2 | (2)-66 | 3 | (2)-66 | 4 | (2)-66 | 6 | (2)-66 | 9 | (2)-66 |
| 1 | (2)-69 | 2 | (2)-69 | 3 | (2)-69 | 4 | (2)-69 | 6 | (2)-69 | 9 | (2)-69 |
| 1 | (2)-70 | 2 | (2)-70 | 3 | (2)-70 | 4 | (2)-70 | 6 | (2)-70 | 9 | (2)-70 |
| 1 | (2)-75 | 2 | (2)-75 | 3 | (2)-75 | 4 | (2)-75 | 6 | (2)-75 | 9 | (2)-75 |
| 1 | (2)-76 | 2 | (2)-76 | 3 | (2)-76 | 4 | (2)-76 | 6 | (2)-76 | 9 | (2)-76 |
| 1 | (2)-81 | 2 | (2)-81 | 3 | (2)-81 | 4 | (2)-81 | 6 | (2)-81 | 9 | (2)-81 |

TABLE 9

| No. of Formula (1) | No. of Formula (2) | No. of Formula (1) | No. of Formula (2) | No. of Formula (1) | No. of Formula (2) | No. of Formula (1) | No. of Formula (2) | No. of Formula (1) | No. of Formula (2) | No. of Formula (1) | No. of Formula (2) |
|---|---|---|---|---|---|---|---|---|---|---|---|
| 21 | (2)-1  | 22 | (2)-1  | 23 | (2)-1  | 24 | (2)-1  | 41 | (2)-1  | 42 | (2)-1  |
| 21 | (2)-2  | 22 | (2)-2  | 23 | (2)-2  | 24 | (2)-2  | 41 | (2)-2  | 42 | (2)-2  |
| 21 | (2)-7  | 22 | (2)-7  | 23 | (2)-7  | 24 | (2)-7  | 41 | (2)-7  | 42 | (2)-7  |
| 21 | (2)-8  | 22 | (2)-8  | 23 | (2)-8  | 24 | (2)-8  | 41 | (2)-8  | 42 | (2)-8  |
| 21 | (2)-13 | 22 | (2)-13 | 23 | (2)-13 | 24 | (2)-13 | 41 | (2)-13 | 42 | (2)-13 |
| 21 | (2)-14 | 22 | (2)-14 | 23 | (2)-14 | 24 | (2)-14 | 41 | (2)-14 | 42 | (2)-14 |
| 21 | (2)-19 | 22 | (2)-19 | 23 | (2)-19 | 24 | (2)-19 | 41 | (2)-19 | 42 | (2)-19 |
| 21 | (2)-20 | 22 | (2)-20 | 23 | (2)-20 | 24 | (2)-20 | 41 | (2)-20 | 42 | (2)-20 |
| 21 | (2)-25 | 22 | (2)-25 | 23 | (2)-25 | 24 | (2)-25 | 41 | (2)-25 | 42 | (2)-25 |
| 21 | (2)-28 | 22 | (2)-28 | 23 | (2)-28 | 24 | (2)-28 | 41 | (2)-28 | 42 | (2)-28 |
| 21 | (2)-29 | 22 | (2)-29 | 23 | (2)-29 | 24 | (2)-29 | 41 | (2)-29 | 42 | (2)-29 |
| 21 | (2)-30 | 22 | (2)-30 | 23 | (2)-30 | 24 | (2)-30 | 41 | (2)-30 | 42 | (2)-30 |
| 21 | (2)-35 | 22 | (2)-35 | 23 | (2)-35 | 24 | (2)-35 | 41 | (2)-35 | 42 | (2)-35 |
| 21 | (2)-36 | 22 | (2)-36 | 23 | (2)-36 | 24 | (2)-36 | 41 | (2)-36 | 42 | (2)-36 |
| 21 | (2)-44 | 22 | (2)-42 | 23 | (2)-42 | 24 | (2)-42 | 41 | (2)-42 | 43 | (2)-42 |
| 21 | (2)-47 |    |        |    |        |    |        |    |        |    |        |

TABLE 10

| No. of Formula (1) | No. of Formula (2) | No. of Formula (1) | No. of Formula (2) | No. of Formula (1) | No. of Formula (2) | No. of Formula (1) | No. of Formula (2) | No. of Formula (1) | No. of Formula (2) | No. of Formula (1) | No. of Formula (2) |
|---|---|---|---|---|---|---|---|---|---|---|---|
| 21 | (2)-48 | 22 | (2)-44 | 23 | (2)-44 | 24 | (2)-44 | 41 | (2)-44 | 43 | (2)-44 |
| 21 | (2)-53 | 22 | (2)-47 | 23 | (2)-47 | 24 | (2)-47 | 41 | (2)-47 | 43 | (2)-47 |
| 21 | (2)-35 | 22 | (2)-48 | 23 | (2)-48 | 24 | (2)-48 | 41 | (2)-48 | 43 | (2)-48 |
| 21 | (2)-56 | 22 | (2)-53 | 23 | (2)-53 | 24 | (2)-53 | 41 | (2)-53 | 43 | (2)-53 |
| 21 | (2)-57 | 22 | (2)-56 | 23 | (2)-56 | 24 | (2)-56 | 41 | (2)-56 | 43 | (2)-56 |
| 21 | (2)-58 | 22 | (2)-57 | 23 | (2)-57 | 24 | (2)-57 | 41 | (2)-57 | 43 | (2)-57 |
| 21 | (2)-63 | 22 | (2)-58 | 23 | (2)-58 | 24 | (2)-58 | 41 | (2)-58 | 43 | (2)-58 |
| 21 | (2)-64 | 22 | (2)-63 | 23 | (2)-63 | 24 | (2)-63 | 41 | (2)-63 | 43 | (2)-63 |
| 21 | (2)-66 | 22 | (2)-64 | 23 | (2)-64 | 24 | (2)-64 | 41 | (2)-64 | 43 | (2)-64 |
| 21 | (2)-69 | 22 | (2)-66 | 23 | (2)-66 | 24 | (2)-66 | 41 | (2)-66 | 43 | (2)-66 |
| 21 | (2)-70 | 22 | (2)-69 | 23 | (2)-69 | 24 | (2)-69 | 41 | (2)-69 | 43 | (2)-69 |
| 21 | (2)-75 | 22 | (2)-70 | 23 | (2)-70 | 24 | (2)-70 | 41 | (2)-70 | 43 | (2)-70 |
| 21 | (2)-76 | 22 | (2)-75 | 23 | (2)-75 | 24 | (2)-75 | 41 | (2)-75 | 43 | (2)-75 |
| 21 | (2)-81 | 22 | (2)-76 | 23 | (2)-76 | 24 | (2)-76 | 41 | (2)-76 | 43 | (2)-76 |
| 21 | (2)-42 | 22 | (2)-81 | 23 | (2)-81 | 24 | (2)-81 | 41 | (2)-81 | 43 | (2)-81 |

When the novel triphenylamine derivative represented by general formula (1) of the present invention is used as a charge-transporting material, a high carrier mobility is obtained.

The novel triphenylamine derivative represented by general formula (1) of this invention is also usable in a wide range of fields including organic electroluminescence (EL).

If a charge-transporting material containing the triphenylamine derivative represented by general formula (1) of the present invention or a mixture of said novel triphenylamine derivative and the triphenylamine derivative represented by the foregoing general formula (2) is used in a photosensitive layer of an electrophotographic photoreceptor, the electrophotographic photoreceptor having high sensitivity can be obtained.

The electrophotographic photoreceptor according to the present invention specifically comprises a conductive support and, formed thereon, a charge-generating layer and a charge-transporting layer which layers perform their respective functions, the charge-transporting layer comprising the compound (1) of this invention as a charge-transporting material. Alternatively, the electrophoto-graphic photoreceptor of the present invention may comprise a conductive support and, formed thereon, a single layer comprising both a charge-generating material and the compound (1) of this invention as a charge-transporting material.

The charge-transporting layer comprising the compound (1) of this invention as a charge-transporting material is formed by vapor-depositing the compound (1) or a mixture of the compound (1) and the compound (2) as it is on a conductive support or charge-generating layer, or by dissolving the compound (1) or a mixture of the compound (1) and the compound (2) into a suitable solvent along with a binder, applying the solution on a conductive support or charge-generating layer, and drying the coating. On the other hand, the single layer comprising a charge-generating material and the compound (1) of this invention is formed by dissolving or dispersing the charge-generating material and the compound (1) into a suitable solvent along with a binder, applying the solution on a conductive support, and drying the coating.

Examples of the binder include polyacrylates, polymethacrylates, polyamides, acrylic resins, acrylonitrile resins, methacrylic resins, vinyl chloride resins, vinyl acetate resins, phenolic resins, epoxy resins, polyesters, alkyd resins, polycarbonates, polyurethanes, polystyrene, and copolymers thereof. Also usable besides such insulating polymers are organic photoconductive polymers, e.g., polyvinylcarbazole, polyvinylanthracene, and polyvinylene.

Of these binders, the use of polycarbonates is particularly suitable. Suitable polycarbonates are bisphenol A type polycarbonates represented by a structural formula given below (e.g., Yupilon E series, manufactured by Mitsubishi Gas Chemical Company, Inc., Japan), bisphenol Z type polycarbonate resins represented by a structural formula given below (e.g., Polycarbonate Z series, manufactured by Mitsubishi Gas Chemical Company, Inc.), and the copolycarbonates disclosed in JP-A-4-179961 which contain bisphenol A or bisphenol Z carbonate units and biphenyl carbonate units as structural units.

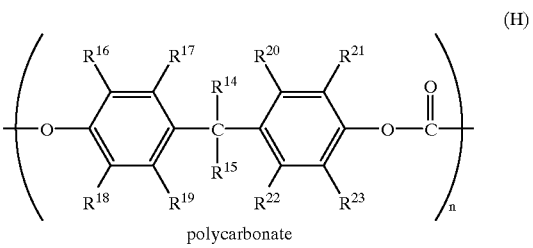

polycarbonate (H)

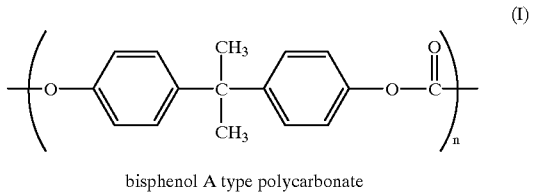

bisphenol A type polycarbonate (I)

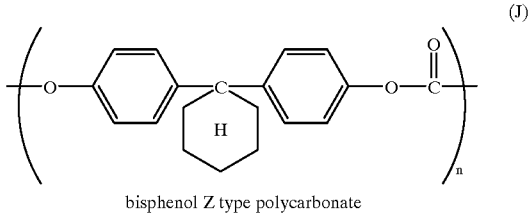

bisphenol Z type polycarbonate (J)

Specific examples of the biphenol copolycarbonates include bisphenol A/biphenyl type polycarbonate resins represented by the following structural formula [n/(n+m)= 0.1–0.9, specifically 0.85].

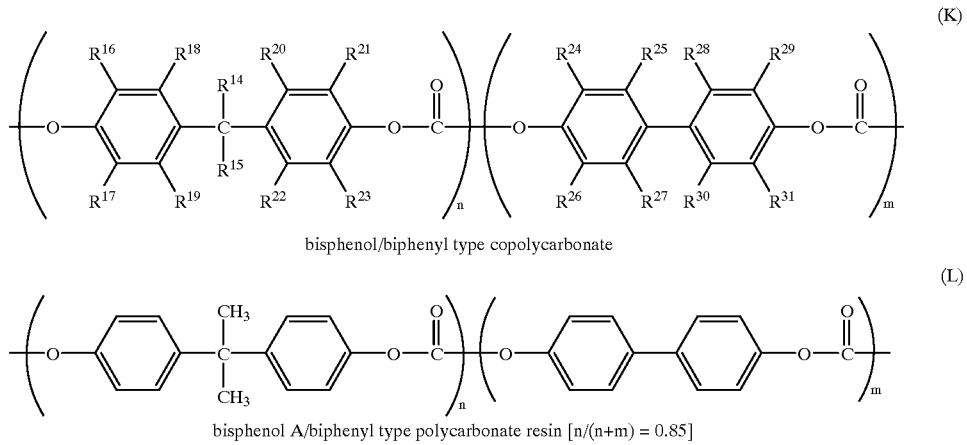

bisphenol/biphenyl type copolycarbonate (K)

bisphenol A/biphenyl type polycarbonate resin [n/(n+m) = 0.85] (L)

(In the above formulae (H) to (L), $R^{14}$ and $R^{15}$ each independently represents a hydrogen atom, an alkyl group or an aryl group, and $R^{14}$ and $R^{15}$ may be bonded in a cyclic form, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$ and $R^{31}$ each independently represents a hydrogen atom, a halogen atom, an alkyl group, or an aryl group; and n and m each represents the molar number of each kind of repeating units.)

Also usable besides the polycarbonates described above is a polycarbonate disclosed in JP-A-6-214412 which has repeating units represented by the following structural formula.

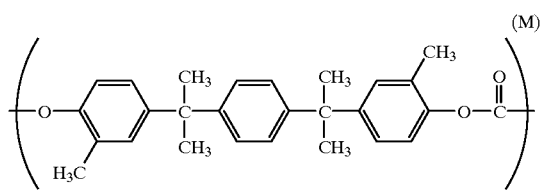

(M)

Further, polycarbonates disclosed in JP-A-6-222581 which have repeating units represented by the following structural formula can be used.

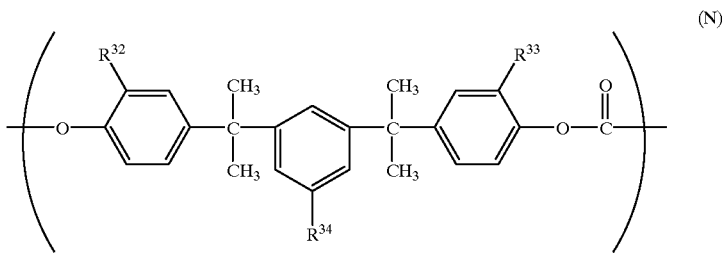

(N)

(In the formula, $R^{32}$, $R^{33}$, and $R^{34}$ may be the same or different and each represents a hydrogen atom, a halogen atom, an alkyl group, a cycloalkyl group, an aryl group, or an arylalkyl group.)

Specific examples of the above polycarbonates are given in the following table.

TABLE 11

| | $R^{32}$ | $R^{33}$ | $R^{34}$ |
|---|---|---|---|
| 1 | H | H | H |
| 2 | H | methyl | H |
| 3 | H | ethyl | H |
| 4 | H | tert-butyl | H |
| 5 | H | phenyl | H |
| 6 | H | benzyl | H |
| 7 | H | dimethylphenylmethyl | H |
| 8 | methyl | H | methyl |
| 9 | methyl | methyl | methyl |
| 10 | methyl | ethyl | methyl |
| 11 | methyl | tert-butyl | methyl |
| 12 | methyl | phenyl | methyl |
| 13 | methyl | benzyl | methyl |
| 14 | methyl | dimethylphenylmethyl | methyl |
| 15 | methyl | cyclohexyl | methyl |
| 16 | Cl | H | Cl |
| 17 | Br | H | Br |
| 18 | isopropyl | H | isopropyl |
| 19 | phenyl | H | phenyl |

The proportion of such a binder to the compound (1) of this invention may be such that the amount of the charge-transporting material is from 10 to 1,000 parts by weight, desirable from 30 to 500 parts by weight, preferably from 40 to 200 parts by weight, per 100 parts by weight of the binder.

Although the solvent to be used is not particularly limited, an organic solvent may be used. Examples thereof include alcohols, e.g., methanol, ethanol, and isopropanol, ketones, e.g., acetone, methyl ethyl ketone, and cyclohexanone, amides, e.g., N,N-dimethylformamide and N,N-dimethylacetamide, sulfoxides, e.g., dimethyl sulfoxide, ethers, e.g., tetrahydrofuran, dioxane, and ethylene glycol dimethyl ether, esters, e.g., ethyl acetate and methyl acetate, halogenated aliphatic hydrocarbons, e.g., methylene chloride, chloroform, 1,2-dichloroethane, dichloroethylene, carbon tetrachloride, and trichloroethylene, and aromatic compounds, e.g., benzene, toluene, xylene, chlorobenzene, and dichlorobenzene. These solvents may be used alone or as a mixture thereof.

As the conductive support to be used in the photoreceptor of this invention, a foil or sheet of a metal, e.g., copper, aluminum, silver, iron, zinc, or nickel, or of an alloy thereof may be employed in sheet or drum form. Also usable as the conductive support is one obtained by depositing any of these metals on a plastic film or cylinder or the like by vacuum deposition or electroplating, or one obtained by forming a layer of a conductive compound, e.g., a conductive polymer, indium oxide, or tin oxide, on a support such as glass, paper, or a plastic film by coating or vapor deposition.

The coating may be conducted by using any of coating techniques such as dip coating, spray coating, spinner coating, wire-wound bar coating, blade coating, roller coating, and curtain coating.

In a preferred drying method, the coating is dried first at room temperature and then with heating. It is preferred that the drying with heating be conducted at a temperature of 30 to 200° C. for 5 minutes to 2 hours with or without air blowing.

If desired and necessary, other charge-transporting materials and various additives may be further incorporated into the charge-transporting layer in this invention. Examples of usable other charge-transporting materials include the hydrazone compounds given in, e.g., JP-B-55-42380, JP-A-60-340999, and JP-A-61-23154 and shown by the following general formula (I), the triphenylamine dimer given in, e.g., JP-B-58-32372 and shown by the following general formula (II), and the distyryl compounds given in, e.g., U.S. Pat. No. 3,873,312 and shown by the following general formula (III), tetraphenylbutadiene compounds, α-phenylstilbene, polyvinylcarbazole and triphenylmethane, but the present invention should not be limited thereto:

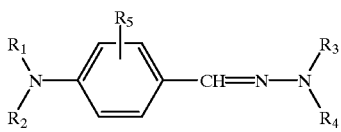

(I)

wherein $R_1$ and $R_2$, which may be the same or different, each represents a lower alkyl group, an aryl group which may have a substituent group, or an aralkyl group which may have a substituent group; $R_3$ and $R_4$, which may be the same or different, and which may combine to form a ring, each represents a lower alkyl group which may have a substituent group, an aryl group which may have a substituent group, an aralkyl group which may have a substituent group, or a heterocyclic group which may have a substituent group; and $R_5$, which may combine with $R_1$ or $R_2$ to form a ring, represents a hydrogen atom, a lower alkyl group, an aryl group which may have a substituent group, an aralkyl group which may have a substituent group, a lower alkoxy group or a halogen atom;

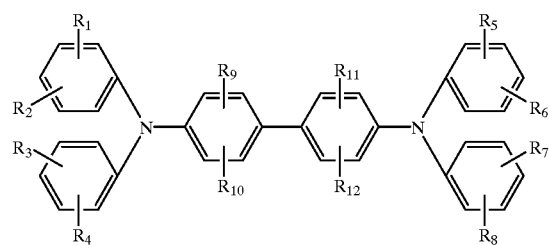

(II)

wherein $R_1$ to $R_{12}$, which may be the same or different, each represents a hydrogen atom, a lower alkyl group, a lower alkoxy group, a lower alkoxy group substituted by a halogen atom, an aryl group which may have a substituent group, or a halogen atom;

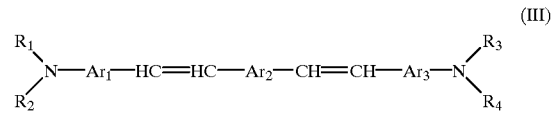

(III)

wherein $R_1$ to $R_4$, which may be the same or different, each represents a lower alkyl group or an aryl group which may have a substituent group; $Ar_1$ and $Ar_3$, which may be the same or different, each represents a phenyl group which may be substituted by at least one group selected from a lower alkyl group, a lower alkoxy group, an aryloxy group and a halogen atom; and $Ar_2$ represents a monocyclic or polycyclic aromatic ring having 4 to 14 carbon atoms which may have the same substituent group as with $Ar_1$ and $Ar_3$, or a heterocycle which may have the same substituent group as with $Ar_1$ and $Ar_3$.

Examples of the additives include plasticizers, e.g., biphenyl compounds (e.g., those disclosed in JP-A-6-332206), m-terphenyl, and dibutyl phthalate, surface lubricants, e.g., silicone oil, graft type silicone polymers, and various fluorocarbons, potential stabilizers, e.g., dicyanovinyl compounds and carbazole derivatives, monophenol type antioxidants, e.g., 2-tert-butyl-4-methoxyphenol and 2,6-di-tert-butyl-4-methylphenol, bisphenol type antioxidants, amine type antioxidants, e.g., 4-diazabicyclo[2.2.2]octane, and salicylic acid type antioxidants, tocopherol.

The thickness of the charge-transporting layer to be obtained is from 5 to 40 μm, preferably from 10 to 30 μm.

Electrical connection of the thus-obtained charge-transporting layer with a charge-generating layer enables the charge-transporting layer to have the functions of receiving carriers injected from the charge-generating layer in the presence of an electric field and transporting the carriers to the surface of the photosensitive layer. In this case, the charge-transporting layer may overlie the charge-generating layer or underlie it, but desirably overlies the charge-generating layer.

On the photosensitive layer thus produced, a protective layer may be formed by coating if desired and necessary. It is also possible to form an undercoat layer having a barrier function and an adhesive function between the conductive support and the photosensitive layer. Examples of the material of the undercoat layer include poly(vinyl alcohol), nitrocellulose, casein, ethylene-acrylic acid copolymers, polyamides, e.g., nylon, polyurethanes, gelatin, and aluminum oxide. The thickness of the undercoat layer is desirably from 0.1 to 5 μm, preferably from 0.5 to 3 μm.

For forming the charge-generating layer, use may be made of one or more materials selected from inorganic charge-generating materials, e.g., selenium, selenium-tellurium, and amorphous silicon, and organic charge-generating materials, e.g., cationic dyes such as pyrylium salt dyes, thiapyrylium salt dyes, azulenium salt dyes, thiacyanine dyes, and quinocyanine dyes, squarylium salt pigments, phthalocyanine pigments, polycyclic quinone pigments such as anthanthrone pigments, dibenzpyrenequinone pigments, and pyranthrone pigments, indigo pigments, quinacridone pigments, azo pigments, and pyrrolopyrrole pigments. These materials may be used alone or in combination to form a layer thereof by vapor deposition or coating. Especially preferred of the organic charge-generating materials enumerated above are the organic charge-generating materials described in *Chem. Rev.*, 1993, 93, pp. 449–486. In particular, phthalocyanine pigments are preferred.

Specific examples of the phthalocyanine pigments include alkoxytitanium phthalocyanine (Ti(OR)$_2$PC), oxotitanium phthalocyanine (TiOPc), copper phthalocyanine (CuPc), metal-free phthalocyanine (H$_2$Pc), hydroxygallium phthalocyanine (HOGaPc), vanadyl phthalocyanine (VOPc), and chloroindium phthalocyanine (ClInPc). More specifically, examples of the TiOPc include α-TiOPc, β-TiOPc, γ-TiOPc, m-TiOPc, Y-TiOPc, A-TiOPc, B-TiOPc, and TiOPc amorphous, and examples of the H$_2$Pc include α-H$_2$Pc, β-H$_2$Pc, σ-H$_2$Pc, and x-H$_2$PC.

Azo pigments are also preferred. The azo pigments include monoazo compounds, bisazo compounds, and trisazo compounds. Specifically, the azo compounds represented by the following structural formulae are preferred.

Bisazo Compounds

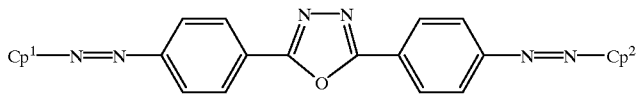

(O)

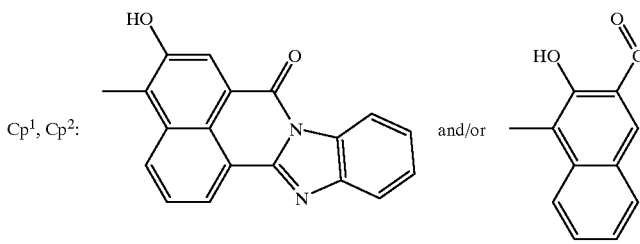 and/or 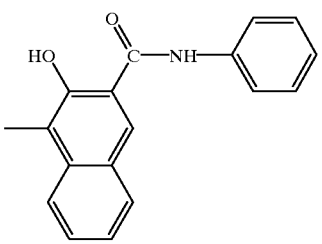

(P)

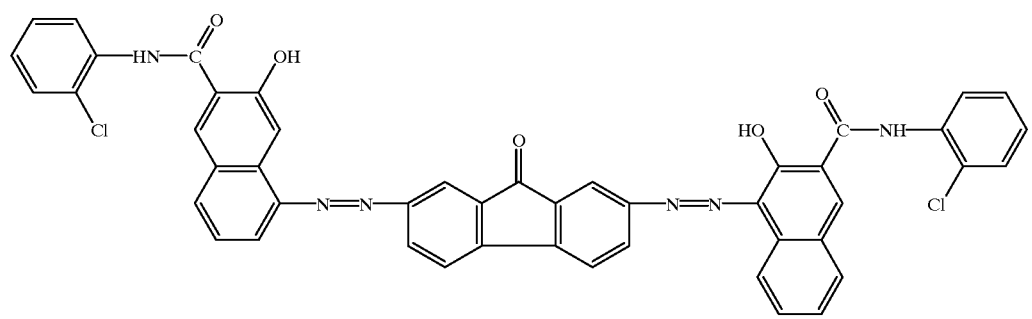

(Q)

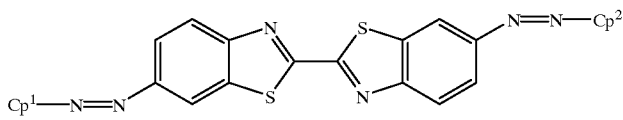

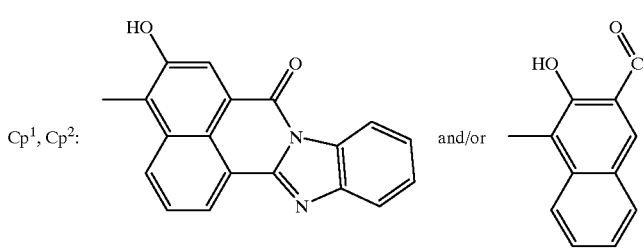 and/or 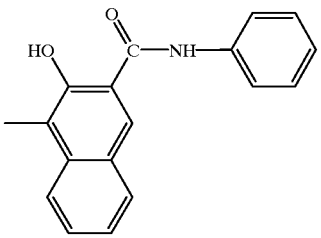

Trisazo Compounds

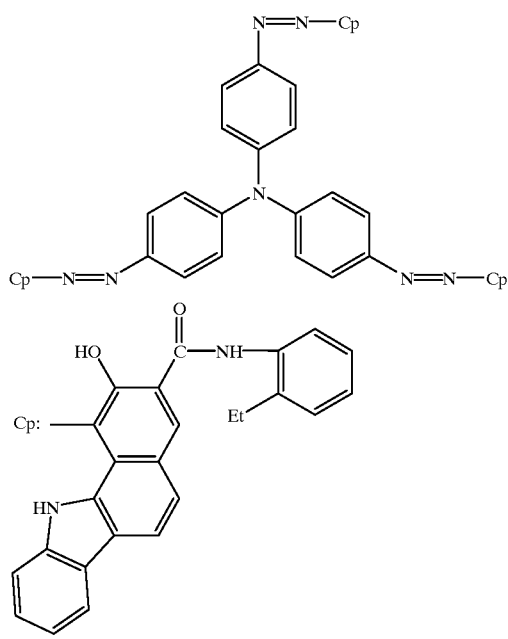

(R)

Further, the perylene compounds and the polycyclic quinone compound which are represented by the following structural formulae are also preferred.

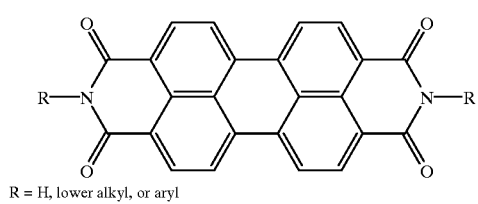

(S)

R = H, lower alkyl, or aryl

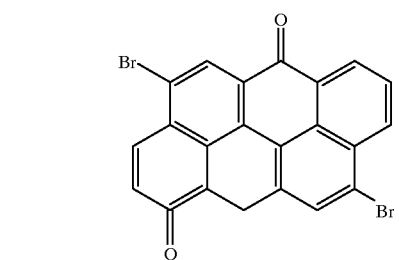

(T)

Besides those materials, any material can be used as long as it generates charges at a high efficiency upon light absorption.

Thus, an electrophotographic photoreceptor containing a charge-transporting layer comprising the triphenylamine derivative (1) of the present invention can be obtained.

As described above, the triphenylamine derivative (1) of this invention, such as those enumerated in Tables 1 to 3, gives a stable film attaining a high carrier mobility and, when used in forming an electrophotographic photoreceptor, is also excellent in various properties.

EXAMPLES

The present invention will be explained below in more detail by reference to the following Examples, but the invention is not construed as being limited thereto.

In the Examples, the analytical instruments and conditions shown below were used.

(1) $^1$H-NMR

Instrument: Type AM-400 (400 MHz), manufactured by Bruker Inc.

Solvent: CDCl$_3$

Internal standard substance: tetramethylsilane (2) MASS

Instrument: Hitachi M-80B (manufactured by Hitachi Ltd. Japan)

(3) HPLC

Column: Intersil ODS-2

Pump: Hitachi L-6000 Pump

Detector: Hitachi C-4000 UV Detector

Integrator: Hitachi D-2000 Chromato-Integrator

Example 1

Synthesis of 4,4',4"-Tris(4'",4'"-diphenyl-1'",3'"-butadienyl)triphenylamine (Exemplified Compound 1; m=n=1, $R^1=R^2=R^3=R^4=R^5=R^6=H$)

(1) Synthesis of 1,1-Diphenylethylene (9a)

Into a 2-liter reaction flask were introduced in a nitrogen stream 31.6 g (1.3 mol) of magnesium and 50 ml of dry THF. Slight amounts of iodine and ethyl bromide were further added, following which the initiation of reaction was ascertained. Subsequently, 600 ml of dry THF was added with stirring, and methyl chloride gas was bubbled into the mixture. The reaction mixture was maintained at 30 to 40° C. by controlling both the amount of the gas being bubbled and cooling. Heat generation ended in 2 hours with the disappearance of the magnesium. The bubbling of methyl chloride gas was then stopped and the mixture was stirred at that temperature for 1 hour to complete the preparation of a Grignard reagent.

To this reaction mixture was added dropwise a liquid mixture of 182.22 g (1.1 mol) of benzophenone (8a; $R^1=R^2=$H) and 364 ml of dry THF at 35 to 40° C. over a period of 30 minutes. This mixture was stirred at that temperature for 15 hours to complete the reaction. The reaction mixture was poured into 1,400 g of cooled 10% aqueous ammonium chloride solution with cooling with ice. This mixture was stirred for 30 minutes, allowed to stand, and then subjected to liquid separation, followed by washing with aqueous common salt solution, drying with magnesium sulfate, and concentration to obtain 200.23 g of a crude carbinol (theoretical yield based on the benzophenone, 98.6%).

Into a 1-liter reaction flask were introduced 200.23 g of the crude carbinol, 400 ml of toluene, and 1 g of p-toluenesulfonic acid (PTSA). Azeotropic dehydration was conducted for 2 hours with toluene refluxing (94–116° C.). After cooling, this reaction mixture was washed with water, with 2% aqueous soda ash solution, and then with water, dried with magnesium sulfate, and concentrated to obtain 190.09 g of crude 1,1-diphenylethylene (9a; $R^1=R^2=H$). This crude 1,1-diphenylethylene (9a) was distilled with a Claisen flask equipped with a vigreux, giving 174.06 g of 1,1-diphenylethylene (9a). b.p., 103° C./1 mmHg The yield based on the benzophenone was 96.5%.

(2) Synthesis of 3,3-Diphenylallyl Chloride (11a; $R^1=R^2=$H) Into a 300-ml reaction flask were introduced 54.13 g (0.3 mol) of 1,1-diphenylethylene (9a), 108.26 g of acetic acid, and 13.51 g (0.45 mol) of paraformaldehyde. Hydrogen chloride in an amount of 13.67 g (0.375 mol) was then bubbled into the mixture with stirring at 30° C. over a period of 3.5 hours, during which the reaction mixture was kept being cooled at 30° C. because slight heat generation occurred. After the bubbling of hydrogen chloride was stopped, the reaction mixture was stirred at that temperature for 2 hours and then allowed to stand overnight. The resulting reaction mixture was poured into 200 ml of water and extracted with 200 ml of toluene. The extract was washed with water, with 2% soda ash solution, and then with water, dried with magnesium sulfate, and concentrated to obtain 68.42 g of a crude chloride. This crude chloride was distilled with a Claisen flask equipped with a vigreux, giving 57.51 g of the desired compound.

b.p., 120–132° C./1 mmHg; Yield based on (8a), 79%; Spectral data for this compound are as follows. Mass spectrum (m/e): 228 (M$^+$), 193, 178, 115; $^1$H-NMR spectrum (400 MHz, δ; ppm in CDCl$_3$): 4.11 (2H, d, J=8.0 Hz), 6.23 (1H, t, J=8.0 Hz), 7.21–7.41 (10H, m);

(3) Synthesis of Diethyl 3,3-Diphenylallylphosphite (5a; $R^1=R^2=H$, R=Et)

A mixture of 40.75 g (0.155 mol) of 3,3-diphenylallyl chloride (11a) and 94.48 g (0.569 mol) of triethyl phosphite was stirred with refluxing for 24 hours. The disappearance of the 3,3-diphenylallyl chloride (11a) was ascertained, before the reaction was terminated. After cooling, the reaction mixture was distilled with a Claisen flask equipped with a vigreux, giving 55.39 g of the desired compound.

b.p., 170–203° C./1 mmHg; Theoretical yield, 99%; Spectral data for this compound are as follows. Mass spectrum (m/e): 330 (M$^+$), 193, 115; $^1$H-NMR spectrum (400 MHz, δ; ppm in CDCl$_3$): 1.31 (6H, t, J=7.0 Hz), 2.71 (2H, dd, J=7.9 Hz, J=22.4 Hz), 4.08 (6H, dt, J=7.1 Hz, J=7.6 Hz), 6.12 (1H, q, J=7.9 Hz, J=7.6 Hz), 7.22–7.38 (10H, m).

(4) Synthesis of 4,4',4"-Triformyltriphenylamine (4a)

Into a 2-l reaction flask were charged 150 g of (0.61 mol) of triphenylamine, 268 g (3.67 mol) of N,N-dimethylformamide and 500 g of a toluene solution in a stream of nitrogen. 562.5 g (3.67 mol) of phosphoryl trichloride were then added dropwise to the solution. After 2 hours from the termination of the dropwise addition, 166.7 g (1.22 mol) of zinc chloride was added to the reaction mixture. The mixture was then stirred at 80° C. for 2 days. The mixture was then allowed to cool. To the mixture was then added dropwise 500 g of water under cooling. To the mixture was then added 100 g of toluene. To the mixture was then added gradually 1314.59 g of sodium carbonate until the solution became alkaline. The mixture was heated to a temperature of 60° C. for 3 hours, and then extracted with toluene. The extract was washed with water, washed with saturated brine, dried over magnesium sulfate, and then subjected to distillation for the removal of solvent to obtain 185.6 g of a solid matter. The solid matter was then recrystallized from a 4:1 (by weight) mixture of isopropanol and toluene to obtain 164.6 g of a mixture of diformylation product and triformylation product (diformylation product:triformylation product=85.6:14.4 (by mol)). 134.95 g out of 165.10 g of the crude product was purified and separated through silica gel chromatography (eluent:toluene/ethyl acetate=8.3), and then recrystallized from a 1.5:1 (by weight) mixture of isopropanol and toluene as a solvent to obtain 15.09 g of 4,4',4"-triformyltriphenylamine (4a) (yield: 7.5%).

m.p. 247–248° C.; Mass spectrum (m/e): 329 (M$^+$), 301, 271, 243, 167, 141, 115, 77, 41; $^1$H-NMR spectrum (400 MHz, δ; ppm in CDCl$_3$); 7.25 (d, J=8.6 Hz, 6H), 7.85 (d, J=8.7 Hz, 6H), 9.95 (s, 3H).

(5) Synthesis of 4,4',4"-tris(4'",4'"-diphenyl-1'",3'"-butadienyl)triphenylamine 0.4 g (1.2 mmol) of 4,4',4"-triformyltriphenylamine (4a) and 1.80 g (5.4 mmol) of 3,3-diphenylallylphosphorous acid diethylester (5) ($R^1=R^2=H$, R=ethyl) were dissolved in 12 ml of DMF. To the solution was then added gradually 0.73 g (6.5 mmol) of potassium tert-butoxide at room temperature. Thereafter, the mixture was stirred at 50° C. for 1 day, and then poured into 120 ml of methanol. The resulting precipitate was withdrawn by filtration, dissolved in 100 ml of benzene, and then washed with water. The resulting organic phase was dried over magnesium sulfate, and then concentrated. The residue was then purified through silica gel chromatography (elute: benzene) to obtain 1.0 g of a crystal. The crystal thus obtained was then recrystallized from toluene to obtain 0.47 g of 4,4',4"-tris(4'", 4'"-diphenyl-1'", 3'"-butadienyl)triphenylamine.

Yield: 45.3%; m.p.: 189–190° C.; Mass spectrum (m/e); 857 (M$^+$), 666, 369, 313, 289, 265, 265, 239, 202; $^1$H-NMR spectrum (400 MHz, δ; ppm in CDCl$_3$); 6.76 (d, J=15.1 Hz, 3H), 6.78 (dd, J=15.0 Hz, J=10.7 Hz, 3H), 6.87 (d, J=10.7 Hz, 3H), 6.93 (d, J=8.6 Hz, 6H), 7.15 (d, J=8.7 Hz, 6H), 7.20–7.42 (m, 30H).

Example 2

Synthesis of 4,4',4"-Tris[4'",4'"-di(p-tolyl)-1'",3'"-butadienyl]triphenylamine (Exemplified Compound 2; m=n=1, $R^1=R^2=R^3=R^4=R^5=R^6=4$-Me)

(1) Synthesis of 1,1-Di(p-tolyl)ethylene (9b; $R^1=R^2=4$-Me)

Into a 1-liter reaction flask were introduced in a nitrogen stream 15.6 g (0.65 mol) of magnesium and 20 ml of THF. Slight amounts of ethyl iodide and iodine were added thereto to initiate reaction. A solution of 111.15 g (0.65 mol) of p-bromotoluene in 500 ml of THF was then added dropwise at room temperature to 40° C. over a period of 2 hours to prepare a Grignard reagent. Thereto was added dropwise a solution of 83.75 g (0.625 mol) of p-methylacetophenone (10a) in 200 ml of THF at that temperature over a period of 3 hours. This mixture was stirred first at room temperature for 3 hours and then with refluxing for 4 hours. The resulting reaction mixture was cooled and poured into 1 liter of 5% aqueous sulfuric acid solution to conduct hydrolysis. This mixture was extracted with toluene, and the extract was washed with aqueous soda ash solution and then with water and concentrated. Thereto were added 300 ml of toluene and 0.5 g of PTSA. The resulting mixture was stirred with refluxing for 4 hours to conduct azeotropic dehydration, followed by washing with aqueous soda ash solution, washing with water, and concentration. The resulting crude 1,1-di(p-tolyl)ethylene (9b) was distilled with a Claisen flask equipped with a vigreux, giving 98.5 g of the desired compound.

b.p., 120–121° C./1 mmHg;

Theoretical yield based on the p-methylacetophenone, 75.8%;

(2) Synthesis of 3,3-Di(p-tolyl)allyl Chloride (11b; $R^1=R^2=$4—Me).

In the same manner as in step (2) in Example 1 for the synthesis of 3,3-diphenylallyl chloride (11a), 58.7 g of 3,3-di(p-tolyl)allyl chloride (11b) (b.p., 153–173° C./1 mmHg; theoretical yield, 67.9%) was obtained from 70.5 g (0.337 mol) of 1,1-di(p-tolyl)ethylene (9b) and 15.1 g (0.505 mol) of paraformaldehyde. This reaction product was recrystallized from hexane to obtain 49.0 g of the desired compound.

m.p., 66° C.; Theoretical yield, 56.7%; Spectral data for the 3,3-di-p-tolylallyl chloride (11b) are as follows. Mass spectrum (m/e): 256 (M$^+$), 221, 206, 165, 129; $^1$H-NMR spectrum (400 MHz, δ; ppm in CDCl$_3$): 2.33 (3H, s), 2.39 (3H, s), 4.13 (2H, d, J=8.1 Hz), 6.17 (1H, t, J=8.1 Hz), 7.01–7.24 (8H, m).

(3) Synthesis of Diethyl 3,3-Di(p-tolyl)allylphosphite (5b; $R^1=R^2=$4—Me, R=Et).

In the same manner as in step (3) in Example 1 for the synthesis of diethyl 3,3-diphenylallylphosphite ((5); $R^1=R^2=$H, R=Et), 35.0 g (0.1365 mol) of 3,3-di(p-tolyl)allyl chloride (8b) was reacted with 68 g (0.409 mol) of triethyl phosphite. Thus, 49.3 g of a distillation residue was obtained. This residue was recrystallized from hexane to obtain 29.9 g of diethyl 3,3-di(p-tolyl)allylphosphite (5b; $R^1=R^2=$4—Me, R=Et).

Theoretical yield, 61.16%; m.p., 56.0° C.; Spectral data for this compound are as follows. Mass spectrum (m/e): 358 (M$^+$), 314, 221, 129; $^1$H-NMR spectrum (400 MHz, δ; ppm in CDCl$_3$): 1.30 (6H, t, J=7.1 Hz), 2.32 (3H, s), 2.39 (3H, s), 2.71 (2H, dd, J=7.9 Hz, J=22.4 Hz), 4.07 (4H, q, J=7.1 Hz, J=8.1 Hz), 6.05 (1H, dd, J=7.9 Hz, J=15.2 Hz), 7.06–7.19 (8H, m).

(4) Synthesis of 4,4',4"-Tris[4'",4'"-di(p-tolyl)-1'",3'"-butadienyl]triphenylamine Using 0.4 g (1.2 mmol) of 4,4',4"-triformyltriphenylamine (4a), 1.96 g (5.5 mmol) of diethyl 3,3-di(p-tolyl) allylphosphite (5b, $R^1=R^2=$4-Me, R=Et), 12 ml of DMF, and 1.22 g (10.9 mmol) of potassium tert-butoxide, reaction and post-treatments were carried out in the same manner as in step (5) in Example 1. As a result, 0.69 g of 4,4',4"-tris[4'", 4'"-di(p-tolyl)-1'",3'"-butadienyl]triphenylamine was obtained.

Yield, 60.3%; m.p., 155–156° C.; Mass spectrum (m/e): 942, 722, 632, 307, 279, 229, 202; $^1$H-NMR spectrum (400 MHz, δ; ppm in CDCl$_3$): 2.35 (s, 9H), 2.40 (s, 9H), 6.59–6.67 (m, 3H), 6.76–6.83 (m, 6H), 6.93 (d, J=8.6 Hz, 6H), 7.09 (d, J=8.3 Hz, 6H), 7.12–7.30 (m, 24H).

In addition, a minor peak of 6.20–6.38 (m) was observed.

Example 3

Synthesis of 4,4'-Bis(4'",4'"-diphenyl-1'",3'"-butadienyl)-4"-[4"",4""-di(p-tolyl)-1'",3'"-butadienyl]triphenylamine (Exemplified Compound 5; m=n=1, $R^1=R^2=R^5=R^6=$H, $R^3=R^4=$4-Me)

(1) Synthesis of 4,4'-Bis(4'",4'"-Diphenyl-1'",3'"-butadienyl)-4"-formyltriphenylamine (12a).

In 15 ml of DMF were dissolved 2.0 g (6.1 mmol) of 4,4',4"-triformyltriphenylamine (4a) and 4.0 g (12.1 mmol) of diethyl 3,3-diphenylallylphosphite (5b, $R^1=R^2=$H, R=Et). Thereto was gradually added 1.5 g (13.4 mmol) of potassium tert-butoxide. After the mixture was stirred at room temperature overnight, it was poured into 100 ml of water. This mixture was extracted twice with toluene, and the organic layer was dried with magnesium sulfate and concentrated. The residue was purified by silica gel column chromatography (eluent: benzene), giving 1.24 g of an oily matter. This reaction product was crystallized from an acetonitrile/ethyl acetate mixed solvent to obtain 1.03 g of 4,4'-bis(4'",4'"-diphenyl-1'",3'"-butadienyl)-4"-formyltriphenylamine (12a).

Yield, 24.9%; m.p., 179–181° C.; Spectral data for this compound are as follows. Mass spectrum (m/e): 681 (M$^+$), 505, 203; $^1$H-NMR spectrum (400 MHz, δ; ppm in CDCl$_3$): 6.69 (d, J=14.1 Hz, 2H), 6.85 (dd, J=27.1 Hz, J=10.9 Hz, 2H), 6.87 (d, J=3.1 Hz, 2H), 6.99–7.06 (m, 6H), 7.21–7.44 (m, 24H), 7.66 (d, J=8.8 Hz, 2H), 9.82 (s, 1).

(2) Synthesis of 4,4'-Bis(4'",4'"-diphenyl-1'",3'"-butadienyl)-4"-[4'",4'"-di(p-tolyl)-1'",3'"-butadienyl]triphenylamine.

In 10 ml of DMF were dissolved 1.4 g (2.1 mmol) of 4,4'-bis(4'",4'"-diphenyl-1'",3'"-butadienyl)-4"-formyltriphenylamine (12a) and 885 mg (2.5 mmol) of diethyl 3,3-di(p-tolyl)allylphosphite ((5); $R^1=R^2=$4-Me, R=Et). Thereto was gradually added 280 mg (2.5 mmol) of potassium tert-butoxide. Reaction was allowed to proceed overnight. The same post-treatments as in step (5) in Example 1 were performed to obtain 1.11 g of 4,4'-bis(4'", 4'"-diphenyl-1'",3'"-butadienyl)-4"-[4"",4""-di(p-tolyl)-1'", 3'"-butadienyl]triphenylamine.

Yield, 61.1%; m.p., 133–135° C.; Spectral data for this compound are as follows.

Mass spectrum (m/e): 885 (M$^+$), 44; $^1$H-NMR spectrum (400 MHz, δ; ppm in CDCl$_3$): 2.35 (s, 3H), 2.40 (s, 3H), 6.59–6.70 (m, 3H), 6.73–6.83 (m, 4H), 6.87 (d, J=10.8 Hz, 2H), 6.90–7.00 (m, 6H), 7.09 (d, J=8.0 Hz, 2H), 7.12–7.43 (m, 32H).

In addition, a minor peak of 6.20–6.35 (m) was observed.

Example 4

Synthesis of 4,4'-Bis(4'",4'"-diphenyl-1'",3'"-butadienyl)-4"-(2"",2""-diphenylvinyl)triphenylamine (Exemplified Compound 21; m=1, n=0, $R^1=R^2=R^5=R^6=$H, $R^3=R^4=$H)

Using 1.77 g (2.6 mmol) of 4,4'-bis(4'",4'"-diphenyl-1'", 3'"-butadienyl)-4"-formyltriphenylamine (12a), 1.0 g (3.3 mmol) of diethyl diphenylmethylphosphite (5"), $R^3=R^4=$H, R=Et), 400 mg (3.6 mmol) of potassium tert-butoxide, and 10 ml of DMF, the same procedure as in step (5) in Example 1 was carried out. Thus, 2.01 g of 4,4'-bis(4'",4'"-diphenyl-1'",3'"-butadienyl)-4"-(2"",2""-diphenylvinyl) triphenylamine was obtained.

Yield, 92.9%; m.p., 127–128° C.; Mass spectrum (m/e): 832 (M$^+$), 831, 667; $^1$H-NMR spectrum (400 MHz, δ; ppm in CDCl$_3$): 6.65 (d, J=15.0 Hz, 2H), 6.72–6.95 (m, 13H), 7.12–7.43 (m, 34H).

Example 5
Synthesis of 4,4'-Bis(2''',2'''-diphenylvinyl)-4''-(4'''',4''''-diphenyl-1'''',3''''-butadienyl)triphenylamine (Exemplified Compound 41; m=n=0, $R^1=R^2=R^5=R^6=R^3=R^4=H$)

(1) Synthesis of 4,4'-Bis(2''',2'''-diphenylvinyl)-4''-formyltriphenylamine (13a)

Using 2.0 g (6.1 mmol) of 4,4',4''-triformyltriphenylamine (4a), 3.7 g (12.2 mmol) of diethyl diphenylmethylphosphite ((5''), $R^3=R^4=H$, R=Et), 1.4 g (12.5 mmol) of potassium tert-butoxide, and 20 ml of DMF, the same treatments as in step (1) in Example 3 were performed. Thus, 728 mg of crude compound (13a) was obtained. This reaction product was crystallized from ethyl acetate to obtain 558 mg of 4,4'-bis(2''',2'''-diphenylvinyl)-4''-formyltriphenylamine (13a).

Yield, 14.5%; m.p., 159–161° C.; Mass spectrum (m/e): 629 ($M^+$), 315, 179; $^1$H-NMR spectrum (400 MHz, δ; ppm in $CDCl_3$): 6.84 (d, J=8.7 Hz, 4H), 6.90–6.97 (m, 6H), 6.98 (d, J=8.7 Hz, 2H), 7.20–7.38 (m, 20H), 7.64 (d, J=8.8 Hz, 2H), 9.79 (s, 1H).

(2) Synthesis of 4,4'-Bis(2''',2'''-diphenylvinyl)-4''-(4'''',4''''-diphenyl-1'''',3''''-butadienyl)triphenylamine Using 1.53 g (2.4 mmol) of 4,4'-bis(2''',2'''-diphenylvinyl)-4''-formyltriphenylamine (13a), 963 mg (2.9 mmol) of diethyl 3,3-diphenylallylphosphite ((5), $R^1=R^2=H$, R=Et), 350 mg (3.1 mmol) of potassium tert-butoxide, and 10 ml of DMF, the same treatments as in step (5) in Example 1 were performed. Thus, 1.66 g of 4,4'-bis(2''',2'''-diphenylvinyl)-4''-(4'''',4''''-diphenyl-1'''',3''''-butadienyl)triphenylamine was obtained.

Yield, 84.7%; m.p., 140–142° C.; Mass spectrum (m/e): 805, 629, 268; $^1$H-NMR spectrum (400 MHz, δ; ppm in $CDCl_3$): 6.64 (d, J=15.0 Hz, 1H), 6.73–6.81 (m, 5H), 6.82–6.93 (m, 10H), 7.12–7.19 (m, 5H), 7.20–7.43 (m, 26H).

In addition, minor peaks of 6.23 (t, J=11.6 Hz) and 6.35 (d, J=11.6 Hz) were observed.

Example 6
Synthesis of 4,4'-Bis(2''',2'''-diphenylvinyl)-4''-[4'''',4''''-di(p-tolyl)-1'''',3''''41-butadienyl]triphenylamine (Exemplified Compound 45; m=n=0, $R^1=R^2=R^3=R^4=H$, $R^5=R^6$=4-Me).

Using 1.58 g (2.5 mmol) of 4,4'-bis(2''',2'''-diphenylvinyl)-4''-formyltriphenylamine (13a), 1.0 g (2.8 mmol) of diethyl 3,3-di(p-tolyl)allylphosphite ((5), $R^1=R^2$=4-Me, R=Et), 340 mg (3.0 mmol) of potassium tert-butoxide, and 10 ml of DMF, the same treatments as in step (5) in Example 1 were performed. Thus, 1.72 g of 4,4'-bis(2''',2'''-diphenylvinyl)-4''-[4'''',4''''-di(p-tolyl)-1'''',3''''-butadienyl]triphenylamine was obtained.

Yield, 82.2%; m.p., 131–133° C.; Mass spectrum (m/e): 834 ($M^+$), 833, 629, 416, 179; $^1$H-NMR spectrum (400 MHz, δ; ppm in $CDCl_3$): 2.35 (s, 3H), 2.41 (s, 3H), 6.58–6.65 (m, 1H), 6.75–6.92 (m, 13H), 7.08–7.37 (m, 31H).

Synthesis Example 1
Synthesis of 4,4',4''-Tris(2''',2'''-diphenylvinyl)triphenylamine (Comparative Compound 1)

Using 622 mg (1.89 mmol) of 4,4',4''-triformyltriphenylamine (4a), 1.9 g (6.25 mmol) of diethyl diphenylmethylphosphite ((5''), $R^3=R^4=H$, R=Et), 10 ml of DMF, and 1.0 g (8.9 mmol) of potassium tert-butoxide, reaction and post-treatments were carried out in the same manner as in step (5) in Example 1. As a result, 0.80 g of 4,4',4''-tris(2''',2'''-diphenylvinyl)triphenylamine was obtained.

Yield, 54.2%; m.p., 196–197° C.

Comparative Compound 1

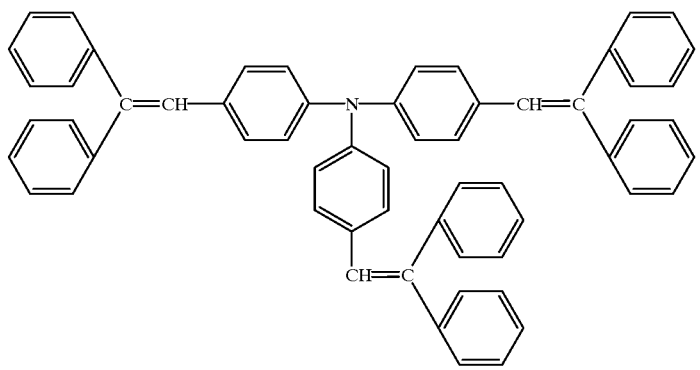

Synthesis Example 2
Synthesis of 1,1-Diphenyl-4-(p-di-n-propylaminophenyl)-1,3-butadiene (Comparative Compound 2)

Using 2.05 g (10.0 mmol) of p-di-n-propylaminobenzaldehyde, 3.6 g (10.9 mmol) of diethyl 3,3-diphenylallylphosphite ((5), $R^1=R^2=H$, R=Et), 1.3 g (11.6 mmol) of potassium tert-butoxide, and 15 ml of DMF, the same treatments as in step (5) in Example 1 were performed. Thus, 2.35 g of 1,1-diphenyl-4-(p-di-n-propylaminophenyl)-1,3-butadiene was obtained.

Yield, 73.8%; m.p., 94.5–95.2° C.

Comparative Compound 2

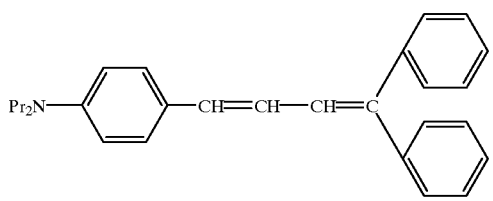

The various 4,4'-diformyltriphenylamine derivatives and 4,4',4''-triformyltriphenylamine derivatives represented by the foregoing general formula (4) were prepared according to the following processes.

In Examples 7 to 10 and Comparative Example 1, the reaction was carried out with p-terphenyl as an internal standard substance in order to use high performance liquid chromatography in the quantitative determination of the product of Vilsmeier reaction of 4-methyltriphenylamine.

Example 7
Vilsmeier Reaction of 4-methyltriphenylamine in the Presence of Zinc Chloride:

Into a 300 ml reaction flask were charged 5.18 g (20.0 mmol) of 4-methyltriphenylamine, 5.85 g (80 mmol) of N,N-dimethylformamide and 35 g of a toluene solution in a stream of nitrogen. To the reaction mixture was then added dropwise 12.27 g (80.0 mmol) of phosphoryl trichloride. To the reaction mixture was then added 0.461 g (2.0 mmol) of p-terphenyl as an internal standard. After 2 hours from the termination of the dropwise addition, 2.73 g (20.0 mmol) of zinc chloride was added to the reaction mixture. The reaction mixture was then stirred at a temperature of 90° C. for 30 hours. To the reaction mixture was then added dropwise 100 g of water under cooling. To the reaction mixture was then added 100 g of toluene. To the reaction mixture was then added gradually sodium carbonate until the reaction mixture became alkaline. The reaction mixture was stirred at a temperature of 60° C. for 3 hours, and then extracted with toluene. The extract was washed with water, washed with saturated brine, dried over magnesium sulfate, and then subjected to distillation for the removal of solvent to obtain a solid matter. 4-Methyltriphenylamine which had been used as a starting material completely disappeared. The reaction product was then quantitatively determined by high performance liquid chromatography with p-perphenyl as an internal standard. The results are set forth in Table 12.

Example 8
Vilsmeier Reaction of 4-methyltriphenylamine in the Presence of Zinc Bromide:

The reaction procedure of Example 7 was followed except that 4.50 g (20.0 mmol) of zinc bromide was used instead of zinc chloride. The reaction product was then quantitatively determined by high performance liquid chromatography. The results are set forth in Table 12.

Example 9
Vilsmeier Reaction of 4-methyltriphenylamine in the Presence of Boron trifluoride-diethyl Ether Complex:

The reaction procedure of Example 7 was followed except that 2.84 g (20.0 mmol) of a boron trifluoride-diethyl ether complex was used instead of zinc chloride. The reaction product was then quantitatively determined by high performance liquid chromatography. The results are set forth in Table 12.

Example 10
Vilsmeier Reaction of 4-methyltriphenylamine in the Presence of Hydrogen Chloride:

The reaction procedure of Example 7 was followed except that hydrogen chloride gas was brown through the reaction system at a rate of about 20 ml/min. for 60 hours instead of zinc chloride. The reaction product was then quantitatively determined by high performance liquid chromatography. The results are set forth in Table 12.

Comparative Example 1
Vilsmeier Reaction of 4-methyltriphenylamine in the Absence of Catalyst:

The reaction procedure of Example 1 was followed except that no Lewis acid was added. The reaction product was then quantitatively determined by high performance liquid chromatography. The results are set forth in Table 12.

TABLE 12

| | Lewis acid or protonic acid | 4-Methyl-4',4''-diformyltri-phenylamine ($A_1$) (%) | 4-Methyl-4'-formyltri-phenylamine ($A_2$) (%) | $A_1/(A_1 + A_2)$ % |
|---|---|---|---|---|
| Example 7 | $ZnCl_2$ | 84.9 | 1.5 | 98.3 |
| Example 8 | $ZnBr_2$ | 68.0 | 3.3 | 95.4 |
| Example 9 | $BF_3(OEt_2)_2$ | 50.7 | 23.7 | 68.1 |
| Example 10 | HCl | 72.0 | 0 | 100 |
| Comparative Example 1 | none | 24.7 | 70.2 | 26.0 |

As can be seen in Table 12, the Vilsmeier reaction in the presence of Lewis acid or protonic acid provides a remarkable enhancement of yield of 4-methyl-4',4''-diformyltriphenylamine ($A_1$).

Example 11
Synthesis of 4-methyl-4',4''-diformyltriphenylamine:

Into a 5 l reaction flask were charged 488.1 g (6.68 mol) of N,N-dimethylformamide and 1,200 g of toluene in a stream of nitrogen. To the reaction mixture was then added dropwise 930.8 g (6.07 mol) of phosphorus oxychloride at a temperature of from 5° C. to 10° C. in 2 hours. The reaction mixture was then stirred at the same temperature for 1 hour. To the reaction mixture was then added dropwise a mixture of 400 g (1.52 mol) of 4-methyltriphenylamine and 800 g of toluene at a temperature of from 10° C. to room temperature in 1 hour. After the termination of the dropwise addition, to the reaction mixture was added 206.85 g (1.52 mol) of anhydrous zinc chloride. The reaction mixture was then allowed to undergo reaction at a temperature of from 80° C. to 81° C. for 30 hours (until the content of monoformyl form was identified to be not more than 1% by HPLC). The reaction system was cooled to a temperature of about 40° C., and then poured into 8 l of chilled water. The reaction system was neutralized with 1,500 g of soda ash, and then stirred and extracted at a temperature of from 55° C. to 60° C. for 1 hour. The reaction solution was then filtered through Celite. The filtrate was subjected to separation, and then washed twice with 8 l of water (until the pH value thereof reached 7). The material was dried over anhydrous magnesium sulfate, and then concentrated to obtain 520.8 g of a residue. The residue was then recrystallized from a 9:1 (by weight) mixture of isopropanol and toluene to obtain 413.6 g of 4-methyl-4',4''-diformyltriphenylamine. (m.p.: 153–153.5° C.; theoretical yield: 85.7%)

Example 12
Synthesis of 4-ethyl-4',4''-diformyltriphenylamine:

In a 300 ml reaction flask were weighed out 50 ml of toluene, 2.5 g (18.3 mmol) of zinc chloride, 5.0 g (18.3 mmol) of 4-ethyltriphenylamine and 5.66 g (77.5 mmol) of N,N-dimethylformamide in a stream of nitrogen. To the reaction mixture was then added dropwise gradually 11.5 g (75.0 mmol) of phosphoryl trichloride. After the termination of the dropwise addition, the reaction mixture was stirred at a temperature of 90° C. for 30 hours. To the reaction mixture was then added dropwise 100 g of water under cooling. To the reaction mixture was then added 100 g of toluene. To the reaction mixture was then added gradually sodium carbonate until it became alkaline. The reaction mixture was heated to a temperature of 60° C. for 3 hours, and then extracted with toluene. The extract was washed with water, washed with saturated brine, dried over $MgSO_4$, and then subjected to distillation for the removal of solvent. The resulting residue was then subjected to separation through silica gel column chromatography (eluent: 10:1 mixture of toluene and ethyl acetate) to obtain 0.97 g (17.6%) of 4-ethyl-4'-formyltriphenylamine and 4.93 g (81.8%) of 4-ethyl-4',4"-diformyltriphenylamine. 4-Ethyl-4'-formyltriphenylamine thus obtained was then recrystallized from methanol to obtain 0.72 g (13.1%) of 4-ethyl-4'-formyltriphenylamine in crystal form. The results are set forth in Table 13. The reaction product exhibited the following physical properties:
4-Ethyl-4'-formyltriphenylamine:

m.p.: 81.82° C.; Mass spectrum; 301 (M$^+$), 286; $^1$H-NMR spectrum (400 MHz, CDCl$_3$, δppm); 1.23 (d, J=7.6 Hz, 3H), 2.65 (q, J=7.6 Hz, 2H), 6.98 (d, J=8.8 Hz, 2H), 7.09 (d, J=8.5 Hz, 2H), 7.13–7.20 (m, 5H), 7.30–7.36 (m, 2H), 7.65 (d, J=8.9 Hz, 2H), 9.80 (s, 1H).
4-Ethyl-4',4"-diformyltriphenylamine:

m.p.: 103–104° C.; Mass spectrum; 329, 314, 167, 105; $^1$H-NMR spectrum (400 MHz, CDC$_{13}$, δppm); 1.28 (t, J=7.6 Hz, 3H), 2.70 (q, J=7.6 Hz, 2H), 7.08 (d, J=8.4 Hz, 2H), 7.17 (d, J=8.7 Hz, 4H), 7.23 (d, J=8.4 Hz, 2H), 7.76 (d, J=8.7 Hz, 4H), 9.90 (s, 2H).

COMPARATIVE Example 2

The reaction procedure of Example 12 was followed except that zinc chloride was not added. The results are set forth in Table 13.

Example 13
Synthesis of 2-methyl-4',4"-diformyltriphenylamine:

5 g (19.3 mmol) of 2-methyltriphenylamine, 6.14 g (84.0 mmol) of N,N-dimethylformamide, 12.5 g (81.5 mmol) of phosphorus oxychloride, 2.7 g (19.8 mmol) of zinc chloride, and 100 ml of toluene were subjected to reaction, post-treatment and isolation in the same manner as in Example 12. The results are set forth in Table 13. The reaction product exhibited the following physical properties:
2-Methyl-4'-formyltriphenylamine:

m.p.; Mass spectrum; 287 (M$^+$), 180, 167; $^1$H-NMR spectrum (400 MHz, CDCl$_3$, δppm); 2.05 (s, 3H), 6.88 (q, J=8.7 Hz, 2H), 7.07–7.17 (m, 4H), 7.21–7.26 (m, 2H), 7.26–7.33 (m, 3H), 7.67 (d, J=8.9 Hz, 2H), 9.79 (s, 1H).
2-Methyl-4',4"-diformyltriphenylamine:

m.p.: 121–122° C.; Mass spectrum; 315 (M$^+$), 286, 271, 256, 243, 210, 180, 167; $^1$H-NMR spectrum (400 MHz, CDCl$_3$, δppm); 2.03 (s, 3H), 7.12 (d, J=8.6 Hz, 4H), 7.12–7.17 (m, 1H), 7.28–7.36 (m, 3H), 7.77 (d, J=8.5 Hz, 4H), 9.88 (s, 2H).

Comparative Example 3

The reaction procedure of Example 13 was followed except that zinc chloride was not added. The results are set forth in Table 13.

Example 14
Synthesis of 4-methoxy-4',4"-diformyltriphenylamine:

5 g (18.16 mmol) of 4-methoxyltriphenylamine, 5.66 g (77.5 mmol) of N,N-dimethylformamide, 11.5 g (75.0 mmol) of phosphorus oxychloride, 2.5 g (18.3 mmol) of zinc chloride, and 100 ml of toluene were subjected to reaction, post-treatment and isolation in the same manner as in Example 12. The results are set forth in Table 13. The reaction product exhibited the following physical properties:
4-Methoxy-4'-formyltriphenylamine:

m.p.: 73–74° C.; Mass spectrum; 315 (M$^+$), 288, 230, 129; $^1$H-NMR spectrum (400 MHz, CDCl$_3$, δppm); 3.80 (s, 3H), 6.89 (d, J=9.0 Hz, 2H), 6.94 (d, J=8.7 Hz, 2H), 7.12 (d, J=9.1 Hz, 2H), 7.16 (m, 3H), 7.32 (m, 2H), 7.64 (d, J 8.9 Hz, 2H), 9.78 (s, 1H).
4-Methoxy-4',4"-diformyltriphenylamine:

m.p.: 113–114° C.; Mass spectrum (m/e); 331 (M$^+$), 316, 259, 230; $^1$H-NMR spectrum (400 MHz, δ; ppm in CDCl$_3$); 3.85 (3H, s), 6.94 (2H, d, J=9.0 Hz), 7.12 (2H, d, J=9.0 Hz), 7.17 (4H, d, J=8.7 Hz), 7.56 (4H, d, J=8.7 Hz), 9.88 (2H, s).

Comparative Example 4

The reaction procedure of Example 14 was followed except that zinc chloride was not added. The results are set forth in Table 13.

TABLE 13

| | 4-Ethyl-4',4"-diformyltriphenyl-amine (B$_1$) yield (%) | 4-Ethyl-4'-formyltriphenyl-amine (B$_2$) yield (%) | B$_1$/(B$_1$ + B$_2$) % |
|---|---|---|---|
| Example 12 | 81.3 | 17.6 | 82.2 |
| Comparative Example 2 | 41.3 | 46.4 | 47.1 |

| | 2-Methyl-4',4"-diformyltriphenyl-amine (C$_1$) yield (%) | 2-Methyl-4'-formyltriphenyl-amine (C$_2$) yield (%) | C$_1$/(C$_1$ + C$_2$) % |
|---|---|---|---|
| Example 13 | 87.1 | 5.0 | 94.6 |
| Comparative Example 3 | 48.5 | 42.4 | 53.4 |

| | 4-Methoxy-4',4"-diformyltriphenyl-amine (D$_1$) yield (%) | 4-Methoxy-4'-formyltriphenyl-amine (D$_2$) yield (%) | D$_1$/(D$_1$ + D$_2$) % |
|---|---|---|---|
| Example 14 | 91.4 | 0 | 100 |
| Comparative Example 4 | 52.8 | 29.4 | 64.2 |

As can be seen in Table 13, the Vilsmeier reaction in the presence of Lewis acid provides a remarkable enhancement of yield of diformyltriphenylamine.

Example 15
Synthesis of 4,4'-diformyltriphenylamine and 4,4',4"-triformyltriphenylamine:

Into a 2 l reaction flask were charged 150 g (0.61 mmol) of triphenylamine, 268 g (3.67 mmol) of N,N-dimethylformamide and 500 g of a toluene solution in a stream of nitrogen. To the reaction mixture was then added dropwise 562.5 g (3.67 mmol) of phosphoryl trichloride. After 2 hours from the termination of the dropwise addition, 166.7 g (1.22 mmol) of zinc chloride was added to the reaction mixture. The reaction mixture was then stirred at a temperature of 80° C. for 2 days. The reaction mixture was then allowed to cool. To the reaction mixture was then added dropwise 500 g of water under cooling. To the reaction mixture was then added 100 g of toluene. To the reaction mixture was then added gradually 1,314.59 g of sodium carbonate until the reaction mixture became alkaline. The reaction mixture was stirred at a temperature of 60° C. for 3 hours, and then extracted with toluene. The extract was washed with water, washed with saturated brine, dried over magnesium sulfate, and then subjected to distillation for the removal of solvent to obtain 185.6 g of a solid matter. The solid matter thus obtained was then recrystallized from a 4:1 (by weight) mixture of isopropanol and toluene to obtain 164.6 g of a mixture of a diformylation product and a triformylation product.

134.95 g out of 165.10 g of the crude reaction product was purified and separated through silica gel chromatography (eluent: 8:3 (by weight) of toluene and ethyl acetate), and then recrystallized from a 1.5:1 (by weight) mixture of isopropanol and toluene to obtain 122.6 g of 4,4'-diformyltriphenylamine. (m.p.: 148–149° C.; yield: 67.4%)

Further, 15.09 g (yield: 7.5%) of 4,4',4"-triformyltriphenylamine was obtained.
m.p.: 247–248° C.

Comparative Example 5

Into a 1 l reaction flask were charged 44.74 g (0.612 mol) of N,N-dimethylformamide and 200 ml of dichloroethane. To the reaction mixture was then added dropwise 93.82 g (0.612 mol) of phosphorus oxychloride at a temperature of from 5° C. to 10° C. in 30 minutes. Thereafter, to the reaction mixture was added a solution of 50 g (0.204 mol) of triphenylamine in 200 ml of dichloroethane at room temperature in 30 minutes. The reaction mixture was stirred at room temperature for 12 hours and then under reflux for 24 hours. The reaction mixture was cooled. To the reaction mixture were then added 44.74 g (0.612 mol) of N,N-dimethylformamide and 93.82 g (0.612 mol) of phosphorus oxychloride. The reaction mixture was then stirred under reflux for 24 hours. This procedure was repeated three times. The reaction mixture was then poured into 4 l of ice-water. To the reaction mixture was then added 1 l of toluene. The reaction mixture was then neutralized with sodium carbonate. The reaction mixture was stirred at a temperature of 65° C. for 1 hour, separated, washed with water, dried, and then concentrated to obtain 56.6 g of a residue. The residue was then twice recrystallized from isopropyl alcohol to obtain 24.3 g (theoretical yield: 39.5%) of 4,4'-diformyltriphenylamine.

Comparative Example 6

Into a 3 l reaction flask were charged 110.52 g (1.51 mol) of N,N-dimethylformamide and 757 ml of 1,2-dichloroethane. To the reaction mixture was then added dropwise 231.84 g (1.51 mol) of phosphorus oxychloride at a temperature of from 0° C. to 5° C. in 1 hour. Thereafter, the reaction mixture was stirred at room temperature for 1 hour. To the reaction mixture was added a solution of 126.17 g (0.504 mol) of triphenylamine in 505 ml of 1,2-dichloroethane at a temperature of from 0° C. to 5° C. in 1 hour. The reaction mixture was stirred at room temperature for 12 hours and then under reflux for 26 hours. The reaction mixture was then cooled. To the reaction mixture were then added 110.52 g (1.5 mol) of N,N-dimethylformamide and 231.84 g (1.51 mol) of phosphorus oxychloride. The reaction mixture was then stirred under reflux for 26 hours. This procedure was repeated three times. The reaction mixture was then poured into 10 l of ice-water. The reaction mixture was then neutralized with 1,823 g of sodium carbonate. The reaction solution was stirred at a temperature of from 50° C. to 60° C. for 1 hour, and then subjected to separation with chloroform. The resulting organic phase was twice washed with water, dried over magnesium sulfate, and then concentrated. The residue was then purified through silica gel column chromatography (eluent: 9:1 mixture of benzene and ethyl acetate) to obtain 1.3 g of a crystal. The crystal thus obtained was then recrystallized from a mixture of acetonitrile and ethyl acetate to obtain 0.52 g of 4,4',4"-triformyltriphenylamine (yield: 0.5%).

As can be seen in Example 15 and Comparative Examples 5 and 6, the Vilsmeier reaction in the presence of a Lewis acid makes it possible to synthesize 4,4'-diformyltriphenylamine and 4,4',4"-triformyltriphenylamine in a high yield.

Example 16
Synthesis of 4-bromo-4',4"-diformyltriphenylamine:

10.0 g (30.4 mmol) of 4-bromotriphenylamine, 9.79 g (133.9 mmol) of N,N-dimethylformamide, 18.67 g (121.8 mmol) of phosphorus oxychloride, 4.15 g (30.4 mmol) of zinc chloride, and 100 ml of toluene were subjected to reaction, post-treatment and isolation in the same manner as in Example 12. The results are set forth in Table 14. The reaction product exhibited the following physical properties:
4-Bromo-4'-formyltriphenylamine:
m.p.: 119–120° C.; Mass spectrum (m/e); 353, 351, 322, 271, 243, 167, 141, 115; $^1$H-NMR spectrum (400 MHz, δ; ppm in CDCl$_3$); 7.03 (m, 4H), 7.12–7.21 (m, 3H), 7.35 (m, 2H), 7.43 (d, J=8.9 Hz, 2H), 7.69 (d, J=8.9 Hz, 2H), 9.84 (s, 1H).
4-Bromo-4',4"-diformyltriphenylamine:
m.p.: 201.5–202.5° C.; Mass spectrum (m/e); 381, 379, 271, 241, 167; $^1$H-NMR spectrum (400 MHz, δ; ppm in CDCl$_3$); 7.05 (d, J=8.8 Hz, 2H), 7.18 (d, J=8.7 Hz, 4H), 7.51 (d, J=8.9 Hz, 2H), 7.78 (d, J=8.8 Hz, 4H), 9.90 (s, 2H).

Comparative Example 7

The reaction procedure of Example 16 was followed except that zinc chloride was not added. The results are set forth in Table 14.

Example 17
Synthesis of 4-p-tolyl-4',4"-diformyltriphenylamine:

10.0 g (29.5 mmol) of 4-p-tolyltriphenylamine, 9.47 g (129.6 mmol) of N,N-dimethylformamide, 18.06 g (117.8 mmol) of phosphorus oxychloride, 4.02 g (29.5 mmol) of zinc chloride, and 100 ml of toluene were subjected to reaction, post-treatment and isolation in the same manner as in Example 13. The results are set forth in Table 14. The reaction product exhibited the following physical properties:
4-p-Tolyl-4'-formyltriphenylamine:
Mass spectrum; 363, 334, 243, 167, 149; $^1$H-NMR spectrum (400 MHz, CDCl$_3$, δppm); 2.39 (s, 3H), 7.07 (d, J=8.7 Hz, 2H), 7.16–7.27 (m, 7H), 7.36 (m, 2H), 7.48 (d, J=8.2 Hz, 2H), 7.54 (d, J=8.7 Hz, 2H), 7.69 (d, J=8.9 Hz, 2H), 9.81 (s, 1H).
4-p-Tolyl-4'-4"-diformyltriphenylamine:
m.p.: 197–198° C.; Mass spectrum (m/e); $^1$H-NMR spectrum (400 MHz, δ; ppm in CDCl$_3$); 2.42 (s, 3H), 7.19–7.28 (m, 8H), 7.49 (d, J=8.2 Hz, 2H), 7.59 (d, J 8.7 Hz, 2H), 7.79 (d, J=8.8 Hz, 4H), 9.90 (s, 2H).

Comparative Example 8

The reaction procedure of Example 17 was followed except that zinc chloride was not added. The results are set forth in Table 14.

TABLE 14

|  | 4-Bromo-4',4"-diformyltriphenyl-amine ($E_1$) yield (%) | 4-Bromo-4'-formyltriphenyl-amine ($E_2$) yield (%) | $E_1/(E_1 + E_2)$ % |
|---|---|---|---|
| Example 16 | 72.1 | 21.9 | 76.1 |
| Comparative Example 7 | 26.8 | 64.5 | 29.4 |
|  | 4-p-Tris-4',4"-diformyltriphenyl-amine ($F_1$) yield (%) | 4-p-Tris-4'-formyltriphenyl-amine ($F_2$) yield (%) | $F_1/(F_1 + F_2)$ % |
| Example 17 | 80.0 | 17.9 | 81.7 |
| Comparative Example 8 | 38.4 | 52.1 | 42.4 |

Example 18
Synthesis of a Mixture of Exemplified Compound 1 and Exemplified Compound (2)-57
(1) Synthesis of a mixture of 4,4"-diformyltriphenylamine and 4,4',4"-triformyltriphenylamine.
In a 2 l reaction flask were weighed out 100.0 g (0.41 mol) of triphenylamine, 214.5 g (2.93 mol) of N,N- dimethylformamide, and 500 g of toluene in a stream of nitrogen. To the reaction mixture was then added dropwise gradually 375 g (2.45 mol) of phosphorus oxychloride at a temperature of from 24° C. to 53° C. in 30 minutes. Subsequently, to the reaction mixture was added 111.1 g (0.82 mol) of zinc chloride. The reaction mixture was then stirred at a temperature of 80° C. for 57 hours. The reaction mixture was then poured into 2 l of ice-water. To the reaction mixture was then added 500 g of toluene. To the reaction mixture was then added gradually 721.7 g of sodium carbonate so that the pH value thereof reached 11. The reaction mixture was extracted at a temperature of 60° C. with stirring, and then subjected to separation. The resulting toluene phase was washed with water three times. The toluene phase was dried over $Na_2SO_4$, and then concentrated to obtain 133.9 g of a solid matter. The solid matter was then recrystallized from a mixture of 240 g of toluene and 536 g of 2-propanol to obtain 111.6 g of a crystal. $^1$H-NMR of this product showed that it was a 74.4:25.6 (by mol-%) mixture of 4,4'-diformyltriphenylamine and 4,4',4"-triformyltriphenylamine. (m.p.: 141–143° C., 184–192° C.)

(2) Synthesis of a mixture of Exemplified Compound 1 and Exemplified Compound (2)-57

Into a 1 l reaction flask were charged 50 g of a 74.4:25.6 (by mol) mixture of 4,4'-diformyltriphenylamine and 4,4',4"-triformyltriphenylamine synthesized in the process (1), 145.4 g (0.44 mol) of 3,3-diphenylallylphosphorous acid diethyl and 250 ml of N,N-dimethylformamide. To the reaction mixture was then added gradually 59 g (0.526 mol) of potassium t-butoxide. The reaction mixture was then allowed to undergo reaction at a temperature of 50° C. for 8 hours. The reaction mixture was then poured into 2.5 l of water. The resulting precipitate was withdrawn by filtration under reduced pressure, dissolved in 730 g of toluene, and then twice washed with water. The solution was then concentrated. The resulting crude reaction product was then purified through silica gel column chromatography (eluent: toluene) to obtain 127.6 g of a crystal. The crystal thus obtained was then recrystallized from a mixture of toluene and heptane to obtain 77.2 g of a mixture of Exemplified Compound 1 and Exemplified Compound (2)-57. The high performance liquid chromatography of this mixture showed that the molar ratio of Exemplified Compound 1 to Exemplified Compound (2)-57 was 71.4:28.6.

m.p.: 123–125° C.;

APPLICATION EXAMPLES 1 TO 3

One part of chlorodian blue (CDB) and 1 part of a polycarbonate resin (Yupilon E-2000, manufactured by Mitsubishi Gas Chemical Company, Inc.) were kneaded in a ball mill for 5 hours along with 30 parts of dichloroethane as a solvent. The pigment dispersion obtained was applied with a wire-wound bar on a sheet obtained by vapor-depositing aluminum on a poly(ethylene terephthalate) (PET) film, and the coating was dried at 45° C. for 3 hours to form a charge-generating layer having a thickness of about 1 mm. Further, 1 part of each of Exemplified Compounds 1, 21, and 41 and 1 part of a polycarbonate resin (Polycarbonate Z, manufactured by Mitsubishi Gas Chemical Company, Inc.) were mixed in 8 parts of dichloroethane to dissolve them. Each of these solutions was applied on the charge-generating layer with a doctor blade and dried at 80° C. for 3 hours. Thus, photoreceptors 1 to 3 were produced.

The electrophotographic photoreceptors thus obtained were statically examined for electrophotographic properties with an electrostatic recording tester Type SP-428 (manufactured by Kawaguchi Electric Works Co., Ltd., Japan). In this test, the photoreceptor was electrostatically charged by 5-second corona discharge at −6 kV to measure the resulting surface potential $V_0$ (unit: −V), and the resulting photoreceptor was placed in the dark for 5 seconds and then irradiated with light from a tungsten lamp at an illuminance of 5 lux to determine the exposure dose required for the surface potential to decrease by half, i.e., half-decay exposure $E_{1/2}$ (lux·sec), and the residual surface potential VR10 (−V) after 10-second irradiation at an illuminance of 5 lux. The results obtained are shown in Table 15.

APPLICATION COMPARATIVE EXAMPLE 1

Photoreceptor 4 was produced and examined for electrophotographic properties in the same manner as in Application Examples 1 to 3, except that Comparative Compound 1 was used in place of Exemplified Compounds 1, 21, and 41. The results obtained are shown in Table 15. A high value of residual surface potential $V_{R10}$ of a photoreceptor means that the photoreceptor undergoes a phenomenon in which the preceding image is fogged. Hence, $V_{R10}$ values closer to 0 are preferred. The photoreceptors employing Exemplified Compounds 1, 21, and 41 had residual surface potentials $V_{R10}$ of 0, 8, and 6, respectively, whereas the photoreceptor employing Comparative Compound 1 had a $V_{R10}$ as high as 102. The results show that the compounds of this invention were distinctly superior.

APPLICATION EXAMPLES 4 TO 9

On a thin aluminum film formed on a polyester film by vapor deposition, oxotitanium phthalocyanine (TiOPc) was vacuum-deposited at $10^{-6}$ Torr to a thickness of about 0.8 mm to form a charge-generating layer. Further, 1 part of each of Exemplified Compounds 1, 2, 5, 21, 41, and 45 and 1 part of a polycarbonate resin (Polycarbonate Z, manufactured by Mitsubishi Gas Chemical Company, Inc.) were mixed in 8 parts of dichloroethane to dissolve them. Each of these solutions was applied on the charge-generating layer with a doctor blade and dried at 80° C. for 3 hours. Thus, photoreceptors 5 to 10 were produced. Their electrophotographic properties were examined in the same manner as in Application Examples 1 to 3. The results obtained are shown in Table 15.

APPLICATION COMPARATIVE EXAMPLE 2

Photoreceptor 11 was produced and examined for electrophotographic properties in the same manner as in Application Examples 4 to 9, except that Comparative Compound 2 was used in place of Exemplified Compounds 1, 2, 5, 21, 41, and 45. The results obtained are shown in Table 15. The photoreceptors employing Exemplified Compounds 1, 2, 5, 21, and 45 each had a $V_{R10}$ of 0 and the photoreceptor employing Exemplified Compound 41 had a $V_{R10}$ of 4, whereas the photoreceptor employing Comparative Compound 2 had a $V_{R10}$ as high as 58. The results show that the compounds of this invention were distinctly superior.

APPLICATION EXAMPLES 10 TO 12

One part of τ-form metal-free phthalocyanine (τ-$H_2$Pc) and 1 part of a butyral resin (Poly(vinyl butyral) BM-1, manufactured by Sekisui Chemical Co., Ltd., Japan) were kneaded in a ball mill for 5 hours along with 30 parts of tetrahydrofuran as a solvent. The pigment dispersion obtained was applied on a sheet obtained by vapor-depositing aluminum on a poly(ethylene terephthalate) (PET) film, and the coating was dried at 50° C. for 2 hours to form a charge-generating layer. Further, 1 part of each of Exemplified Compounds 5, 21, and 41 synthesized in Examples 3, 5, and 6 and 1 part of a polycarbonate resin (Polycarbonate Z, manufactured by Mitsubishi Gas Chemical Company, Inc.) were mixed in 8 parts of dichloroethane to dissolve them. Each of these solutions was applied on the charge-generating layer with a doctor blade and dried at 80° C. for 2 hours to produce photoreceptors 12 to 14. The photoreceptors thus obtained were examined for electrophotographic properties in the same manner as in Application Examples 1 to 3. The results obtained are shown in Table 16.

APPLICATION COMPARATIVE EXAMPLE 3

Photoreceptor 15 was produced in the same manner as in Application Examples 10 to 12, except that Comparative Compound 2 was used in place of Exemplified Compounds 5, 21, and 41. Its electrophotographic properties were examined in the same manner as in Application Examples 1 to 3. The results obtained are shown in Table 16. The higher the surface potential $V_0$, the better the contrast. If $V_0$ is too low, no contrast results and, hence, image formation is impossible. The photoreceptors employing Exemplified Compounds 5, 21, and 41 according to the present invention had values of $V_0$ of 826, 1,238, and 1,184, respectively, whereas the photoreceptor employing Comparative Compound 2 had a $V_0$ of 67. The results show that the compounds of this invention were distinctly superior.

TABLE 15

| | Photoreceptor No. | Charge Generating Material | Charge Transporting Material | $V_0$ (-V) | $V_{R10}$ (-V) | $E_{1/2}$ (lux · sec) |
|---|---|---|---|---|---|---|
| Application Example 1 | 1 | CDB | Exemplified Compound 1 | 794 | 0 | 4.9 |
| Application Example 2 | 2 | CDB | Exemplified Compound 21 | 1238 | 8 | 8.2 |
| Application Example 3 | 3 | CDB | Exemplified Compound 41 | 1280 | 6 | 8.1 |
| Application Comparative Example 1 | 4 | CDB | Comparative Compound 1 | 1239 | 102 | 4.7 |
| Application Example 4 | 5 | TiOPc, vapor-deposited | Exemplified Compound 1 | 454 | 0 | 0.6 |
| Application Example 5 | 6 | TiOPc, vapor-deposited | Exemplified Compound 2 | 764 | 0 | 0.6 |
| Application Example 6 | 7 | TiOPc, vapor-deposited | Exemplified Compound 5 | 1186 | 0 | 0.7 |
| Application Example 7 | 8 | TiOPc, vapor-deposited | Exemplified Compound 21 | 1376 | 0 | 1.1 |
| Application Example 8 | 9 | TiOPc, vapor-deposited | Exemplified Compound 41 | 1340 | 4 | 1.2 |
| Application Example 9 | 10 | TiOPc, vapor-deposited | Exemplified Compound 45 | 1220 | 0 | 1.2 |
| Application Comparative Example 2 | 11 | TiOPc, vapor-deposited | Comparative Compound 2 | 946 | 58 | 2.2 |

TABLE 16

| | Photoreceptor No. | Charge Generating Material | Charge Transporting Material | $V_0$ (-V) | $V_{R10}$ (-V) | $E_{1/2}$ (lux · sec) |
|---|---|---|---|---|---|---|
| Application Example 10 | 12 | $\tau$-$H_2$Pc | Exemplified Compound 5 | 826 | 0 | 1.0 |
| Application Example 11 | 13 | $\tau$-$H_2$Pc | Exemplified Compound 21 | 1238 | 8 | 1.2 |
| Application Example 12 | 14 | $\tau$-$H_2$Pc | Exemplified Compound 41 | 1184 | 4 | 1.2 |
| Application Comparative Example 3 | 15 | $\tau$-$H_2$Pc | Comparative Compound 2 | 67 | 5 | 1.8 |
| Application Example 13 | 16 | x-$H_2$Pc | Exemplified Compound 21 | 1238 | 8 | 1.2 |
| Application Example 14 | 17 | x-$H_2$Pc | Exemplified Compound 41 | 916 | 0 | 1.5 |
| Application Example 15 | 18 | crystalline TiOPc, dispersed | Exemplified Compound 5 | 300 | 0 | 0.6 |
| Application Example 16 | 19 | crystalline TiOPc, dispersed | Exemplified Compound 21 | 766 | 8 | 0.6 |

TABLE 16-continued

| Photo-receptor No. | Charge Generating Material | Charge Transporting Material | $V_0$ (-V) | $V_{R10}$ (-V) | $E_{1/2}$ (lux · sec) |
|---|---|---|---|---|---|
| Application Example 17 | 20 | crystalline TiOPc, dispersed | Exemplified Compound 41 | 832 | 0 | 0.8 |
| Application Comparative Example 4 | 21 | crystalline TiOPc, dispersed | Comparative Compound 2 | 70 | 4 | 12.0 |

APPLICATION EXAMPLES 13 AND 14

One part of x-form metal-free phthalocyanine (x-$H_2$PC) and 1 part of a butyral resin (Poly(vinyl butyral) BM-1, manufactured by Sekisui Chemical Co., Ltd.) were kneaded in a ball mill for 5 hours along with 30 parts of tetrahydrofuran as a solvent. The pigment dispersion obtained was applied on a sheet obtained by vapor-depositing aluminum on a poly(ethylene terephthalate) (PET) film, and the coating was dried at 50° C. for 2 hours to form a charge-generating layer. Further, 1 part of each of Exemplified Compounds 21 and 41 and 1 part of a polycarbonate resin (Polycarbonate Z, manufactured by Mitsubishi Gas Chemical Company, Inc.) were mixed in 8 parts of dichloroethane to dissolve them. Each of these solutions was applied on the charge-generating layer with a doctor blade and dried at 80° C. for 3 hours to produce photoreceptors 16 and 17. The photoreceptors thus obtained were examined for electrophotographic properties in the same manner as in Application Examples 1 to 3. The results obtained are shown in Table 16.

APPLICATION EXAMPLES 15 TO 17

One part of crystalline oxotitanium phthalocyanine (TiOPc crystals) produced in accordance with JP-A-63-20365 was added to a binder resin solution obtained by dissolving 1 part of a butyral resin (Poly(vinyl butyral) BM-1, manufactured by Sekisui Chemical Co., Ltd.) in 30 parts of tetrahydrofuran, and the pigment was dispersed by treating the mixture with an oscillating mill for 2 hours along with glass beads. This dispersion was applied with a wire-wound bar on a sheet obtained by vapor-depositing aluminum on a poly(ethylene terephthalate) (PET) film, and the coating was dried to form a charge-generating layer of about 0.5 mm thickness. Further, 1 part of each of Exemplified Compounds 5, 21, and 41 and 1 part of a polycarbonate resin (Polycarbonate Z, manufactured by Mitsubishi Gas Chemical Company, Inc.) were mixed in 8 parts of dichloroethane to dissolve them. Each of these solutions was applied on the charge-generating layer with a doctor blade and dried at 80° C. for 3 hours to produce photoreceptors 18 to 20. The photoreceptors thus obtained were examined for electrophotographic properties in the same manner as in Application Examples 1 to 3. The results obtained are shown in Table 16.

APPLICATION COMPARATIVE EXAMPLE 4

Photoreceptor 21 was produced in the same manner as in Application Examples 15 to 17, except that Comparative Compound 2 was used in place of Exemplified Compounds 5, 21, and 41. Its electrophotographic properties were examined in the same manner as in Application Examples 1 to 3. The results obtained are shown in Table 16. The photoreceptors employing Exemplified Compounds 5, 21, and 41 according to the present invention had values of $V_0$ of 300, 766, and 832, respectively, whereas the photoreceptor employing Comparative Compound 2 had a $V_0$ of 70. These results show that the compounds of this invention were distinctly superior. On the other hand, higher values of half-decay exposure $E_{1/2}$ show poor sensitivity. The photoreceptors employing Exemplified Compounds 5, 21, and 41 according to the present invention had values of $E_{1/2}$ of 0.6, 0.6, and 0.8, respectively, whereas the photoreceptor employing Comparative Compound 2 had an $E_{1/2}$ of 12.0. These results show that the compounds of this invention were distinctly superior.

APPLICATION EXAMPLES 18 TO 20

One part of a bisazo pigment (P) and 1 part of a polycarbonate resin (Yupilon E-2000, manufactured by Mitsubishi Gas Chemical Company, Inc.) were kneaded in a ball mill for 5 hours along with 30 parts of dichloroethane as a solvent. The pigment dispersion obtained was applied with a wire-wound bar on a sheet obtained by vapor-depositing aluminum on a poly(ethylene terephthalate) (PET) film, and the coating was dried at 45° C. for 3 hours to form a charge-generating layer having a thickness of about 1 μm. Further, 1 part of each of Exemplified Compounds 5, 21, and 41 and 1 part of a polycarbonate resin (Polycarbonate Z, manufactured by Mitsubishi Gas Chemical Company, Inc.) were mixed in 8 parts of dichloroethane to dissolve them. Each of these solutions was applied on the charge-generating layer with a doctor blade and dried at 80° C. for 3 hours to produce photoreceptors 22 to 24. Their electrophotographic properties were examined. The results obtained are shown in Table 17.

TABLE 17

| Photo-receptor No. | Charge Generating Material | Charge Transporting Material | $V_0$ (-V) | $V_{R10}$ (-V) | $E_{1/2}$ (lux · sec) |
|---|---|---|---|---|---|
| Application Example 18 | 22 | BisAzo(P) | Exemplified Compound 5 | 788 | 0 | 4.0 |
| Application Example 19 | 23 | BisAzo(P) | Exemplified Compound 21 | 1062 | 4 | 4.6 |
| Application Example 20 | 24 | BisAzo(P) | Exemplified Compound 41 | 1180 | 0 | 4.0 |

APPLICATION EXAMPLES 21 TO 24

One part of each of Exemplified Compounds 5, 21, 41, and 45 and 1 part of a polycarbonate resin were mixed in 8 parts of dichloroethane to dissolve them. Each of these solutions was applied with a doctor blade on a sheet obtained by vapor-depositing aluminum on a poly(ethylene terephthalate) (PET) film, and the coating was dried at 80° C. for 3 hours. Further, a translucent gold electrode was formed on the charge-transporting layer by vapor deposition to measure the carrier mobility. The measurement of carrier mobility was made by the time-of-flight method (Toshiaki Tanaka, Yasuhiro Yamaguchi, and Masaaki Yokoyama, Denshi-Shashin, 29, 366(1990)) using as an illuminant a nitrogen gas laser having a pulse half width of 0.9 nsec and a wavelength of 337 nm. The results obtained at 25° C. and 25 V/μm are shown in Table 18.

APPLICATION COMPARATIVE EXAMPLE 5

A film was produced and carrier mobility was measured in the same manner as in Application Examples 21 to 24, except that Comparative Compound 2 was used in place of Exemplified Compounds 5, 21, 41, and 45. The results obtained are shown in Table 18.

TABLE 18

| | Charge Transporting Material | Carrier Mobility $\mu$ (cm$^2$ V$^{-1}$ s$^{-1}$) |
|---|---|---|
| Application Example 21 | Exemplified Compound 5 | 96.1 × 10$^{-6}$ |
| Application Example 22 | Exemplified Compound 21 | 83.7 × 10$^{-6}$ |
| Application Example 23 | Exemplified Compound 41 | 65.9 × 10$^{-6}$ |
| Application Example 24 | Exemplified Compound 45 | 37.3 × 10$^{-6}$ |
| Application Comparative Example 5 | Comparative Compound 2 | 1.38 × 10$^{-6}$ |

Table 18 clearly shows that the compounds according to the present invention had higher carrier mobilities than the Comparative Compound.

APPLICATION EXAMPLES 25 AND 26

A charge-generating layer was formed in the same manner as in Application Examples 4 to 9 by vacuum-depositing oxotitanium phthalocyanine (TiOPc) at 10$^{-6}$ Torr to a thickness of about 0.8 mm. One part of each of Exemplified Compounds 21 and 41 as a charge-transporting material and 1 part of a bisphenol A/biphenyl type copolycarbonate resin represented by the following structural formula (manufactured by Idemitsu Kosan Co., Ltd., Japan) in place of the polycarbonate resin (Polycarbonate Z, manufactured by Mitsubishi Gas Chemical Company, Inc.) were mixed in 8 parts of dichloroethane to dissolve them. Each of these solutions was applied on the charge-generating layer with a doctor blade and dried at 80° C. for 3 hours. Thus, photoreceptors 25 and 26 were produced.

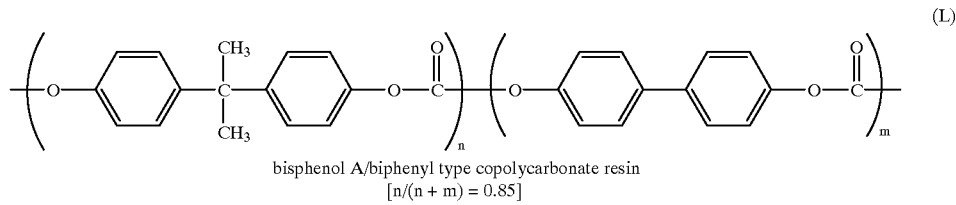

bisphenol A/biphenyl type copolycarbonate resin
[n/(n + m) = 0.85]

(L)

Photoreceptors 25 and 26 were examined for electrophotographic properties in the same manner as in Application Examples 1 to 3. The results obtained are shown in Table 19.

TABLE 19

| | Photo-receptor No. | Charge Generating Material | Charge Transporting Material | $V_0$ (-V) | $V_{R10}$ (-V) | $E_{1/2}$ (lux · sec) |
|---|---|---|---|---|---|---|
| Application Example 25 | 25 | TiOPc, vapor-deposited | Exemplified Compound 21 | 1332 | 0 | 1.1 |
| Application Example 26 | 26 | TiOPc, vapor-deposited | Exemplified Compound 41 | 1442 | 0 | 1.0 |

APPLICATION EXAMPLES 27 AND 28

A charge-generating layer comprising τ-form metal-free phthalocyanine (τ-H$_2$Pc) was formed in the same manner as in Application Examples 10 to 12. Further, 1 part of each of Exemplified Compounds 21 and 41 and 1 part of the bisphenol A/biphenyl type copolycarbonate resin used in Application Examples 25 and 26 (manufactured by Idemitsu Kosan Co., Ltd.) in place of the polycarbonate resin (Polycarbonate Z, manufactured by Mitsubishi Gas Chemical Company, Inc.) were mixed in 8 parts of dichloroethane to dissolve them. Each of these solutions was applied on the charge-generating layer with a doctor blade and dried at 80° C. for 3 hours. Thus, photoreceptors 27 and 28 were produced. Their electrophotographic properties were examined in the same manner as in Application Examples 1 to 3. The results obtained are shown in Table 20.

APPLICATION EXAMPLES 29 AND 30

A charge-generating layer comprising x-form metal-free phthalocyanine (x-H$_2$Pc) was formed in the same manner as in Application Examples 13 and 14. Further, 1 part of each of Exemplified Compounds 21 and 41 and 1 part of the bisphenol A/biphenyl type copolycarbonate resin used in Application Examples 25 and 26 (manufactured by Idemitsu Kosan Co., Ltd.) in place of the polycarbonate resin (Polycarbonate Z, manufactured by Mitsubishi Gas Chemical Company, Inc.) were mixed in 8 parts of dichloroethane to dissolve them. Each of these solutions was applied on the charge-generating layer with a doctor blade and dried at 80° C. for 3 hours. Thus, photoreceptors 29 and 30 were produced. Photoreceptors 29 and 30 were examined for electrophotographic properties in the same manner as in Application Examples 1 to 3. The results obtained are shown in Table 20.

APPLICATION EXAMPLES 31 and 32

A charge-generating layer comprising crystalline oxotitanium phthalocyanine (TiOPc crystals) was formed in the same manner as in Application Examples 15 to 17. Further, 1 part of each of Exemplified Compounds 21 and 41 and 1 part of the bisphenol A/biphenyl type copolycarbonate resin used in Application Examples 25 and 26 (manufactured by Idemitsu Kosan Co., Ltd.) in place of the polycarbonate resin (Polycarbonate Z, manufactured by Mitsubishi Gas Chemical Company, Inc.) were mixed in 8 parts of dichloroethane to dissolce them. Each of these solutions was applied on the charge-generating layer with a doctor blade and dried at 80° C. for 3 hours. Thus, photoreceptors 31 and 32 were produced. The photoreceptors thus obtained were examined for electrophotographic properties in the same manner as in Application Examples 1 to 3. The results obtained are shown in Table 20.

TABLE 20

| | Photo-receptor No. | Charge Generating Material | Charge Transporting Material | $V_0$ (-V) | $V_{R10}$ (-V) | $E_{1/2}$ (lux · sec) |
|---|---|---|---|---|---|---|
| Application Example 27 | 27 | τ-H$_2$Pc | Exemplified Compound 21 | 1180 | 0 | 1.1 |
| Application Example 28 | 28 | τ-H$_2$Pc | Exemplified Compound 41 | 858 | 0 | 1.1 |
| Application Example 29 | 29 | x-H$_2$Pc | Exemplified Compound 21 | 962 | 0 | 1.1 |

TABLE 20-continued

| Photo-receptor No. | Charge Generating Material | Charge Transporting Material | $V_0$ (-V) | $V_{R10}$ (-V) | $E_{1/2}$ (lux · sec) |
|---|---|---|---|---|---|
| Application Example 30 | 30 | x-H$_2$Pc | Exemplified Compound 41 | 922 | 0 | 1.3 |
| Application Example 31 | 31 | crystalline TiOPc, dispersed | Exemplified Compound 21 | 744 | 0 | 0.7 |
| Application Example 32 | 32 | crystalline TiOPc, dispersed | Exemplified Compound 41 | 612 | 0 | 0.6 |

APPLICATION EXAMPLES 33 AND 34

A charge-generating layer comprising a bisazo pigment (P) was formed in the same manner as in Application Examples 18 to 20. Further, 1 part of each of Exemplified Compounds 21 and 41 and 1 part of the bisphenol A/biphenyl type copolycarbonate resin used in Application Examples 25 and 26 (manufactured by Idemitsu Kosan Co., Ltd.) in place of the polycarbonate resin (Polycarbonate Z, manufactured by Mitsubishi Gas Chemical Company, Inc.) were mixed in 8 parts of dichloroethane to dissolve them. Each of these solutions was applied on the charge-generating layer with a doctor blade and dried at 80° C. for 3 hours. Thus, photoreceptors 33 and 34 were produced. Their electrophotographic properties were examined. The results obtained are shown in Table 21.

TABLE 21

| Photo-receptor No. | Charge Generating Material | Charge Transporting Material | $V_0$ (-V) | $V_{R10}$ (-V) | $E_{1/2}$ (lux · sec) |
|---|---|---|---|---|---|
| Application Example 33 | 33 | BisAzo(P) | Exemplified Compound 21 | 1144 | 0 | 6.5 |
| Application Example 34 | 34 | BisAzo(P) | Exemplified Compound 41 | 1100 | 0 | 5.8 |

APPLICATION EXAMPLES 35 AND 36

A charge-transporting layer was formed through 3-hour drying at 80° C. in the same manner as in Application Examples 21 to 24, except that 1 part of the bisphenol A/biphenyl type copolycarbonate resin used in Application Examples 25 and 26 (manufactured by Idemitsu Kosan Co., Ltd.) was used in place of the polycarbonate resin (Polycarbonate Z, manufactured by Mitsubishi Gas Chemical Company, Inc.). The measurement of carrier mobility was made by the time-of-flight method in the same manner as in Application Examples 21 to 24. The results of the carrier mobility measurement made at 25° C. and 25 V/µm are shown in Table 22.

Table 22 clearly shows that the compounds according to the present invention had high carrier mobilities.

TABLE 22

| | Charge Transporting Material | Carrier Mobility $\mu$ (cm$^2$ V$^{-1}$ s$^{-1}$) |
|---|---|---|
| Application Example 35 | Exemplified Compound 21 | 122 × 10$^{-6}$ |
| Application Example 36 | Exemplified Compound 41 | 96.1 × 10$^{-6}$ |

APPLICATION EXAMPLE 37

Photoreceptor 35 was produced and evaluated for electrophotographic properties in the same manner as in Application Example 1, except that a mixed charge-transporting material consisting of 0.4 part of Exemplified Compound 41 and 0.6 part of the hydrazone compound represented by the following formula (U) was used in place of 1 part of Exemplified Compound 1. The results obtained are shown in Table 23.

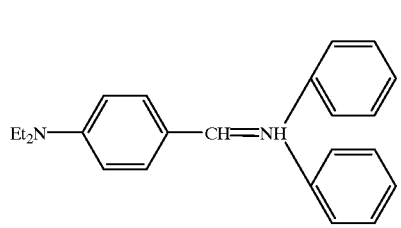

(U)

APPLICATION EXAMPLE 38

Photoreceptor 36 was produced and evaluated for electrophotographic properties in the same manner as in Application Example 10, except that a mixed charge-transporting material consisting of 0.4 part of Exemplified Compound 41 and 0.6 part of hydrazone compound (U) was used in place of 1 part of Exemplified Compound 5. The results obtained are shown in Table 23.

APPLICATION EXAMPLE 39

Photoreceptor 37 was produced and evaluated for electrophotographic properties in the same manner as in Application Example 13, except that a mixed charge-transporting material consisting of 0.4 part of Exemplified Compound 41 and 0.6 part of hydrazone compound (U) was used in place of 1 part of Exemplified Compound 21. The results obtained are shown in Table 23.

APPLICATION EXAMPLE 40

Photoreceptor 38 was produced and evaluated for electrophotographic properties in the same manner as in Application Example 15, except that a mixed charge-transporting material consisting of 0.4 part of Exemplified Compound 41 and 0.6 part of hydrazone compound (U) was used in place of 1 part of Exemplified Compound 5. The results obtained are shown in Table 23.

APPLICATION EXAMPLES 41 TO 43

Photoreceptors 39, 40, and 41 were produced and evaluated for electrophotographic properties in the same manner as in Application Examples 37, 38, and 39, respectively, except that the bisphenol A/biphenol type copolycarbonate resin used in Application Example 25 (manufactured by Idemitsu Kosan Co., Ltd.) was used in place of the polycarbonate resin (Polycarbonate Z, manufactured by Mitsubishi Gas Chemical Company, Inc.). The results obtained are shown in Table 23.

APPLICATION EXAMPLE 44

Photoreceptor 42 was produced and evaluated for electrophotographic properties in the same manner as in Application Example 1, except that a mixed charge-transporting material consisting of 0.4 part of Exemplified Compound 41 and 0.6 part of the hydrazone compound represented by the following formula (V) was used in place of 1 part of Exemplified Compound 1. The results obtained are shown in Table 23.

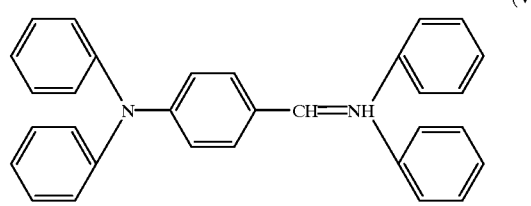

(V)

APPLICATION EXAMPLE 45

Photoreceptor 43 was produced and evaluated for electrophotographic properties in the same manner as in Application Example 10, except that a mixed charge-transporting material consisting of 0.4 part of Exemplified Compound 41 and 0.6 part of hydrazone compound (V) was used in place of 1 part of Exemplified Compound 5. The results obtained are shown in Table 24.

APPLICATION EXAMPLE 46

Photoreceptor was produced and evaluated for electrophotographic properties in the same manner as in Application Example 15, except that a mixed charge-transporting material consisting of 0.4 part of Exemplified Compound 41 and 0.6 part of hydrazone compound (V) was used in place of 1 part of Exemplified Compound 5. The results obtained are shown in Table 24.

APPLICATION EXAMPLE 47

Photoreceptor 45 was produced and evaluated for electrophotographic properties in the same manner as in Application Example 44, except that the bisphenol A/biphenol type copolycarbonate resin used in Application Example 25 (manufactured by Idemitsu Kosan Co., Ltd.) was used in place of the polycarbonate resin (Polycarbonate Z, manufactured by Mitsubishi Gas Chemical Company, Inc.). The results obtained are shown in Table 24.

APPLICATION EXAMPLE 48

Photoreceptor 46 was produced and evaluated for electrophotographic properties in the same manner as in Application Example 43, except that a mixed charge-transporting material consisting of 0.4 part of Exemplified Compound 41 and 0.6 part of hydrazone compound (V) was used in place of the mixed charge-transporting material used in Application Example 43. The results obtained are shown in Table 24.

APPLICATION EXAMPLE 49

Photoreceptor 47 was produced and evaluated for electrophotographic properties in the same manner as in Application Example 1, except that a mixed charge-transporting material consisting of 0.4 part of Exemplified Compound 41 and 0.6 part of the hydrazone compound represented by the following formula (W) was used in place of 1 part of Exemplified Compound 1. The results obtained are shown in Table 25.

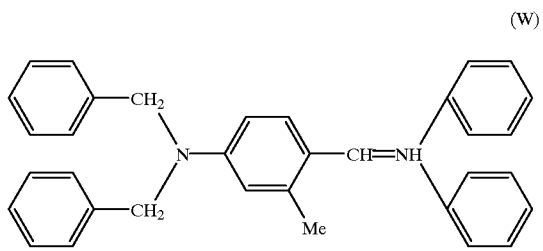

(W)

APPLICATION EXAMPLE 50

Photoreceptor 48 was produced and evaluated for electrophotographic properties in the same manner as in Application Example 10, except that a mixed charge-transporting material consisting of 0.4 part of Exemplified Compound 41 and 0.6 part of hydrazone compound (W) was used in place of 1 part of Exemplified Compound 5. The results obtained are shown in Table 25.

APPLICATION EXAMPLE 51

Photoreceptor 49 was produced and evaluated for electrophotographic properties in the same manner as in Application Example 13, except that a mixed charge-transporting material consisting of 0.4 part of Exemplified Compound 41 and 0.6 part of hydrazone compound (W) was used in place of 1 part of Exemplified Compound 21. The results obtained are shown in Table 25.

APPLICATION EXAMPLE 52

Photoreceptor 50 was produced and evaluated for electrophotographic properties in the same manner as in Application Example 15, except that a mixed charge-transporting material consisting of 0.4 part of Exemplified Compound 41 and 0.6 part of hydrazone compound (W) was used in place of 1 part of Exemplified Compound 5. The results obtained are shown in Table 25.

APPLICATION EXAMPLES 53 TO 56

Photoreceptors 51, 52, 53, and 54 were produced and evaluated for electrophotographic properties in the same manner as in Application Examples 49, 50, 51, and 52, respectively, except that the bisphenol A/biphenol type copolycarbonate resin used in Application Example 25 (manufactured by Idemitsu Kosan Co., Ltd.) was used in place of the polycarbonate resin (Polycarbonate Z, manufactured by Mitsubishi Gas Chemical Company, Inc.). The results obtained are shown in Table 25.

TABLE 23

| | Photoreceptor No. | Charge Generating Material | Charge Transporting Material | Charge Transporting Layer Polymer Binder | $V_0$ (-V) | $V_{R10}$ (-V) | $E_{1/2}$ (lux · sec) |
|---|---|---|---|---|---|---|---|
| Application Example 37 | 35 | CDB | Exemplified Compound 41 0.4 part Compound U 0.6 part | Polycarbonate z | 1105 | 7 | 4.2 |
| Application Example 38 | 36 | $\tau$-$H_2$Pc | Exemplified Compound 41 0.4 part Compound U 0.6 part | " | 776 | 12 | 1.0 |
| Application Example 39 | 37 | x-$H_2$Pc | Exemplified Compound 41 0.4 part Compound U 0.6 part | " | 964 | 7 | 1.9 |
| Application Example 40 | 38 | crystalline TiOPc, dispersed | Exemplified Compound 41 0.4 part Compound U 0.6 part | " | 675 | 11 | 0.6 |
| Application Example 41 | 39 | CDB | Exemplified Compound 41 0.4 part Compound U 0.6 part | Bisphenol A/biphenol type copolymer | 906 | 6 | 3.3 |
| Application Example 42 | 40 | $\tau$-$H_2$Pc | Exemplified Compound 41 0.4 part Compound U 0.6 part | Bisphenol A/biphenol type copolymer | 764 | 9 | 0.9 |
| Application Example 43 | 41 | x-$H_2$Pc | Exemplified Compound 41 0.4 part Compound U 0.6 part | Bisphenol A/biphenol type copolymer | 905 | 14 | 1.6 |

TABLE 24

| | Photoreceptor No. | Charge Generating Material | Charge Transporting Material | Charge Transporting Layer Polymer Binder | $V_0$ (-V) | $V_{R10}$ (-V) | $E_{1/2}$ (lux · sec) |
|---|---|---|---|---|---|---|---|
| Application Example 44 | 42 | CDB | Exemplified Compound 41 0.4 part Compound U 0.6 part | Polycarbonate z | 999 | 13 | 3.3 |
| Application Example 45 | 43 | $\tau$-$H_2$Pc | Exemplified Compound 41 0.4 part Compound U 0.6 part | " | 607 | 21 | 0.7 |
| Application Example 46 | 44 | crystalline TiOPc, dispersed | Exemplified Compound 41 0.4 part Compound U 0.6 part | " | 382 | 8 | 1.4 |
| Application Example 47 | 45 | CDB | Exemplified Compound 41 0.4 part Compound U 0.6 part | Bisphenol A/biphenol type copolymer | 879 | 8 | 2.7 |
| Application Example 48 | 46 | x-$H_2$Pc | Exemplified Compound 41 0.4 part Compound U 0.6 part | Bisphenol A/biphenol type copolymer | 751 | 11 | 1.1 |

TABLE 25

| | Photo-receptor No. | Charge Generating Material | Charge Transporting Material | Charge Transporting Layer Polymer Binder | $V_0$ (-V) | $V_{R10}$ (-V) | $E_{1/2}$ (lux·sec) |
|---|---|---|---|---|---|---|---|
| Application Example 49 | 47 | CDB | Exemplified Compound 41 0.4 part Compound U 0.6 part | Polycarbonate z | 1161 | 33 | 3.9 |
| Application Example 50 | 48 | τ-H₂Pc | Exemplified Compound 41 0.4 part Compound U 0.6 part | " | 699 | 12 | 1.0 |
| Application Example 51 | 49 | x-H₂Pc | Exemplified Compound 41 0.4 part Compound U 0.6 part | " | 891 | 21 | 1.6 |
| Application Example 52 | 50 | crystalline TiOPc, dispersed | Exemplified Compound 41 0.4 part Compound U 0.6 part | " | 617 | 11 | 1.0 |
| Application Example 53 | 51 | CDB | Exemplified Compound 41 0.4 part Compound U 0.6 part | Bisphenol A/biphenol type copolymer | 1079 | 12 | 4.5 |
| Application Example 54 | 52 | τ-H₂Pc | Exemplified Compound 41 0.4 part Compound U 0.6 part | Bisphenol A/biphenol type copolymer | 834 | 22 | 1.0 |
| Application Example 55 | 53 | x-H₂Pc | Exemplified Compound 41 0.4 part Compound U 0.6 part | Bisphenol A/biphenol type copolymer | 886 | 21 | 1.6 |
| Application Example 56 | 54 | crystalline TiOPc, dispersed | Exemplified Compound 41 0.4 part Compound U 0.6 part | Bisphenol A/biphenol type copolymer | 615 | 12 | 0.7 |

APPLICATION EXAMPLES 57 TO 60

The procedure of Application Example 1 was followed except that mixed charge-transporting materials comprising 0.4 part of Exemplified Compound 1 and 0.6 part of Exemplified Compound (2)-57, comprising 0.3 part of Exemplified Compound 1 and 0.7 part of Exemplified Compound (2)-57, comprising 0.2 part of Exemplified Compound 1 and 0.8 part of Exemplified Compound (2)-57 and comprising 0.1 part of Exemplified Compound 1 and 0.9 part of Exemplified Compound (2)-57, respectively, were used instead of 1 part of Exemplified Compound 1. Thus, photoreceptors 55, 56, 57 and 58 were prepared. These photoreceptors were then evaluated for electrophotographic properties. The results are set forth in Table 26.

APPLICATION EXAMPLES 61 TO 64

The procedure of Application Example 15 was followed except that mixed charge-transporting materials comprising 0.4 part of Exemplified Compound 1 and 0.6 part of Exemplified Compound (2)-57, comprising 0.3 part of Exemplified Compound 1 and 0.7 part of Exemplified Compound (2)-57, comprising 0.2 part of Exemplified Compound 1 and 0.8 part of Exemplified Compound (2)-57 and comprising 0.1 part of Exemplified Compound 1 and 0.9 part of Exemplified Compound (2)-57, respectively, were used instead of 1 part of Exemplified Compound 1. Thus, photoreceptors 59, 60, 61 and 62 were prepared. These photoreceptors were then evaluated for electrophotographic properties. The results are set forth in Table 26.

APPLICATION EXAMPLE 65

The procedure of Application Example 1 was followed except that a mixed charge-transporting material comprising 0.5 part of Exemplified Compound 1 and 0.5 part of Exemplified Compound (2)-57 was used instead of 1 part of Exemplified Compound 1. Thus, a photoreceptor 63 was prepared. The photoreceptor was then evaluated for electrophotographic properties. The results are set forth in Table 27.

APPLICATION EXAMPLE 66

The procedure of Application Example 4 was followed except that a mixed charge-transporting material comprising 0.5 part of Exemplified Compound 1 and 0.5 part of Exemplified Compound (2)-57 was used instead of 1 part of Exemplified Compound 1. Thus, a photoreceptor 64 was prepared. The photoreceptor was then evaluated for electrophotographic properties. The results are set forth in Table 27.

APPLICATION EXAMPLE 67

The procedure of Application Example 10 was followed except that a mixed charge-transporting material comprising 0.5 part of Exemplified Compound 1 and 0.5 part of Exemplified Compound (2)-57 was used instead of 1 part of Exemplified Compound 5. Thus, a photoreceptor 65 was prepared. The photoreceptor was then evaluated for electrophotographic properties. The results are set forth in Table 27.

APPLICATION EXAMPLE 68

The procedure of Application Example 13 was followed except that a mixed charge-transporting material comprising 0.5 part of Exemplified Compound 41 and 0.5 part of Exemplified Compound (2)-57 was used instead of 1 part of Exemplified Compound 21. Thus, a photoreceptor 66 was prepared. The photoreceptor was then evaluated for electrophotographic properties. The results are set forth in Table 27.

APPLICATION EXAMPLE 69

The procedure of Application Example 1 was followed except that a mixed charge-transporting material comprising 0.4 part of Exemplified Compound 1 and 0.6 part of Exemplified Compound (2)-76 was used instead of 1 part of Exemplified Compound 1. Thus, a photoreceptor 67 was prepared. The photoreceptor was then evaluated for electrophotographic properties. The results are set forth in Table 28.

APPLICATION EXAMPLE 70

The procedure of Application Example 15 was followed except that a mixed charge-transporting material comprising 0.4 part of Exemplified Compound 1 and 0.6 part of Exemplified Compound (2)-76 was used instead of 1 part of Exemplified Compound 5. Thus, a photoreceptor 68 was prepared. The photoreceptor was then evaluated for electrophotographic properties. The results are set forth in Table 28.

APPLICATION EXAMPLE 71

The procedure of Application Example 1 was followed except that a mixed charge-transporting material comprising 0.4 part of Exemplified Compound 1 and 0.6 part of Exemplified Compound (2)-33 was used instead of 1 part of Exemplified Compound 1. Thus, a photoreceptor 69 was prepared. The photoreceptor was then evaluated for electrophotographic properties. The results are set forth in Table 29.

APPLICATION EXAMPLE 72

The procedure of Application Example 13 was followed except that a mixed charge-transporting material comprising 0.4 part of Exemplified Compound 1 and 0.6 part of Exemplified Compound (2)-33 was used instead of 1 part of Exemplified Compound 21. Thus, a photoreceptor 70 was prepared. The photoreceptor was then evaluated for electrophotographic properties. The results are set forth in Table 29.

APPLICATION EXAMPLE 73

The procedure of Application Example 71 was followed except that the same bisphenol A/biphenol type copolymer polycarbonate resin as used in Application Example 25 was used instead of the polycarbonate resin. Thus, a photoreceptor 71 was prepared. The photoreceptor was then evaluated for electrophotographic properties. The results are set forth in Table 29.

APPLICATION EXAMPLE 74

The procedure of Application Example 1 was followed except that a mixed charge-transporting material comprising 0.4 part of Exemplified Compound 1 and 0.6 part of Exemplified Compound (2)-1 was used instead of 1 part of Exemplified Compound 1. Thus, a photoreceptor 72 was prepared. The photoreceptor was then evaluated for electrophotographic properties. The results are set forth in Table 30.

APPLICATION EXAMPLE 75

The procedure of Application Example 10 was followed except that a mixed charge-transporting material comprising 0.4 part of Exemplified Compound 1 and 0.6 part of Exemplified Compound (2)-1 was used instead of 1 part of Exemplified Compound 5. Thus, a photoreceptor 73 was prepared. The photoreceptor was then evaluated for electrophotographic properties. The results are set forth in Table 30.

APPLICATION EXAMPLE 76

0.4 Part of Exemplified Compound 1 and 0.6 part of Exemplified Compound (2)-57 were processed in the same manner as in Application Example 21 to prepare a photoreceptor 74 which was then measured for carrier mobility. The results are set forth in Table 31.

APPLICATION EXAMPLE 76-(1)

0.8 Part of Exemplified Compound 1 and 0.2 part of Exemplified Compound (2)-57 were processed in the same manner as in Application Example 21 to prepare a photoreceptor 75 which was then measured for carrier mobility. The results are set forth in Table 31.

TABLE 26

|  | Photoreceptor No. | Charge Generating Material | Charge Transporting Material | $V_0$ (-V) | $V_{R10}$ (-V) | $E_{1/2}$ (lux · sec) |
| --- | --- | --- | --- | --- | --- | --- |
| Application Example 57 | 55 | CDB | Exemplified Compound 1 0.4 part Exemplified Compound (2)-57 0.6 part | 1084 | 7 | 3.6 |
| Application Example 58 | 56 | " | Exemplified Compound 1 0.3 part Exemplified Compound (2)-57 0.7 part | 1045 | 1 | 3.7 |
| Application Example 59 | 57 | " | Exemplified Compound 1 0.2 part Exemplified Compound (2)-57 0.8 part | 818 | 24 | 3.9 |
| Application Example 60 | 58 | " | Exemplified Compound 1 0.1 part Exemplified Compound (2)-57 0.9 part | 891 | 2 | 3.7 |
| Application Example 61 | 59 | crystalline TiOPc, dispersed | Exemplified Compound 1 0.4 part Exemplified Compound (2)-57 0.6 part | 767 | 1 | 0.4 |

TABLE 26-continued

| | Photo-receptor No. | Charge Generating Material | Charge Transporting Material | $V_0$ (-V) | $V_{R10}$ (-V) | $E_{1/2}$ (lux · sec) |
|---|---|---|---|---|---|---|
| Application Example 62 | 60 | crystalline TiOPc, dispersed | Exemplified Compound 1 0.3 part Exemplified Compound (2)-57 0.7 part | 733 | 0 | 0.4 |
| Application Example 63 | 61 | crystalline TiOPc, dispersed | Exemplified Compound 1 0.2 part Exemplified Compound (2)-57 0.8 part | 643 | 0 | 0.3 |
| Application Example 64 | 62 | crystalline TiOPc, dispersed | Exemplified Compound 1 0.1 part Exemplified Compound (2)-57 0.9 part | 812 | 0 | 0.3 |

TABLE 27

| | Photo-receptor No. | Charge Generating Material | Charge Transporting Material | $V_0$ (-V) | $V_{R10}$ (-V) | $E_{1/2}$ (lux · sec) |
|---|---|---|---|---|---|---|
| Application Example 65 | 63 | CDB | Exemplified Compound 41 0.5 part Exemplified Compound (2)-57 0.5 part | 920 | 3 | 4.0 |
| Application Example 66 | 64 | TiOPc, vapor-deposited | Exemplified Compound 41 0.5 part Exemplified Compound (2)-57 0.5 part | 807 | 0 | 0.5 |
| Application Example 67 | 65 | τ-$H_2$Pc | Exemplified Compound 41 0.5 part Exemplified Compound (2)-57 0.5 part | 457 | 0 | 0.9 |
| Application Example 68 | 66 | x-$H_2$Pc | Exemplified Compound 41 0.5 part Exemplified Compound (2)-57 0.5 part | 816 | 0 | 1.5 |

TABLE 28

| | Photo-receptor No. | Charge Generating Material | Charge Transporting Material | $V_0$ (-V) | $V_{R10}$ (-V) | $E_{1/2}$ (lux · sec) |
|---|---|---|---|---|---|---|
| Application Example 69 | 67 | CDB | Exemplified Compound 1 0.4 part Exemplified Compound (2)-76 0.6 part | 880 | 39 | 2.4 |

TABLE 28-continued

| Photo-receptor No. | Charge Generating Material | Charge Transporting Material | $V_0$ (-V) | $V_{R10}$ (-V) | $E_{1/2}$ (lux · sec) |
|---|---|---|---|---|---|
| Application Example 70 | 68 | crystalline TiOPc, dispersed | Exemplified Compound 1 0.4 part Exemplified Compound (2)-76 0.6 part | 665 | 0 | 0.3 |

TABLE 29

| | Photo-receptor No. | Charge Generating Material | Charge Transporting Material | Charge Transporting Layer Polymer Binder | $V_0$ (-V) | $V_{R10}$ (-V) | $E_{1/2}$ (lux · sec) |
|---|---|---|---|---|---|---|---|
| Application Example 71 | 69 | CDB | Exemplified Compound 41 0.4 part Exemplified Compound (2)-33 0.6 part | Polycarbonate z | 967 | 0 | 3.5 |
| Application Example 72 | 70 | x-H$_2$Pc | Exemplified Compound 41 0.4 part Exemplified Compound (2)-33 0.6 part | " | 954 | 7 | 1.4 |
| Application Example 73 | 71 | CDB | Exemplified Compound 41 0.4 part Exemplified Compound (2)-33 0.6 part | Bisphenol A/biphenol type copolymer | 823 | 0 | 2.9 |

TABLE 30

| | Photo-receptor No. | Charge Generating Material | Charge Transporting Material | $V_0$ (-V) | $V_{R10}$ (-V) | $E_{1/2}$ (lux · sec) |
|---|---|---|---|---|---|---|
| Application Example 74 | 72 | CDB | Exemplified Compound 1 0.4 part Exemplified Compound (2)-1 0.6 part | 1155 | 0 | 4.0 |
| Application Example 75 | 73 | τ-H$_2$Pc | Exemplified Compound 1 0.4 part Exemplified Compound (2)-1 0.6 part | 448 | 2 | 3.6 |

TABLE 31

| | Photo-receptor No. | Charge Transporting Material | Carrier Mobility $\mu$ (cm$^2$ V$^{-1}$ s$^{-1}$) |
|---|---|---|---|
| Application Example 76 | 74 | Exemplified Compound 1 0.4 part Exemplified Compound (2)-57 0.6 part | $5.76 \times 10^{-6}$ |
| Application Example 76-(1) | 75 | Exemplified Compound 1 0.8 part Exemplified Compound (2)-57 0.2 part | $7.74 \times 10^{-6}$ |

APPLICATION EXAMPLE 77

A mixture of 0.15 g of the oxotitanium phthalocyanine (TiOPc) used in Application Example 15, 3.5 g of a polycarbonate (Polycarbonate Z, manufactured by Mitsubishi Gas Chemical Company, Inc.), 1.35 g of Exemplified Compound 41, and 31.5 g of dichloroethane was subjected to a 5-hour dispersion treatment using glass beads as a dispersing medium. The resulting dispersion was separated from the beads by filtration through a 200-mesh filter. This dispersion was applied with a doctor blade on a sheet obtained by vapor-depositing aluminum on a poly(ethylene terephthalate) (PET) film. The coating was dried in an oven at 80° C. for 3 hours to produce photoreceptor 75. The thus-obtained single-layer photoreceptor was negatively charged by −6 kV corona discharge to examine electrophotographic properties thereof by the same method as in Application Example 1. The results obtained are shown in Table 32.

Application Comparative Example 7

Single-layer photoreceptor 76 was produced and examined for electrophotographic properties in the same manner as in Application Example 77, except that triphenylamine (TPA; obtained by recrystallizing the TPA manufactured by Tokyo Kasei Kogyo Co., Ltd., Japan from a toluene/hexane mixed solvent; melting point, 127° C.) was used as Comparative Compound 3 in place of Exemplified Compound 41. The results obtained are shown in Table 32.

APPLICATION EXAMPLE 78

Single-layer photoreceptor 77 was produced in the same manner as in Application Example 77, except that the x-form metal-free phthalocyanine (x-$H_2$Pc) used in Application Example 3 was used in place of oxotitanium phthalocyanine (TiOPc) as a charge-generating material. This photoreceptor was negatively charged in the same manner as in Application Example 77 and evaluated for electrophotographic properties in the same manner as in Application Example 1. The results obtained are shown in Table 32.

APPLICATION COMPARATIVE EXAMPLE 8

Single-layer photoreceptor 78 was produced and examined for electrophotographic properties in the same manner as in Application Example 78, except that Comparative Compound 3 was used in place of Exemplified Compound 41. The results obtained are shown in Table 32.

APPLICATION EXAMPLE 79

Single-layer photoreceptor 75 produced in Application Example 77 was charged by 5-second corona discharge at +6 kV to measure the resulting surface potential $V_0$ (unit: V). This photoreceptor was placed in the dark for 5 seconds and then irradiated with light from a tungsten lamp at an illuminance of 5 lux to determine the exposure dose required for the surface potential to decrease by half, i.e., half-decay exposure $E_{1/2}$ (lux·sec), and the residual surface potential $VR_{R10}$ (V) after 10-second irradiation of light at an illuminance of 5 lux. The results obtained are shown in Table 33.

APPLICATION COMPARATIVE EXAMPLE 9

Single-layer photoreceptor 76 produced in Application Comparative Example 7 was positively charged by +6 kV corona discharge to evaluate electrophotographic properties thereof in the same manner as in Application Example 79. The results obtained are shown in Table 33.

APPLICATION EXAMPLE 60

Single-layer photoreceptor 77 produced in Application Example 78 was positively charged by +6 kV corona discharge to evaluate electrophotographic properties thereof in the same manner as in Application Example 79. The results obtained are shown in Table 33.

Application Comparative Example 10

Single-layer photoreceptor 78 produced in Application Comparative Example 8 was positively charged by +6 kV corona discharge to evaluate electrophotographic properties thereof in the same manner as in Application Example 79. The results obtained are shown in Table 33.

TABLE 32

| | | Single Layer Type Photoreceptor No. | Charge Generating Material | Charge Transporting Material | $V_0$ (-V) | $V_{R10}$ (-V) | $E_{1/2}$ (lux · sec) |
|---|---|---|---|---|---|---|---|
| Negative Electric Charge | Application Example 77 | 75 | crystalline TiOPc, dispersed | Exemplified Compound 41 | 912 | 0 | 1.3 |
| | Application Comparative Example 7 | 76 | crystalline TiOPc, dispersed | Comparative Compound 3 (TAP) | 984 | 78 | 3.1 |
| | Application Example 78 | 77 | x-$H_2$Pc | Exemplified Compound 41 | 742 | 24 | 4.8 |
| | Application Comparative Example 8 | 78 | x-$H_2$Pc | Comparative Compound 3 (TAP) | 960 | 100 | 5.5 |

TABLE 33

| | | Single Layer Type Photoreceptor No. | Charge Generating Material | Charge Transporting Material | $V_0$ (-V) | $V_{R10}$ (-V) | $E_{1/2}$ (lux · sec) |
|---|---|---|---|---|---|---|---|
| Positive Electric Charge | Application Example 79 | 75 | crystalline TiOPc, dispersed | Exemplified Compound 41 | 686 | 44 | 0.9 |

TABLE 33-continued

| | Single Layer Type Photoreceptor No. | Charge Generating Material | Charge Transporting Material | $V_0$ (-V) | $V_{R10}$ (-V) | $E_{1/2}$ (lux · sec) |
|---|---|---|---|---|---|---|
| Application Comparative Example 8 | 76 | crystalline TiOPc, dispersed | Comparative Compound 3 (TAP) | 824 | 120 | 2.7 |
| Application Example 80 | 77 | x-H$_2$Pc | Exemplified Compound 41 | 688 | 28 | 1.2 |
| Application Comparative Example 9 | 78 | x-H$_2$Pc | Comparative Compound 3 (TAP) | 726 | 100 | 3.5 |

As can be seen in Tables 32 and 33, the compounds according to the present invention exhibit appreciably good sensitivity and low residual potential as compared with the comparative compounds regardless of whether charged positively or negatively when used as a single-layer type photoreceptor.

APPLICATION EXAMPLE 81

The procedure of Application Example 4 was followed except that a mixed charge-transporting material comprising 0.4 part of Exemplified Compound 1 and 0.6 part of the following compound (Xa) was used instead of 1 part of Exemplified Compound 1 and a bisphenol A/biphenol type copolymer polycarbonate resin (available from Idemitsu Kosan Co., Ltd.) was used instead of the polycarbonate resin (Polycarbonate Z, available from Mitsubishi Gas Chemical Co., Inc.). Thus, a photoreceptor 79 was prepared. The photoreceptor was then evaluated for electrophotographic properties. The results are set forth in Table 34.

APPLICATION EXAMPLE 82

The procedure of Application Example 31 was followed except that a mixed charge-transporting material comprising 0.5 part of Exemplified Compound 1 and 0.5 part of the following compound (Xb) was used instead of 1 part of Exemplified Compound 21 or 41. Thus, a photoreceptor 80 was prepared. The photoreceptor was then evaluated for electrophotographic properties. The results are set forth in Table 34.

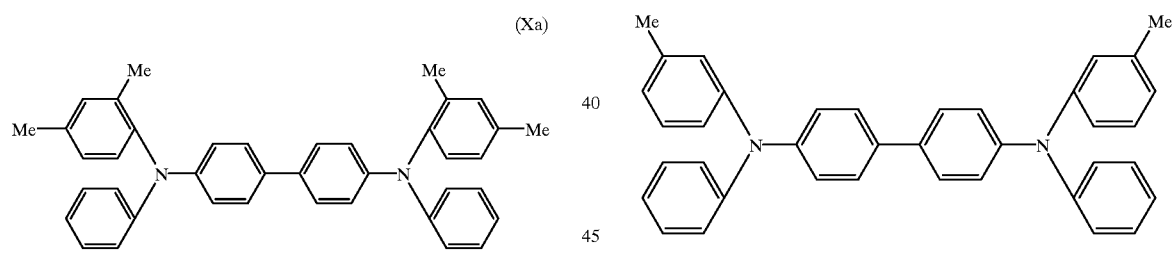

TABLE 34

| | Photoreceptor No. | Charge Generating Material | Charge Transporting Material | Charge Transporting Layer Polymer Binder | $V_0$ (-V) | $V_{R10}$ (-V) | $E_{1/2}$ (lux · sec) |
|---|---|---|---|---|---|---|---|
| Application Example 81 | 79 | TiOPc, vapor-deposited | Exemplified Compound 1 0.4 part Compound X 0.6 part | Bisphenol A/biphenol type copolymer | 901 | 0 | 0.5 |
| Application Example 82 | 80 | τ-H$_2$Pc | Exemplified Compound 1 0.4 part Compound X 0.6 part | Bisphenol A/biphenol type copolymer | 834 | 20 | 0.8 |

APPLICATION EXAMPLE 83

The procedure of Application Example 1 was followed except that a mixed charge-transporting material comprising 0.4 part of Exemplified Compound 1 and 0.6 part of the following compound (Y) was used instead of 1 part of Exemplified Compound 1. Thus, a photoreceptor 81 was prepared. The photoreceptor was then evaluated for electrophotographic properties. The results are set forth in Table 35.

used as an electrophotographic photoreceptor. Further, such an electrophotographic photoreceptor exhibits industrially excellent various properties, e.g., high sensitivity and no residual potential.

The preparation process according to the present invention can provide an industrially favorable process which can prepare the triphenylamine derivative (1) and/or compound (2) in a high yield.

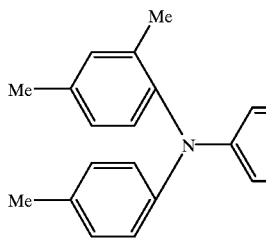
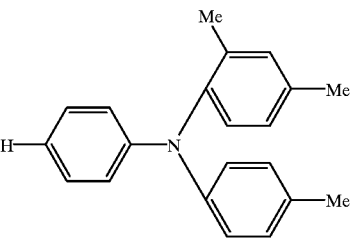

(Y)

APPLICATION EXAMPLE 84

The procedure of Application Example 4 was followed except that a mixed charge-transporting material comprising 0.4 part of Exemplified Compound 1 and 0.6 part of the foregoing compound (Y) was used instead of 1 part of Exemplified Compound 1. Thus, a photoreceptor 82 was prepared. The photoreceptor was then evaluated for electrophotographic properties. The results are set forth in Table 35.

APPLICATION EXAMPLE 85

The procedure of Application Example 10 was followed except that a mixed charge-transporting material comprising 0.4 part of Exemplified Compound 1 and 0.6 part of the foregoing compound (Y) was used instead of 1 part of Exemplified Compound 5. Thus, a photoreceptor 83 was prepared. The photoreceptor was then evaluated for electrophotographic properties. The results are set forth in Table 35.

What is claimed is:

1. A process for the preparation of a polysubstituted-triphenylamine derivative represented by the following general formula (4):

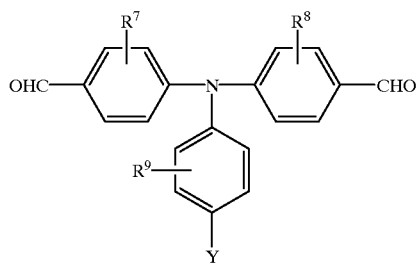

(4)

TABLE 35

| | Photo-receptor No. | Charge Generating Material | Charge Transporting Material | $V_0$ (-V) | $V_{R10}$ (-V) | $E_{1/2}$ (lux · sec) |
|---|---|---|---|---|---|---|
| Application Example 83 | 81 | CDB | Exemplified Compound 1 0.4 part Compound Y 0.6 part | 1144 | 0 | 3.5 |
| Application Example 84 | 82 | TiOPc, vapor-deposited | Exemplified Compound 1 0.4 part Compound Y 0.6 part | 729 | 12 | 0.5 |
| Application Example 85 | 83 | τ-H$_2$Pc | Exemplified Compound 1 0.4 part Compound Y 0.6 part | 581 | 0 | 0.6 |

INDUSTRIAL APPLICABILITY

As mentioned above, the triphenylamine derivative (1) of the present invention and a mixture thereof with the compound (2) exhibit excellent charge-transporting material properties and thus can exhibit a high carrier mobility when wherein $R^7$, $R^8$, and $R^9$ may be the same or different and each represent a hydrogen atom, a lower alkyl group, an alkoxy group, a phenoxy group, an aryl group, which aryl group may have a substituent group, or a halogen atom; and Y represents a formyl group, a hydrogen atom, a lower alkyl group, an alkoxy group, a phenoxy group, an aryl group, which aryl group may have a substituent group, or a halogen atom, which comprises reacting a triphenylamine derivative represented by the following general formula (3):

(3)

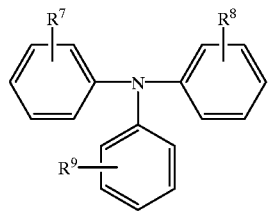

wherein $R^7$, $R^8$, and $R^9$ are as defined above with a Vilsmeier reagent prepared from a halogenating reagent and an N-substituted formamide in the presence of a catalyst which is an acid selected from the group consisting of a Lewis acid and/or a protonic acid to form a reaction product, and then subjecting the reaction product to hydrolysis with an alkaline aqueous solution, wherein the catalyst is added separately from the triphenylamine derivative of general formula (3) and the Vilsmeier reagent.

2. The process for the preparation of a poly-formyl-substituted triphenylamine derivative represented by the general formula (4) according to claim 1, wherein said Vilsmeier reagent is prepared from at least one halogenating reagent selected from the group consisting of phosphorus oxychloride, phosgene and thionyl chloride and at least one N-substituted formamide selected from the group consisting of N,N-dimethylformamide and N-methylformamide.

3. The process for the preparation of a poly-formyl-substituted triphenylamine derivative represented by the general formula (4) according to claim 1, wherein the reaction of the triphenylamine derivative represented by the general formula (3) with said Vilsmeier reagent is conducted in at least one reaction solvent selected from the group consisting of toluene, xylene, chlorobenzene and dichlorobenzene.

4. The process for the preparation of a polyformyl-substituted triphenylamine derivative represented by the general formula (4) according to claim 2, wherein the reaction of the triphenylamine derivative represented by the general formula (3) with said Vilsmeier reagent is conducted in at least one reaction solvent selected from the group consisting of toluene, xylene, chlorobenzene and dichlorobenzene.

5. The process of claim 1, wherein $R^7$, $R^8$, $R^9$ and Y are H.

6. A process for the preparation of a polysubstituted-triphenylamine derivative represented by the following general formula (4):

(4)

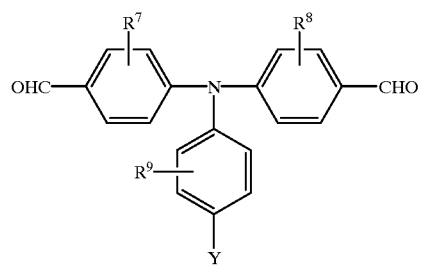

wherein $R^7$, $R^8$, and $R^9$ may be the same or different and each represent a hydrogen atom, a lower alkyl group, an alkoxy group, a phenoxy group, an aryl group, which aryl group may have a substituent group, or a halogen atom; and Y represents a formyl group, a hydrogen atom, a lower alkyl group, an alkoxy group, a phenoxy group, an aryl group, which aryl group may have a substituent group, or a halogen atom, which comprises reacting a triphenylamine derivative represented by the following general formula (3):

(3)

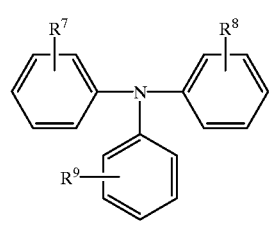

wherein $R^7$, $R^8$, and $R^9$ are as defined above with a Vilsmeier reagent prepared from a halogenating reagent and an N-substituted formamide in the presence of an acid selected from the group consisting of a Lewis acid and/or a protonic acid to form a reaction product, and then subjecting the reaction product to hydrolysis with an alkaline aqueous solution, wherein the reaction of the triphenylamine derivative represented by the general formula (3) with said Vilsmeier reagent is conducted in the presence of at least one member selected from the group consisting of a Lewis acid selected from the group consisting of zinc chloride, zinc bromide, boron trifluoride, aluminum chloride, titanium tetrachloride and tin chloride and/or a protonic acid selected from the group consisting of hydrogen chloride and hydrogen bromide.

7. A process for the preparation of a polysubstituted-triphenylamine derivative represented by the following general formula (4):

(4)

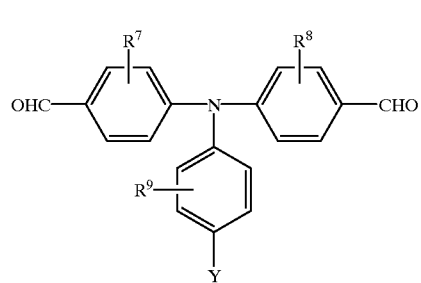

wherein $R^7$, $R^8$, and $R^9$ may be the same or different and each represent a hydrogen atom, a lower alkyl group, an alkoxy group, a phenoxy group, an aryl group, which aryl group may have a substituent group, or a halogen atom; and Y represents a formyl group, a hydrogen atom, a lower alkyl group, an alkoxy group, a phenoxy group, an aryl group, which aryl group may have a substituent group, or a halogen atom, which comprises reacting a triphenylamine derivative represented by the following general formula (3):

(3)

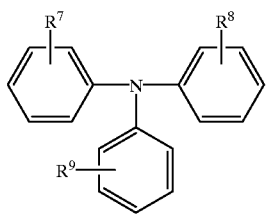

wherein $R^7$, $R^8$, and $R^9$ are as defined above with a Vilsmeier reagent prepared from a halogenating reagent and an N-substituted formamide in the presence of an acid selected from the group consisting of a Lewis acid and/or a protonic acid to form a reaction product, and then subjecting the reaction product to hydrolysis with an alkaline aqueous solution wherein the reaction of the triphenylamine derivative represented by the general formula (3) with said Vilsmeier reagent is conducted in the presence of at least one member selected from the group consisting of a Lewis acid selected from the group consisting of zinc chloride, zinc bromide, boron trifluoride, aluminum chloride, titanium tetrachloride and tin chloride and/or a protonic acid selected from the group consisting of hydrogen chloride and hydrogen bromide and further wherein said Vilsmeier reagent is prepared from at least one halogenating reagent selected from the group consisting of phosphorus oxychloride, phosgene and thionyl chloride and at least one N-substituted formamide selected from the group consisting of N,N-dimethylformamide and N-methylformamide.

8. A process for the preparation of a polysubstituted-triphenylamine derivative represented by the following general formula (4):

(4)

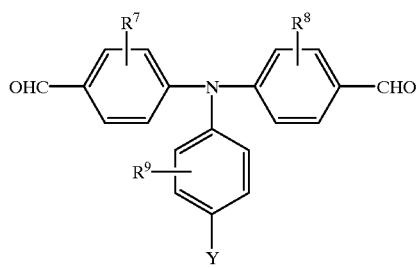

wherein $R^7$, $R^8$, and $R^9$ may be the same or different and each represent a hydrogen atom, a lower alkyl group, an alkoxy group, a phenoxy group, an aryl group, which aryl group may have a substituent groups or a halogen atom; and Y represents a formyl group, a hydrogen atom, a lower alkyl group, an alkoxy group, a phenoxy group, an aryl group, which aryl group may have a substituent group, or a halogen atom, which comprises reacting a triphenylamine derivative represented by the following general formula (3):

(3)

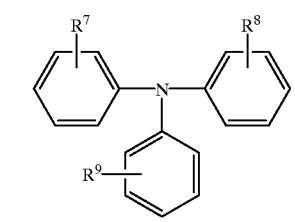

wherein $R^7$, $R^8$, and $R^9$ are as defined above with a Vilsmeier reagent prepared from a halogenating reagent and an N-substituted formamide in the presence of an acid selected from the group consisting of a Lewis acid and/or a protonic acid to form a reaction product, and then subjecting the reaction product to hydrolysis with an alkaline aqueous solution wherein the reaction of the triphenylamine derivative represented by the general formula (3) with said Vilsmeier reagent is conducted in the presence of at least one member selected from the group consisting of a Lewis acid selected from the group consisting of zinc chloride, zinc bromide, boron trifluoride, aluminum chloride, titanium tetrachloride and tin chloride and/or a protonic acid selected from the group consisting of hydrogen chloride and hydrogen bromide, and wherein the reaction of the triphenylamine derivative represented by the general formula (3) with said Vilsmeier reagent is conducted in at least one reaction solvent selected from the group consisting of toluene, xylene, chlorobenzene and dichlorobenzene.

* * * * *